US010239965B2

(12) United States Patent
Cruce et al.

(10) Patent No.: US 10,239,965 B2
(45) Date of Patent: Mar. 26, 2019

(54) CYCLIC OLEFIN RESIN COMPOSITIONS COMPRISING FUNCTIONAL ELASTOMERS

(71) Applicant: MATERIA, INC., Pasadena, CA (US)

(72) Inventors: Christopher J. Cruce, Poway, CA (US); Mark S. Trimmer, Monrovia, CA (US); Jason L. Moore, Altadena, CA (US)

(73) Assignee: MATERIA, INC., Pasadena, CA (US)

( * ) Notice: Subject to any disclaimer, the term of this patent is extended or adjusted under 35 U.S.C. 154(b) by 57 days.

(21) Appl. No.: 15/547,942

(22) PCT Filed: Feb. 11, 2016

(86) PCT No.: PCT/US2016/017449
§ 371 (c)(1),
(2) Date: Aug. 1, 2017

(87) PCT Pub. No.: WO2016/130743
PCT Pub. Date: Aug. 18, 2016

(65) Prior Publication Data
US 2018/0037677 A1     Feb. 8, 2018

Related U.S. Application Data

(60) Provisional application No. 62/115,270, filed on Feb. 12, 2015.

(51) Int. Cl.
| | | |
|---|---|---|
| C08F 4/70 | (2006.01) | |
| C08F 285/00 | (2006.01) | |
| C08J 5/24 | (2006.01) | |
| C08G 61/08 | (2006.01) | |
| C07F 15/02 | (2006.01) | |
| C08F 32/04 | (2006.01) | |
| C08G 18/76 | (2006.01) | |
| C08K 5/32 | (2006.01) | |
| C08K 7/06 | (2006.01) | |
| C08K 7/14 | (2006.01) | |
| C08L 51/04 | (2006.01) | |
| C08L 53/02 | (2006.01) | |
| C08L 65/00 | (2006.01) | |
| C08K 5/205 | (2006.01) | |

(52) U.S. Cl.
CPC ............... *C08F 4/70* (2013.01); *C07F 15/02* (2013.01); *C08F 32/04* (2013.01); *C08F 285/00* (2013.01); *C08G 18/7671* (2013.01); *C08G 61/08* (2013.01); *C08J 5/24* (2013.01); *C08K 5/32* (2013.01); *C08K 7/06* (2013.01); *C08K 7/14* (2013.01); *C08L 51/04* (2013.01); *C08L 53/025* (2013.01); *C08L 65/00* (2013.01); *C08G 2261/135* (2013.01); *C08G 2261/3325* (2013.01); *C08G 2261/418* (2013.01); *C08G 2261/62* (2013.01); *C08G 2261/76* (2013.01); *C08J 2365/04* (2013.01); *C08K 5/205* (2013.01)

(58) Field of Classification Search
CPC .. C08F 4/70; C08F 285/00; C08F 5/24; C08F 32/04; C08G 61/08; C07F 15/02; C08K 5/32; C08K 7/06
See application file for complete search history.

(56) References Cited

U.S. PATENT DOCUMENTS

| | | |
|---|---|---|
| 5,342,909 A | 8/1994 | Grubbs et al. |
| 5,728,785 A | 3/1998 | Grubbs et al. |
| 5,977,393 A | 11/1999 | Grubbs et al. |
| 6,284,852 B1 | 9/2001 | Lynn et al. |
| 6,409,875 B1 | 6/2002 | Giardello et al. |
| 6,486,279 B2 | 11/2002 | Lynn et al. |
| 6,552,139 B1 | 4/2003 | Herrmann et al. |
| 6,620,955 B1 | 9/2003 | Pederson et al. |
| 6,635,768 B1 | 10/2003 | Herrmann et al. |
| 6,730,736 B1 | 5/2004 | Kaita et al. |
| 6,787,620 B2 | 9/2004 | Herrmann et al. |
| 6,838,489 B2 | 1/2005 | Bell et al. |
| 6,921,735 B2 | 7/2005 | Hoveyda et al. |

(Continued)

FOREIGN PATENT DOCUMENTS

| | | |
|---|---|---|
| EP | 1757613 B1 | 1/2011 |
| EP | 1577282 B1 | 6/2011 |
| WO | 02/14376 A2 | 2/2002 |
| WO | 02/079208 A2 | 10/2002 |
| WO | 03/011455 A1 | 2/2003 |
| WO | 2010/037550 A1 | 4/2010 |
| WO | 2012/174502 A2 | 12/2012 |

OTHER PUBLICATIONS

International Search Report and Written Opinion in International Application No. PCT/US2016/017449, dated May 6, 2016.

(Continued)

*Primary Examiner* — John E Uselding
(74) *Attorney, Agent, or Firm* — Doina Gabriela Ene

(57) ABSTRACT

This invention relates to compositions and methods for improving the impact properties of polymer-matrix composites and to improving the adhesion of resin compositions to substrate materials. More particularly, the invention relates to compositions and methods for improving the impact properties of ring opening metathesis polymerization (ROMP) polymer-matrix composites and to improving the adhesion of ROMP compositions to substrate materials using adhesion promoters containing at least two isocyanate groups and functional elastomers comprising a maleic anhydride grafted styrene-ethylene/butylene-styrene hydrogenated copolymer in a resin composition. The polymer products produced via ROMP reactions of the invention may be utilized for a wide range of materials and composite applications. The invention has utility in the fields of polymer and materials chemistry and manufacture.

19 Claims, No Drawings

(56) References Cited

U.S. PATENT DOCUMENTS

| | | | |
|---|---|---|---|
| 7,026,495 | B1 | 4/2006 | Pederson et al. |
| 7,294,717 | B2 | 11/2007 | Herrmann et al. |
| 7,378,528 | B2 | 5/2008 | Herrmann et al. |
| 7,652,145 | B2 | 1/2010 | Herrmann et al. |
| 7,671,224 | B2 | 3/2010 | Winde et al. |
| 2003/0055262 | A1 | 3/2003 | Grubbs et al. |
| 2004/0132934 | A1 | 7/2004 | Grubbs et al. |
| 2007/0043188 | A1 | 2/2007 | Schaubroeck et al. |
| 2007/0060730 | A1 | 3/2007 | Jang et al. |
| 2007/0185343 | A1 | 8/2007 | Verpoort et al. |
| 2008/0293905 | A9 | 11/2008 | Schaubroeck et al. |
| 2014/0329017 | A1 | 11/2014 | Wang et al. |

OTHER PUBLICATIONS

International Preliminary Report on Patentability in International Application No. PCT/US2016/017449, dated Aug. 24, 2017.

Sanford et al., "New Insights into the Mechanism of Ruthenium-Catalyzed Olefin Metathesis Reactions", J. Am. Chem. Soc., 2001, 123, pp. 749-750.

Scholl et al., "Synthesis and Activity of a New Generation of Ruthenium-Based Olefin Metathesis Catalysts Coordinated with 1,3-Dimesityl-4,5-dihydromidazol-2-ylidene Ligands", Org. Lett. 1999, vol. 1, No. 6, pp. 953-956.

Schwab et al., "Synthesis and Applications of RuCl2(=CHR')(PR3)2: The Influence of the Alkylidene Moiety on Metathesis Activity", J. Am. Chem. Soc., 1996, 118, pp. 100-110.

Peter Schwab, Robert H. Grubbs and Joseph W. Ziller Synthesis and Applications of RuCl2(=CHR')(PR3)2: The Influence of the Alkylidene Moiety on Metathesis Activity J. Am. Chem. Soc. 1996, 118, 100-110.

Melanie S. Sanford, Michael Ulman, and Robert H. Grubbs New Insights into the Mechanism of Ruthenium-Catalyzed Olefin Metathesis Reactions J. Am. Chem. Soc. 2001, 123, 749-750.

Matthias Scholl, Sheng Ding, Choon Woo Lee, and Robert H. Grubbs Synthesis and Activity of a New Generation of Ruthenium-Based Olefin Metathesis Catalysts Coordinated with 1,3-Dimesityl-4,5-dihydroimidazol-2-ylidene Ligangs Org. Lett 1999 vol. 1, No. 6, 953-956.

CYCLIC OLEFIN RESIN COMPOSITIONS COMPRISING FUNCTIONAL ELASTOMERS

RELATED APPLICATIONS

This application claims the benefit of U.S. Provisional Patent Application No. 62/115,270, filed Feb. 12, 2015, the contents of which are incorporated herein by reference.

TECHNICAL FIELD

The present invention relates to methods and compositions for improving the adhesion of olefin metathesis compositions to substrate materials and for improving the impact properties (e.g., impact toughness or impact strength) of polymer-matrix composites. More particularly, the invention relates to methods and compositions for improving the adhesion of ring opening metathesis polymerization (ROMP) compositions to substrate materials and for improving the impact properties (e.g., impact toughness or impact strength) of ROMP polymer-matrix composites and the manufacture of polymer articles (e.g., polymer composite articles) via ROMP. Polymer products produced via the metathesis reactions of the invention may be utilized for a wide range of materials and composite applications. The invention has utility in the fields of polymer and materials chemistry and manufacture.

BACKGROUND

Polymer-matrix composites offer unique combinations of properties and are useful in a wide range of applications. Such composites may be fabricated utilizing either thermosetting or thermoplastic polymer matrix materials with a variety of particulate or fibrous fillers or reinforcements. It is generally advantageous to have strong adhesion between the polymer matrix material and the surfaces of the various particulate or fibrous substrates and there is considerable art related to substrate finishes and other treatments to optimize adhesion to polymer matrices. For example, in the production of long-fiber reinforced composites, improved adhesion between the polymer matrix and the fiber reinforcement leads to increased material performance. Good adhesion is particularly important where failures are likely to occur by delamination or by other adhesive failure modes.

As described in, for example, U.S. Pat. Nos. 5,840,238, 6,310,121, and 6,525,125, the disclosures of each of which are incorporated herein by reference, polymers generated by olefin metathesis processes are attractive as composite matrix materials. Of particularly beneficial use are the polymers generated by the ROMP of cyclic olefins. The low viscosity of cyclic olefin resin formulations and the ability to control ROMP kinetics (e.g., U.S. Pat. Nos. 4,708,969 and 5,939,504, the disclosures of both of which are incorporated herein by reference) facilitate composite processing and manufacture, and the corrosion resistance and high toughness of ROMP polymers leads to good composite durability. Additionally, certain properties of ROMP polymers, e.g., mechanical strength and stiffness, heat distortion temperature and solvent resistance, can be further enhanced by crosslinking induced via thermal treatment (e.g., U.S. Pat. No. 4,902,560, the disclosure of which is incorporated herein by reference) or chemically by addition of peroxides (e.g., U.S. Pat. No. 5,728,785, the disclosure of which is incorporated herein by reference).

Commercially important ROMP resin formulations generally based on readily available and inexpensive cyclic olefins such as dicyclopentadiene (DCPD), norbornenes, cyclooctadiene (COD), and various cycloalkenes. However, in contrast to traditional resin systems (e.g., epoxy, acrylate, urethane, and polyester resins) based on polar functional group chemistries, these nonpolar ROMP resins have poor intrinsic adhesion to the relatively polar surfaces of common carbon, glass, or mineral fillers and reinforcements. The addition of various silanes to such resin formulations for improvement of electrical and mechanical properties of ROMP polymers is described in U.S. Pat. Nos. 5,840,238, 6,001,909, and 7,339,006, the disclosures of each of which are incorporated herein by reference. Many widely used commercial silanes do not give optimal properties with ROMP polymers, however, and the greatest enhancements are only obtained when the silanes comprise groups with high metathesis activity (the relative reactivity of various metathesis active groups is described in J. Am. Chem. Soc., 2003, 125, 11360-11370).

As described in International Patent Application Number PCT/US12/42850, the disclosure of which is incorporated herein by reference, it was discovered that the addition of an adhesion promoter comprising a compound containing at least two isocyanate groups provides beneficial improvements in the adhesion of an olefin metathesis (e.g., ROMP) composition to substrate materials, such as, for example carbon and glass reinforcement materials. According to International Patent Application Number PCT/US12/42850, use of an adhesion promoter comprising a compound containing at least two isocyanate groups provided improved adhesion of ROMP polymer matrices compared to ROMP polymer matrices without such adhesion promoters, where adhesion of ROMP polymer matrices to substrate materials was measured by the short beam shear method according to ASTM D2344. Interlaminar shear strength (ILSS) is a measure of the adhesion and/or compatibility between the polymer matrix and the substrate material in a composite.

While International Patent Application Number PCT/US12/42850 demonstrated that compounds containing at least two isocyanate groups are effective to improve the adhesion of ROMP polymer matrices to substrate materials (e.g., carbon and/or glass reinforcement materials), the issue of making ROMP polymer-matrix composites possessing strong adhesion between the polymer matrix and substrate material as well as having improved impact properties (e.g., improved impact strength or improved impact toughness) was not specifically addressed.

It is known in the art that the impact properties (e.g., impact toughness or impact strength) of ROMP polymers can be improved by the use of impact modifiers. Typical impact modifiers known in the art for use with ROMP polymers include natural rubber, butyl rubber, polyisoprene, polybutadiene, polyisobutylene, ethylene-propylene copolymer, styrene-butadiene-styrene triblock rubber, random styrene-butadiene rubber, styrene-isoprene-styrene triblock rubber, styrene-ethylene/butylene-styrene copolymer, hydrogenated styrene-ethylene/butylene copolymer, styrene-ethylene/propylene-styrene copolymer, ethylene-propylene-diene terpolymers, ethylene-vinyl acetate, and nitrile rubbers. Specific impact modifiers known in the art include polybutadiene Diene 55AC 10 (Firestone), polybutadiene Diene® 55AM5 (Firestone), EPDM Royalene® 301T, EPDM Buna T9650 (Bayer), hydrogenated styrene-ethylene/butylene-styrene copolymer Kraton® G1651H (Kraton Polymers U.S. LLC), Polysar® Butyl 301 (Bayer), hydrogenated styrene-ethylene/butylene-styrene copolymer Kraton G1726M, Engage™ 8150 ethylene-octene copolymer (DuPont-Dow), styrene-butadiene Kraton D1184, EPDM Nordel® 1070 (DuPont-Dow), polyisobutylene Vistanex® MML-140 (Exxon), hydrogenated styrene-ethylene/butylene-styrene copolymer Kraton G1650M, hydrogenated styrene-ethylene/butylene-styrene copolymer Kraton G1657M, and styrene-butadiene block copolymer Kraton D1101. For example, U.S. Pat. Nos. 4,520,181, 4,943,621, and 6,838,486 disclose the use of impact modifiers to improve the impact properties (e.g., impact toughness or impact strength) of ROMP polymers, where one or more impact modifiers are typically dissolved in a cyclic olefin resin and the selected impact modifier(s) should not interfere with the polymerization reaction. Therefore, when making ROMP polymer-matrix composites having enhanced impact properties (e.g., improved impact toughness or impact strength) it is important that the impact modifier does not interfere with the polymerization reaction and it is also important that the impact modifier does not interfere with the ability of an adhesion promoter to effectuate adhesion between the ROMP polymer-matrix and the substrate material (e.g., glass and/or carbon reinforcement material).

Surprisingly, the inventors have discovered that hydrogenated styrene-ethylene/butylene-styrene copolymers known in the art for use with ROMP polymers as impact modifiers may interfere with the ability of adhesion promoters comprising at least two isocyanate groups to effectuate adhesion between ROMP polymer-matrices and composite substrate materials thereby adversely affecting the mechanical properties of the polymerized resin and/or polymer-matrix composite.

Despite the advances achieved in the art, particularly in the properties of olefin metathesis polymers (e.g., ROMP polymers) and their associated applications, a continuing need therefore exists for further improvement in a number of areas, including the manufacture of polymer-matrix composites, in particular ROMP polymer-matrix composites, where such composites possess strong adhesion between the polymer matrix and substrate material (e.g., carbon and/or glass reinforcement materials) as well as enhanced impact properties (e.g., improved impact strength or impact toughness).

SUMMARY OF INVENTION

The present invention is directed to addressing one or more of the aforementioned concerns and relates to the use of a functional elastomer in an resin composition comprising at least one cyclic olefin, at least one adhesion promoter comprising at least one compound containing at least two isocyanate groups, and at least one metal carbene olefin metathesis catalyst, where the resin composition is contacted with a substrate material to provide useful improvements in the mechanical properties of a polymer-matrix composite and/or a polymerized resin More particularly, the inventors have discovered that addition of a functional elastomer according to the invention to a resin composition, particularly a ROMP composition, comprising at least one cyclic olefin, at least one adhesion promoter comprising at least one compound containing at least two isocyanate groups, and at least one metal carbene olefin metathesis catalyst, where the ROMP composition is contacted with a substrate material provides useful improvements in the adhesion of the resin composition to the substrate material and provides useful improvements in the impact properties (e.g., impact strength or impact toughness) of the polymer-matrix composite and/or polymerized resin.

Functional elastomers according to the invention, discussed infra, are generally comprised of a maleic anhydride grafted styrene-ethylene/butylene-styrene hydrogenated copolymer (e.g., Kraton FG1901G and Kraton FG1924G).

In one embodiment, the invention provides a composition for improving the adhesion of a resin composition, for example a ROMP composition, to a substrate material (e.g., carbon and/or glass reinforcement material) and for improving the impact properties of a polymer-matrix composite, for example a ROMP polymer-matrix composite, in which a functional elastomer of the invention is combined with at least one cyclic olefin, at least one adhesion promoter comprising at least one compound containing at least two isocyanate groups, and at least one metal carbene olefin metathesis catalyst (e.g., a cyclic olefin metathesis catalyst), thereby forming a composition with improved mechanical properties.

In another embodiment, the invention provides a composition for improving the adhesion of a resin composition, for example a ROMP composition, to a substrate material (e.g., carbon and/or glass reinforcement material) and for improving the impact properties of a polymer-matrix composite, for example a ROMP polymer-matrix composite, in which a functional elastomer of the invention is combined with at least one cyclic olefin, at least one adhesion promoter comprising at least one compound containing at least two isocyanate groups, at least one metal carbene olefin metathesis catalyst (e.g., a cyclic olefin metathesis catalyst), and a substrate material, thereby forming a composition with improved mechanical properties.

In another embodiment, the invention provides a method for improving the adhesion of a resin composition, for example a ROMP composition, to a substrate material (e.g., carbon and/or glass reinforcement material) and for improving the impact properties of a polymer-matrix composite, for example a ROMP polymer-matrix composite, in which a functional elastomer of the invention is combined with at least one cyclic olefin, at least one adhesion promoter comprising at least one compound containing at least two isocyanate groups, and at least one metal carbene olefin metathesis catalyst (e.g., a cyclic olefin metathesis catalyst), thereby forming a resin composition with improved impact properties and contacting the resin composition with a substrate material (e.g., glass and/or carbon substrate material), thereby forming a polymer-matrix composite with improved mechanical properties.

In another embodiment, the invention provides a method for improving the adhesion of a resin composition, for example a ROMP composition, to a substrate material (e.g., carbon and/or glass reinforcement material) and for improving the impact properties of a polymer-matrix composite, for example a ROMP polymer-matrix composite, in which a functional elastomer of the invention is combined with at least one cyclic olefin, at least one adhesion promoter comprising at least one compound containing at least two isocyanate groups, at least one metal carbene olefin metathesis catalyst (e.g., a cyclic olefin metathesis catalyst), and a substrate material thereby forming a resin substrate composite material with improved properties.

In another embodiment, the invention provides a composition, comprising: at least one cyclic olefin; at least one metal carbene olefin metathesis catalyst; at least one adhesion promoter comprising at least one compound containing at least two isocyanate groups; and at least one functional elastomer, wherein the at least one functional elastomer is a maleic anhydride grafted styrene-ethylene/butylene-styrene hydrogenated copolymer.

In another embodiment, the invention provides a composition, comprising: at least one cyclic olefin; at least one metal carbene olefin metathesis catalyst; at least one adhesion promoter comprising at least one compound containing at least two isocyanate groups; at least one substrate material; and at least one functional elastomer, wherein the at least one functional elastomer is a maleic anhydride grafted styrene-ethylene/butylene-styrene hydrogenated copolymer.

In another embodiment, the invention provides a method for improving the impact properties of a polymer-matrix composite, comprising: combining at least one cyclic olefin, at least one metal carbene olefin metathesis catalyst, at least one adhesion promoter comprising at least one compound containing at least two isocyanate groups, and at least one functional elastomer to form a resin composition, contacting the resin composition with a substrate material, and subjecting the resin composition to conditions effective to promote an olefin metathesis reaction of the cyclic olefin, wherein the at least one functional elastomer is a maleic anhydride grafted styrene-ethylene/butylene-styrene hydrogenated copolymer.

In another embodiment, the invention provides a method for improving the adhesion of a resin composition to a substrate material, comprising: combining at least one cyclic olefin, at least one metal carbene olefin metathesis catalyst, at least one adhesion promoter comprising at least one compound containing at least two isocyanate groups, and at least one functional elastomer to form a resin composition, contacting the resin composition with the substrate material, and subjecting the resin composition to conditions effective to promote an olefin metathesis reaction of the cyclic olefin, wherein the at least one functional elastomer is a maleic anhydride grafted styrene-ethylene/butylene-styrene hydrogenated copolymer.

In another embodiment, the invention provides a method for improving the impact properties of a polymer-matrix composite, comprising: combining at least one cyclic olefin, at least one metal carbene olefin metathesis catalyst, at least one adhesion promoter comprising at least one compound containing at least two isocyanate groups, and at least one functional elastomer to form a ROMP composition, contacting the ROMP composition with a substrate material, and subjecting the ROMP composition to conditions effective to promote an olefin metathesis reaction of the cyclic olefin, wherein the at least one functional elastomer is a maleic anhydride grafted styrene-ethylene/butylene-styrene hydrogenated copolymer.

In another embodiment, the invention provides a method for improving the adhesion of a ROMP composition to a substrate material, comprising: combining at least one cyclic olefin, at least one metal carbene olefin metathesis catalyst, at least one adhesion promoter comprising at least one compound containing at least two isocyanate groups, and at least one functional elastomer to form a ROMP composition, contacting the ROMP composition with the substrate material, and subjecting the ROMP composition to conditions effective to promote an olefin metathesis reaction of the cyclic olefin, wherein the at least one functional elastomer is a maleic anhydride grafted styrene-ethylene/butylene-styrene hydrogenated copolymer.

In another embodiment, the invention provides a method for improving the impact properties of a polymer-matrix composite, comprising: combining at least one metal carbene olefin metathesis catalyst and a resin composition to form a ROMP composition, wherein the resin composition comprises at least one cyclic olefin, at least one adhesion promoter comprising at least one compound containing at least two isocyanate groups, and at least one functional elastomer, contacting the ROMP composition with a substrate material, and subjecting the ROMP composition to conditions effective to promote an olefin metathesis reaction of the cyclic olefin, wherein the at least one functional elastomer is a maleic anhydride grafted styrene-ethylene/butylene-styrene hydrogenated copolymer.

In another embodiment, the invention provides a method for improving the adhesion of a ROMP composition to a substrate material, comprising: combining at least one metal carbene olefin metathesis catalyst and a resin composition to form a ROMP composition, wherein the resin composition comprises at least one cyclic olefin, at least one adhesion promoter comprising at least one compound containing at least two isocyanate groups, and at least one functional elastomer, contacting the ROMP composition with the substrate material, and subjecting the ROMP composition to conditions effective to promote an olefin metathesis reaction of the cyclic olefin, wherein the at least one functional elastomer is a maleic anhydride grafted styrene-ethylene/butylene-styrene hydrogenated copolymer.

In another embodiment, the invention provides an article of manufacture comprising at least one resin composition comprising at least one cyclic olefin, at least one metal carbene olefin metathesis catalyst, at least one adhesion promoter comprising at least one compound containing at least two isocyanate groups, at least one substrate material, and at least one functional elastomer, wherein the at least one functional elastomer is a maleic anhydride grafted styrene-ethylene/butylene-styrene hydrogenated copolymer.

In another embodiment, the invention provides an article of manufacture comprising at least one ROMP composition comprising at least one cyclic olefin, at least one metal carbene olefin metathesis catalyst, at least one adhesion promoter comprising at least one compound containing at least two isocyanate groups, at least one substrate material, and at least one functional elastomer, wherein the at least one functional elastomer is a maleic anhydride grafted styrene-ethylene/butylene-styrene hydrogenated copolymer.

In another embodiment, the invention provides a ROMP composition, comprising: at least one cyclic olefin; at least one metal carbene olefin metathesis catalyst; at least one adhesion promoter comprising at least one compound containing at least two isocyanate groups; and at least one functional elastomer, wherein the at least one functional elastomer is a maleic anhydride grafted styrene-ethylene/butylene-styrene hydrogenated copolymer.

In another embodiment, the invention provides a ROMP composition, comprising: at least one cyclic olefin; at least one metal carbene olefin metathesis catalyst; at least one adhesion promoter comprising at least one compound containing at least two isocyanate groups; at least one substrate material; and at least one functional elastomer, wherein the at least one functional elastomer is a maleic anhydride grafted styrene-ethylene/butylene-styrene hydrogenated copolymer.

In another embodiment, the invention provides a resin composition, comprising: at least one cyclic olefin; at least one metal carbene olefin metathesis catalyst; at least one adhesion promoter comprising at least one compound containing at least two isocyanate groups; and at least one functional elastomer, wherein the at least one functional elastomer is a maleic anhydride grafted styrene-ethylene/butylene-styrene hydrogenated copolymer.

In another embodiment, the invention provides a resin composition, comprising: at least one cyclic olefin; at least one metal carbene olefin metathesis catalyst; at least one adhesion promoter comprising at least one compound containing at least two isocyanate groups; at least one substrate material; and at least one functional elastomer, wherein the at least one functional elastomer is a maleic anhydride grafted styrene-ethylene/butylene-styrene hydrogenated copolymer.

In another embodiment, the invention provides a ROMP composition, comprising: a resin composition and at least one metal carbene olefin metathesis catalyst, wherein the resin composition comprises at least one cyclic olefin, at least one adhesion promoter comprising at least one compound containing at least two isocyanate groups and at least one functional elastomer, wherein the at least one functional elastomer is a maleic anhydride grafted styrene-ethylene/butylene-styrene hydrogenated copolymer.

In another embodiment, the invention provides a ROMP composition, comprising: a resin composition and at least one metal carbene olefin metathesis catalyst, wherein the resin composition comprises at least one cyclic olefin, at least one adhesion promoter comprising at least one compound containing at least two isocyanate groups, at least one substrate material, and at least one functional elastomer, wherein the at least one functional elastomer is a maleic anhydride grafted styrene-ethylene/butylene-styrene hydrogenated copolymer.

In another embodiment, the invention provides an article of manufacture made by any of the embodiments or methods disclosed herein.

The invention is further directed to a resin composition, for example a ROMP composition, of a cyclic olefin, which may be functionalized or unfunctionalized and may be substituted or unsubstituted, at least one metal carbene olefin metathesis catalyst (e.g., a cyclic olefin metathesis catalyst), an adhesion promoter comprising at least one compound containing at least two isocyanate groups, a substrate material, and a functional elastomer of the invention. The inventive resin compositions are easy to handle and use and, when combined with a substrate material and cured, form resin substrate composite materials with improved properties. The resin compositions may also be contacted with a substrate material, rather than, or in addition to the substrate material added to the resin composition, and then subjected to conditions effective to promote an olefin metathesis reaction of the cyclic olefin in the presence of the at least one metal carbene olefin metathesis catalyst, the adhesion promoter, the functional elastomer, and the optional added substrate material and/or in contact with the substrate material.

The invention is further directed to a resin composition, for example, a ROMP composition, of a cyclic olefin, which may be functionalized or unfunctionalized and may be substituted or unsubstituted, at least one metal carbene olefin metathesis catalyst, a functional elastomer of the invention, an adhesion promoter comprising at least one compound containing at least two isocyanate groups, and a substrate material, such as, for example, a glass substrate material or a carbon substrate material. The functional elastomer should be present in an amount effective to improve adhesion to a substrate material and to improve the impact properties (e.g., impact strength or impact toughness) of the polymer-matrix composite when the resin composition is subjected to metathesis catalysis conditions in presence of the substrate material. The adhesion promoter may also be a mixture of compounds, wherein each compound contains at least two isocyanates. The functional elastomer may be a mixture of functional elastomers wherein each functional elastomer is comprised of a maleic anhydride grafted styrene-ethylene/butylene-styrene hydrogenated copolymer (e.g., Kraton FG1901G and Kraton FG1924G).

The addition of the functional elastomer of the invention provides beneficial improvements in the impact properties of a ROMP polymer-matrix composite as compared to a resin composition that is the same with the exception that the functional elastomer of the invention is not included. Furthermore, the addition of the functional elastomer of the invention also provides beneficial improvements in the adhesion of an olefin metathesis (e.g., ROMP) composition to a substrate material (e.g., carbon and/or glass substrate material) as compared to a resin composition that is the same with the exception that the functional elastomer of the invention is not included.

These and other aspects of the invention will be apparent to the skilled artisan in light of the following detailed description and examples.

DETAILED DESCRIPTION OF THE DISCLOSURE

Terminology and Definitions

Unless otherwise indicated, the invention is not limited to specific reactants, substituents, catalysts, resin compositions, reaction conditions, or the like, as such may vary. It is also to be understood that the terminology used herein is for the purpose of describing particular embodiments only and is not to be interpreted as being limiting.

As used in the specification and the appended claims, the singular forms "a," "an," and "the" include plural referents unless the context clearly dictates otherwise. Thus, for example, reference to "an α-olefin" includes a single α-olefin as well as a combination or mixture of two or more α-olefins, reference to "a substituent" encompasses a single substituent as well as two or more substituents, and the like.

As used in the specification and the appended claims, the terms "for example," "for instance," "such as," or "including" are meant to introduce examples that further clarify more general subject matter. Unless otherwise specified, these examples are provided only as an aid for understanding the invention, and are not meant to be limiting in any fashion.

In this specification and in the claims that follow, reference will be made to a number of terms, which shall be defined to have the following meanings:

The term "alkyl" as used herein refers to a linear, branched, or cyclic saturated hydrocarbon group typically although not necessarily containing 1 to about 24 carbon atoms, preferably 1 to about 12 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl, and the like. Generally, although again not necessarily, alkyl groups herein contain 1 to about 12 carbon atoms. The term "lower alkyl" refers to an alkyl group of 1 to 6 carbon atoms, and the specific term "cycloalkyl" refers to a cyclic alkyl group, typically having 4 to 8, preferably 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to about 12 carbon atoms. The term "lower alkenyl" refers to an alkenyl group of 2 to 6 carbon atoms, and the specific term "cycloalkenyl" refers to a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkenylene" as used herein refers to a difunctional linear, branched, or cyclic alkenyl group, where "alkenyl" is as defined above.

The term "alkynyl" as used herein refers to a linear or branched hydrocarbon group of 2 to about 24 carbon atoms containing at least one triple bond, such as ethynyl, n-propynyl, and the like. Preferred alkynyl groups herein contain 2 to about 12 carbon atoms. The term "lower alkynyl" refers to an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein refers to an alkyl group bound through a single, terminal ether linkage; that is, an "alkoxy" group may be represented as —O-alkyl where alkyl is as defined above. A "lower alkoxy" group refers to an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, as will be described in further detail infra.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 24 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred alkaryl and aralkyl groups contain 6 to 24 carbon atoms, and particularly preferred alkaryl and aralkyl groups contain 6 to 16 carbon atoms. Alkaryl groups include, without limitation, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, —(CO)-aralkyl, —(CO)-alkaryl, —(CO)-alkenyl, or —(CO)-alkynyl, and the term "acyloxy" refers to substituents having the formula —O(CO)-alkyl, —O(CO)-aryl, —O(CO)-aralkyl, —O(CO)-alkaryl, —O(CO)-alkenyl, —O(CO)-alkynyl wherein "alkyl," "aryl," "aralkyl", alkaryl, alkenyl, and alkynyl are as defined above.

The terms "cyclic" and "ring" refer to alicyclic or aromatic groups that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic, or polycyclic.

The terms "halo" and "halogen" are used in the conventional sense to refer to a chloro, bromo, fluoro, or iodo substituent.

"Hydrocarbyl" refers to univalent hydrocarbyl radicals containing 1 to about 30 carbon atoms, preferably 1 to about 24 carbon atoms, most preferably 1 to about 12 carbon atoms, including linear, branched, cyclic, saturated, and unsaturated species, such as alkyl groups, alkenyl groups, alkynyl groups, aryl groups, and the like. The term "lower hydrocarbyl" intends a hydrocarbyl group of 1 to 6 carbon atoms, preferably 1 to 4 carbon atoms, and the term "hydrocarbylene" refers to a divalent hydrocarbyl moiety containing 1 to about 30 carbon atoms, preferably 1 to about 24 carbon atoms, most preferably 1 to about 12 carbon atoms, including linear, branched, cyclic, saturated, and unsaturated species. The term "lower hydrocarbylene" refers to a hydrocarbylene group of 1 to 6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and heteroatom-containing hydrocarbylene moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus, or silicon, typically nitrogen, oxygen, or sulfur. Similarly, the term "heteroalkyl" refers to an alkyl substituent that is heteroatom-containing, the term "heterocyclic" refers to a cyclic substituent that is heteroatom-containing, the terms "heteroaryl" and "heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include without limitation alkoxyaryl, alkylsulfanyl-substituted alkyl, N-alkylated amino alkyl, and the like. Examples of heteroaryl substituents include without limitation pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups include without limitation pyrrolidino, morpholino, piperazino, piperidino, etc.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation: functional groups referred to herein as "Fn," such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ haloalkyl)-substituted carbamoyl (—(CO)—NH($C_1$-$C_{24}$ haloalkyl)), di-($C_1$-$C_{24}$ haloalkyl)-substituted carbamoyl (—(CO)—N($C_1$-$C_{24}$ haloalkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl (—(CO)—N($C_1$-$C_{24}$ alkyl)($C_5$-$C_{24}$ aryl), thiocarbamoyl (—(CS)—NH$_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-($C_5$-$C_{24}$ aryl)-substituted thiocarbamoyl (—(CS)—NH-aryl), di-($C_5$-$C_{24}$ aryl)-substituted thiocarbamoyl (—(CS)—N($C_5$-$C_{24}$ aryl)$_2$), di-N—($C_1$-$C_{24}$ alkyl), N—($C_5$-$C_{24}$ aryl)-substituted thiocarbamoyl (—(CS)—N($C_1$-$C_{24}$ alkyl)($C_5$-$C_{24}$ aryl), carbamido (—NH—(CO)—NH$_2$), cyano (—C≡N), cyanato (—O—C≡N), thiocyanato (—S—C≡N), isocyanate (—N=C=O), thioisocyanate (—N=C=S), formyl (—(CO)—H), thioformyl (—(CS)—H), amino (—NH$_2$), mono-($C_1$-$C_{24}$ alkyl)-substituted amino (—NH($C_1$-$C_{24}$ alkyl), di-($C_1$-$C_{24}$ alkyl)-substituted amino (—N($C_1$-$C_{24}$ alkyl)$_2$), mono-($C_5$-$C_{24}$ aryl)-substituted amino (—NH($C_5$-$C_{24}$ aryl), di-($C_5$-$C_{24}$ aryl)-substituted amino (—N($C_5$-$C_{24}$ aryl)$_2$), $C_2$-$C_{24}$ alkylamido (—NH—(CO)-alkyl), $C_6$-$C_{24}$ arylamido (—NH—(CO)-aryl), imino (—CR=NH where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR=N(alkyl), where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R includes without limitation hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO$_2$-alkyl), $C_1$-$C_{24}$ monoalkylaminosulfonyl (—SO$_2$—N(H) alkyl), $C_1$-$C_{24}$ dialkylaminosulfonyl (—SO$_2$—N(alkyl)$_2$), $C_5$-$C_{24}$ arylsulfonyl (—SO$_2$-aryl), boryl (—BH$_2$), borono (—B(OH)$_2$), boronato (—B(OR)$_2$ where R includes without limitation alkyl or other hydrocarbyl), phosphono (—P(O)(OH)$_2$), phosphonato (—P(O)(O$^-$)$_2$), phosphinato (—P(O)(O$^-$)), phospho (—PO$_2$), and phosphino (—PH$_2$); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably $C_2$-$C_6$ alkynyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

By "functionalized" as in "functionalized hydrocarbyl," "functionalized alkyl," "functionalized olefin," "functionalized cyclic olefin," and the like, is meant that in the hydrocarbyl, alkyl, olefin, cyclic olefin, or other moiety, at least one hydrogen atom bound to a carbon (or other) atom is replaced with one or more functional groups such as those described hereinabove. The term "functional group" is meant to include any functional species that is suitable for the uses described herein. In particular, as used herein, a functional group would necessarily possess the ability to react with or bond to corresponding functional groups on a substrate surface.

In addition, the aforementioned functional groups may, if a particular group permits, be further substituted with one or more additional functional groups or with one or more hydrocarbyl moieties such as those specifically mentioned above. Analogously, the above-mentioned hydrocarbyl moieties may be further substituted with one or more functional groups or additional hydrocarbyl moieties as noted above.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The term "substrate material" as used herein, is intended to generally mean any material that the resin compositions of the invention may be contacted with, applied to, or have the substrate material incorporated in to the resin. Without limitation, such materials include reinforcing materials, such as filaments, fibers, rovings, mats, weaves, fabrics, knitted material, cloth or other known structures, glass fibers and fabrics, carbon fibers and fabrics, aramid fibers and fabrics, and polyolefin or other polymer fibers or fabrics. Other suitable substrate materials include metallic density modulators, microparticulate density modulators, such as microspheres, and macroparticulate density modulators, such as glass or ceramic beads.

Functional Elastomer

Functional elastomers of the present invention disclosed herein are generally maleic anhydride grafted styrene-ethylene/butylene-styrene hydrogenated copolymers (hydrogenated SEBS-g-MA). Maleic anhydride grafted styrene-ethylene/butylene-styrene hydrogenated copolymers according to the invention preferably comprise 0.1-10 wt. % grafted maleic anhydride, more preferably comprise 0.3-7 wt. % grafted maleic anhydride, and even more preferably comprise 0.5-5 wt. % maleic anhydride. Maleic anhydride grafted styrene-ethylene/butylene-styrene hydrogenated copolymers according to the invention preferably comprise 10-60% polystyrene content, more preferably comprise 10-50% polystyrene content; and even more preferably comprise 10-40% polystyrene content. Preferred functional elastomers are maleic anhydride grafted styrene-ethylene/butylene-styrene hydrogenated copolymer (Kraton FG1901G) and maleic anhydride grafted styrene-ethylene/butylene-styrene hydrogenated copolymer (Kraton FG1924G). According to data sheets and product brochures available from the manufacturer, Kraton Performance Polymers, and information provided on the manufacturer's website (www.kraton.com), Kraton FG1901G is a linear styrenic triblock copolymer with a hydrogenated midblock of styrene-ethylene/butylene-styrene with a polystyrene content of 30% containing 1.4-2.0 wt. % maleic anhydride grafted onto the midblock and Kraton FG1924G is a linear styrenic triblock copolymer with a hydrogenated midblock of styrene-ethylene/butylene-styrene with a polystyrene content of 13% containing 0.7-1.3 wt. % maleic anhydride grafted onto the midblock. According to the manufacturer's data sheets and product brochures for Kraton FG1901G and Kraton FG1924G in the grade nomenclature "G" indicates Kraton G hydrogenated styrenic block copolymers and "FG" denotes functionalized Kraton G. Any concentration of functional elastomer of the invention which improves the mechanical properties of the olefin composite is sufficient for the invention. In general, suitable amounts of functional elastomer range from 0.001-10 phr, particularly 0.05-10 phr, more particularly 0.1-10 phr, or even more particularly 0.5-4.0 phr.

Adhesion Promoter

Adhesion promoters that may be used in the present invention disclosed herein are generally compounds containing at least two isocyanate groups (such as, for example, methylene diphenyl diisocyanate and hexamethylene diisocyanate). The adhesion promoter may be a diisocyanate, triisocyanate, or polyisocyanate (i.e., containing four or more isocyanate groups). The adhesion promoter may be a mixture of at least one diisocyanate, triisocyanate, or polyisocyanate. In a more particular aspect of the invention, the adhesion promoter comprises, or is limited to, a diisocyanate compound, or mixtures of diisocyanate compounds.

In general, adhesion promoters that may be used in the present invention may be any compound having at least two isocyanate groups. Suitable adhesion promoters include, without limitation, isocyanate compounds comprising at least two isocyanate groups, and wherein the compounds are selected from hydrocarbyl, substituted hydrocarbyl, heteroatom-containing hydrocarbyl, substituted heteroatom-containing hydrocarbyl, and functionalized hydrocarbyl compounds. As described above, suitable hydrocarbyl adhesion promoter compounds generally include alkyl, cycloalkyl, alkylene, alkenyl, alkynyl, aryl, cycloalkyl, alkaryl, and aralkyl compounds. Substituted heteroatom-containing, and functionalized hydrocarbyl adhesion promoter compounds include the afore-mentioned hydrocarbyl compounds, as well as the variations thereof noted hereinabove.

Adhesion promoters that may be used in the present invention may be an alkyl diisocyanate. An alkyl diisocyanate refers to a linear, branched, or cyclic saturated or unsaturated hydrocarbon group typically although not necessarily containing 1 to about 24 carbon atoms, preferably a diisocyanate containing 2 to about 12 carbon atoms, and more preferably a diisocyanate containing 6 to 12 carbon atoms such as hexamethylene diisocyanate (HDI), octamethylene diisocyanate, decamethylene diisocyanate, and the like. Cycloalkyl diisocyanates contain cyclic alkyl group, typically having 4 to 16 carbon atoms. A preferred cycloalkyl diisocyanate containing 6 to about 12 carbon atoms are cyclohexyl, cyclooctyl, cyclodecyl, and the like. A more preferred cycloalkyl diisocyanate originates as a condensation product of acetone called 5-isocyanato-1-(isocyanatomethyl)-1,3,3-trimethyl-cyclohexane, commonly known as Isophorone diisocyanate (IPDI) and the isomers of isocyanato-[(isocyanatocyclohexyl)methyl]cyclohexane ($H_{12}MDI$). $H_{12}MDI$ is derived from the hydrogenated form of the aryl diisocyanate methylene diphenyl diisocyanate (MDI).

Adhesion promoters that may be used in the present invention may be an aryl diisocyanate. Aryl diisocyanates refers to aromatic diisocyanates containing a single aromatic ring or multiple aromatic rings that are fused together, directly linked, or indirectly linked (such that the different aromatic rings are bound to a common group such as a methylene or ethylene moiety). Preferred aryl diisocyanates contain 5 to 24 carbon atoms, and particularly preferred aryl diisocyanates contain 5 to 14 carbon atoms. Exemplary aryl diisocyanates contain one aromatic ring or two fused or linked aromatic rings, e.g., phenyl, tolyl, xylyl, naphthyl, biphenyl, diphenylether, benzophenone, and the like. Preferred aromatic diisocyanates include toluene diisocyanates, tetramethylxylene diisocyanate (TMXDI), and methylene diphenyl diisocyanate (MDI), which may comprise any mixture of its three isomers, 2,2'-MDI, 2,4'-MDI, and 4,4'-MDI.

Adhesion promoters that may be used in the present invention may be a polymer-containing isocyanate, such as, for example, diisocyanates. Polymer-containing isocyanates refers to a polymer-containing two or more terminal and/or pendant alkyl or aryl isocyanate groups. The polymer-containing isocyanates generally have to have a minimal solubility in the resin to provide improved mechanical properties. Preferred polymer-containing isocyanates include, but are not limited to, PM200 (poly MDI), Lupranate® (poly MDI from BASF), Krasol® isocyanate terminated polybutadiene prepolymers, such as, for example, Krasol® LBD2000 (TDI based), Krasol® LBD3000 (TDI based), Krasol® NN-22 (MDI based), Krasol® NN-23 (MDI based), Krasol® NN-25 (MDI based), and the like. Krasol® isocyanate terminated polybutadiene prepolymers are available from Cray Valley.

Adhesion promoters that may be used in the present invention may be a trimer of alkyl diisocyanates and aryl diisocyanates. In its simplest form, any combination of polyisocyanate compounds may be trimerized to form an isocyanurate ring containing isocyanate functional groups. Trimers of alkyl diisocyanate and aryl diisocyanates may also be referred to as isocyanurates of alkyl diisocyanate or aryl diisocyanate. Preferred alkyl diisocyanate and aryl diisocyanate trimers include, but are not limited to, hexamethylene diisocyanate trimer (HDIt), isophorone diisocyanate trimer, toluene diisocyanate trimer, tetramethylxylene diisocyanate trimer, methylene diphenyl diisocyanate trimers, and the like. More preferred adhesion promoters are toluene diisocyanates, tetramethylxylene diisocyanate (TMXDI), and methylene diphenyl diisocyanate (MDI) including any mixture of its three isomers 2,2'-MDI, 2,4'-MDI and 4,4'-MDI; liquid MDI; solid MDI; hexamethylenediisocyanatetrimer (HDIt); hexamethylenediisocyanate (HDI); isophorone diisocyanate (IPDI); 4,4'-methylene bis (cyclohexyl isocyanate) (H12MDI); polymeric MDI (PM200); MDI prepolymer (Lupranate® 5080); liquid carbodiimide modified 4,4'-MDI (Lupranate® MM103); liquid MDI (Lupranate® MI); liquid MDI (Mondur® ML); and liquid MDI (Mondur® MLQ). Even more preferred adhesion promoters are methylene diphenyl diisocyanate (MDI) including any mixture of its three isomers 2,2'-MDI, 2,4'-MDI and 4,4'-MDI; liquid MDI; solid MDI; hexamethylenediisocyanatetrimer (HDIt); hexamethylene diisocyanate (HDI); isophorone diisocyanate (IPDI); 4,4'-methylene bis (cyclohexyl isocyanate) (H12MDI); polymeric MDI (PM200); MDI prepolymer (Lupranate® 5080); liquid carbodiimide modified 4,4'-MDI (Lupranate® MM103); liquid MDI) (Lupranate® MI); liquid MDI (Mondur® ML); liquid MDI (Mondur® MLQ).

Any concentration of adhesion promoter which improves the mechanical properties of the olefin composite is sufficient for the invention. In general, suitable amounts of adhesion promoter range from 0.001-50 phr, particularly 0.05-10 phr, more particularly 0.1-10 phr, or even more particularly 0.5-4.0 phr.

Substrate Surfaces

The present invention is generally suitable for use with any substrate material in which the addition of a functional elastomer of the invention provides beneficial improvements in the adhesion of a resin (e.g., ROMP) composition to the substrate material as compared to a resin composition that is the same with the exception that the functional elastomer of the invention is not included. Furthermore, the present invention is generally suitable for use with any substrate material in which the addition of a functional elastomer of the invention provides beneficial improvements in the impact properties of a polymer-matrix composite (e.g., ROMP polymer-matrix composite) compared to a polymer-matrix composite that is the same with the exception that the functional elastomer of the invention is not included. The present invention is particularly beneficial for use with glass and carbon material surfaces suitable for use with epoxy and methacrylate resins, including those containing finishes or sizings, in which case the finishes or sizings do not need to be removed (e.g., by washing or heat cleaning) for the inventive functional elastomers to be effective. The present invention is also suitable for use with wood and aluminum materials. Suitable substrate materials may also be selected from fibrous, woven, microparticulate, ceramic, metal, polymer, and semiconductor materials. A polymer-matrix composite (e.g., ROMP polymer matrix composite) may be comprised of one substrate material or a mixture of different substrate materials.

Cyclic Olefin

Resin compositions that may be used with the present invention disclosed herein comprise one or more cyclic olefins. In general, any cyclic olefin suitable for the metathesis reactions disclosed herein may be used. Such cyclic olefins may be optionally substituted, optionally heteroatom-containing, mono-unsaturated, di-unsaturated, or poly-unsaturated $C_5$ to $C_{24}$ hydrocarbons that may be mono-, di-, or poly-cyclic. The cyclic olefin may generally be any strained or unstrained cyclic olefin, provided the cyclic olefin is able to participate in a ROMP reaction either individually or as part of a ROMP cyclic olefin composition. While certain unstrained cyclic olefins such as cyclohexene are generally understood to not undergo ROMP reactions by themselves, under appropriate circumstances, such unstrained cyclic olefins may nonetheless be ROMP active. For example, when present as a co-monomer in a ROMP composition, unstrained cyclic olefins may be ROMP active. Accordingly, as used herein and as would be appreciated by the skilled artisan, the term "unstrained cyclic olefin" is intended to refer to those unstrained cyclic olefins that may undergo a ROMP reaction under any conditions, or in any ROMP composition, provided the unstrained cyclic olefin is ROMP active.

In general, the cyclic olefin may be represented by the structure of formula (A)

(A)

wherein J, $R^{41}$, and $R^{42}$ are as follows:

$R^{41}$ and $R^{42}$ is selected independently from the group consisting of hydrogen, hydrocarbyl (e.g., $C_1$-$C_{20}$ alkyl, $C_5$-$C_{20}$ aryl, $C_5$-$C_{30}$ aralkyl, or $C_5$-$C_{30}$ alkaryl), substituted hydrocarbyl (e.g., substituted $C_1$-$C_{20}$ alkyl, $C_5$-$C_{20}$ aryl, $C_5$-$C_{30}$ aralkyl, or $C_5$-$C_{30}$ alkaryl), heteroatom-containing hydrocarbyl (e.g., $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl), and substituted heteroatom-containing hydrocarbyl (e.g., substituted $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl) and, if substituted hydrocarbyl or substituted heteroatom-containing hydrocarbyl, wherein the substituents may be functional groups ("Fn") such as phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, $C_5$-$C_{20}$ arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group (wherein the metal may be, for example, Sn or Ge). $R^{41}$ and $R^{42}$ may itself be one of the aforementioned groups, such that the Fn moiety is directly bound to the olefinic carbon atom indicated in the structure.

In the latter case, however, the functional group will generally not be directly bound to the olefinic carbon through a heteroatom containing one or more lone pairs of electrons, e.g., an oxygen, sulfur, nitrogen, or phosphorus atom, or through an electron-rich metal or metalloid such as Ge, Sn, As, Sb, Se, Te, etc. With such functional groups, there will normally be an intervening linkage $Z^*$, such that $R^{A1}$ and/or $R^{A2}$ then has the structure —$(Z^*)_n$-Fn wherein n is 1, Fn is the functional group, and $Z^*$ is a hydrocarbylene linking group such as an alkylene, substituted alkylene, heteroalkylene, substituted heteroalkene, arylene, substituted arylene, heteroarylene, or substituted heteroarylene linkage.

J is a saturated or unsaturated hydrocarbylene, substituted hydrocarbylene, heteroatom-containing hydrocarbylene, or substituted heteroatom-containing hydrocarbylene linkage, wherein when J is substituted hydrocarbylene or substituted heteroatom-containing hydrocarbylene, the substituents may include one or more —$(Z^*)_n$-Fn groups, wherein n is zero or 1, and Fn and $Z^*$ are as defined previously. Additionally, two or more substituents attached to ring carbon (or other) atoms within J may be linked to form a bicyclic or polycyclic olefin. J will generally contain in the range of approximately 5 to 14 ring atoms, typically 5 to 8 ring atoms, for a monocyclic olefin, and, for bicyclic and polycyclic olefins, each ring will generally contain 4 to 8, typically 5 to 7, ring atoms.

Mono-unsaturated cyclic olefins encompassed by structure (A) may be represented by the structure (B)

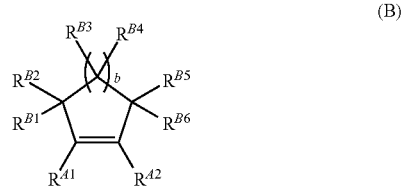

(B)

wherein b is an integer generally although not necessarily in the range of 1 to 10, typically 1 to 5, $R^{A1}$ and $R^2$ are as defined above for structure (A), and $R^{B1}$, $R^{B2}$, $R^B$, $R^{B4}$, $R^{B5}$, and $R^{B6}$ are independently selected from the group consisting of hydrogen, hydrocarbyl, substituted hydrocarbyl, heteroatom-containing hydrocarbyl, substituted heteroatom-containing hydrocarbyl and —$(Z^*)_n$-Fn where n, $Z^*$ and Fn are as defined previously, and wherein if any of the $R^{B1}$ through $R^{B6}$ moieties is substituted hydrocarbyl or substituted heteroatom-containing hydrocarbyl, the substituents may include one or more —$(Z^*)_n$-Fn groups. Accordingly, $R^{B1}$, $R^{B2}$, $R^{B3}$, $R^{B4}$, $R^{B5}$, and $R^{B6}$ may be, for example, hydrogen, hydroxyl, $C_1$-$C_{20}$ alkyl, $C_5$-$C_{20}$ aryl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, amino, amido, nitro, etc.

Furthermore, any of the $R^{B1}$, $R^{B2}$, $R^{B3}$, $R^{B4}$, $R^{B5}$, and $R^{B6}$ moieties can be linked to any of the other $R^{B1}$, $R^{B2}$, $R^{B3}$, $R^{B4}$, $R^{B5}$, and $R^{B6}$ moieties to provide a substituted or unsubstituted alicyclic group containing 4 to 30 ring carbon atoms or a substituted or unsubstituted aryl group containing 6 to 18 ring carbon atoms or combinations thereof and the linkage may include heteroatoms or functional groups, e.g., the linkage may include without limitation an ether, ester, thioether, amino, alkylamino, imino, or anhydride moiety. The alicyclic group can be monocyclic, bicyclic, or polycyclic. When unsaturated the cyclic group can contain monounsaturation or multiunsaturation, with monounsaturated cyclic groups being preferred. When substituted, the rings contain monosubstitution or multisubstitution wherein the substituents are independently selected from hydrogen, hydrocarbyl, substituted hydrocarbyl, heteroatom-containing hydrocarbyl, substituted heteroatom-containing hydrocarbyl, —$(Z^*)_n$-Fn where n is zero or 1, $Z^*$ and Fn are as defined previously, and functional groups (Fn) provided above.

Examples of monounsaturated, monocyclic olefins encompassed by structure (B) include, without limitation, cyclopentene, cyclohexene, cycloheptene, cyclooctene, cyclononene, cyclodecene, cycloundecene, cyclododecene, tricyclodecene, tetracyclodecene, octacyclodecene, and cycloeicosene, and substituted versions thereof such as 1-methylcyclopentene, 1-ethylcyclopentene, 1-isopropylcyclohexene, 1-chloropentene, 1-fluorocyclopentene, 4-methylcyclopentene, 4-methoxy-cyclopentene, 4-ethoxy-cyclopentene, cyclopent-3-ene-thiol, cyclopent-3-ene, 4-methylsulfanyl-cyclopentene, 3-methylcyclohexene, 1-methylcyclooctene, 1,5-dimethylcyclooctene, etc.

Monocyclic diene reactants encompassed by structure (A) may be generally represented by the structure (C)

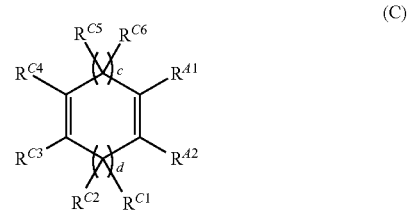

(C)

wherein c and d are independently integers in the range of 1 to about 8, typically 2 to 4, preferably 2 (such that the reactant is a cyclooctadiene), $R^{A1}$ and $R^A$ are as defined above for structure (A), and $R^{C1}$, $R^{C2}$, $R^{C3}$, $R^{C4}$, $R^{C5}$, and $R^{C6}$ are defined as for $R^{B1}$ through $R^{B6}$. In this case, it is preferred that $R^{c3}$ and $R^{C4}$ be non-hydrogen substituents, in which case the second olefinic moiety is tetrasubstituted. Examples of monocyclic diene reactants include, without limitation, 1,3-cyclopentadiene, 1,3-cyclohexadiene, 1,4-cyclohexadiene, 5-ethyl-1,3-cyclohexadiene, 1,3-cycloheptadiene, cyclohexadiene, 1,5-cyclooctadiene, 1,3-cyclooctadiene, and substituted analogs thereof. Triene reactants are analogous to the diene structure (C), and will generally contain at least one methylene linkage between any two olefinic segments.

Bicyclic and polycyclic olefins encompassed by structure (A) may be generally represented by the structure (D)

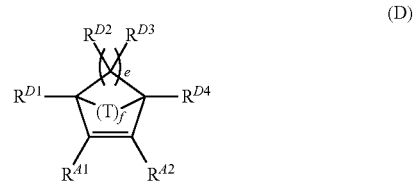

(D)

wherein $R^{A1}$ and $R^{A2}$ are as defined above for structure (A), $R^{D1}$, $R^{D2}$, $R^{D3}$, and $R^{D4}$ are as defined for $R^{B1}$ through $R^{B6}$, e is an integer in the range of 1 to 8 (typically 2 to 4) f is generally 1 or 2; T is lower alkylene or alkenylene (generally substituted or unsubstituted methyl or ethyl), $CHR^{G1}$, $C(R^{G1})_2$, O, S, N—$R^{G1}$, P—$R^{G1}$, O=P—$R^{G1}$, $Si(R^{G1})_2$, B—$R^{G1}$, or As—$R^{G1}$ where $R^{G1}$ is alkyl, alkenyl, cycloalkyl, cycloalkenyl, aryl, alkaryl, aralkyl, or alkoxy. Furthermore, any of the $R^{D1}$, $R^{D2}$, $R^{D3}$, and $R^{D4}$ moieties can be linked to any of the other $R^{D1}$, $R^{D2}$, $R^{D3}$, and $R^{D4}$ moieties to provide a substituted or unsubstituted alicyclic group containing 4 to 30 ring carbon atoms or a substituted or unsubstituted aryl group containing 6 to 18 ring carbon atoms or combinations thereof and the linkage may include heteroatoms or functional groups, e.g., the linkage may include without limitation an ether, ester, thioether, amino, alkylamino, imino, or anhydride moiety. The cyclic group can be monocyclic, bicyclic, or polycyclic. When unsaturated the cyclic group can contain monounsaturation or multiunsaturation, with monounsaturated cyclic groups being preferred. When substituted, the rings contain monosubstitution or multisubstitution wherein the substituents are independently selected from hydrogen, hydrocarbyl, substituted hydrocarbyl, heteroatom-containing hydrocarbyl, substituted heteroatom-containing hydrocarbyl, —$(Z^*)_n$-Fn where n is zero or 1, $Z^*$ and Fn are as defined previously, and functional groups (Fn) provided above.

Cyclic olefins encompassed by structure (D) are in the norbornene family. As used herein, norbornene means any compound that includes at least one norbornene or substituted norbornene moiety, including without limitation norbornene, substituted norbornene(s), norbornadiene, substituted norbornadiene(s), polycyclic norbornenes, and substituted polycyclic norbornene(s). Norbornenes within this group may be generally represented by the structure (E)

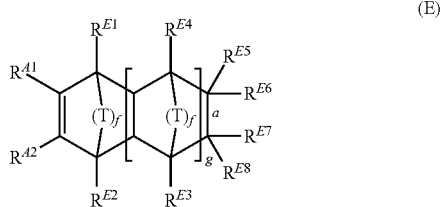

(E)

wherein $R^{41}$ and $R^{42}$ are as defined above for structure (A), T is as defined above for structure (D), $R^{E1}$, $R^{E2}$, $R^{E3}$, $R^{E4}$, $R^{E5}$, $R^{E6}$, $R^{E7}$, and $R^{E8}$ are as defined for $R^{B1}$ through $R^{B6}$, and "a" represents a single bond or a double bond, f is generally 1 or 2, "g" is an integer from 0 to 5, and when "a" is a double bond one of $R^{E5}$, $R^{E6}$ and one of $R^{E7}$, $R^{E8}$ is not present.

Furthermore, any of the $R^{E5}$, $R^{E6}$, $R^{E7}$, and $R^{E8}$ moieties can be linked to any of the other $R^{E5}$, $R^{E6}$, $R^{E7}$, and $R^{E8}$ moieties to provide a substituted or unsubstituted alicyclic group containing 4 to 30 ring carbon atoms or a substituted or unsubstituted aryl group containing 6 to 18 ring carbon atoms or combinations thereof and the linkage may include heteroatoms or functional groups, e.g., the linkage may include without limitation an ether, ester, thioether, amino, alkylamino, imino, or anhydride moiety. The cyclic group can be monocyclic, bicyclic, or polycyclic. When unsaturated the cyclic group can contain monounsaturation or multiunsaturation, with monounsaturated cyclic groups being preferred. When substituted, the rings contain monosubstitution or multisubstitution wherein the substituents are independently selected from hydrogen, hydrocarbyl, substituted hydrocarbyl, heteroatom-containing hydrocarbyl, substituted heteroatom-containing hydrocarbyl, —$(Z^*)_n$-Fn where n is zero or 1, $Z^*$ and Fn are as defined previously, and functional groups (Fn) provided above.

More preferred cyclic olefins possessing at least one norbornene moiety have the structure (F):

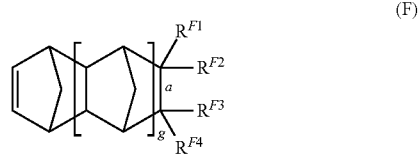

(F)

wherein $R^{F1}$, $R^{F2}$, $R^{F3}$, and $R^{F4}$ are as defined for $R^{B1}$ through $R^{B6}$, and "a" represents a single bond or a double bond, "g" is an integer from 0 to 5, and when "a" is a double bond one of $R^{F1}$, $R^{F2}$ and one of $R^{F3}$, $R^{F4}$ is not present.

Furthermore, any of the $R^{F1}$, $R^{F2}$, $R^{F3}$, and $R^{F4}$ moieties can be linked to any of the other $R^{F1}$, $R^{F2}$, $R^{F3}$, and $R^{F4}$ moieties to provide a substituted or unsubstituted alicyclic group containing 4 to 30 ring carbon atoms or a substituted or unsubstituted aryl group containing 6 to 18 ring carbon atoms or combinations thereof and the linkage may include heteroatoms or functional groups, e.g., the linkage may include without limitation an ether, ester, thioether, amino, alkylamino, imino, or anhydride moiety. The alicyclic group can be monocyclic, bicyclic, or polycyclic. When unsaturated the cyclic group can contain monounsaturation or multiunsaturation, with monounsaturated cyclic groups being preferred. When substituted, the rings contain monosubstitution or multisubstitution wherein the substituents are independently selected from hydrogen, hydrocarbyl, substituted hydrocarbyl, heteroatom-containing hydrocarbyl, substituted heteroatom-containing hydrocarbyl, —$(Z^*)_n$-Fn where n is zero or 1, $Z^*$ and Fn are as defined previously, and functional groups (Fn) provided above One route for the preparation of hydrocarbyl substituted and functionally substituted norbornenes employs the Diels-Alder cycloaddition reaction in which cyclopentadiene or substituted cyclopentadiene is reacted with a suitable dienophile at elevated temperatures to form the substituted norbornene adduct generally shown by the following reaction Scheme 1:

SCHEME 1

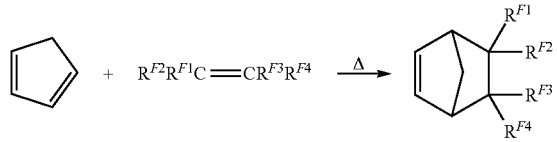

wherein $R^{F1}$ to $R^{F4}$ are as previously defined for structure (F).

Other norbornene adducts can be prepared by the thermal pyrolysis of dicyclopentadiene in the presence of a suitable dienophile. The reaction proceeds by the initial pyrolysis of dicyclopentadiene to cyclopentadiene followed by the Diels-Alder cycloaddition of cyclopentadiene and the dienophile to give the adduct shown below in Scheme 2:

SCHEME 2

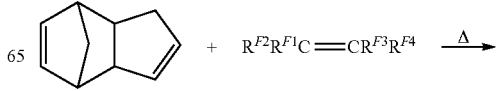

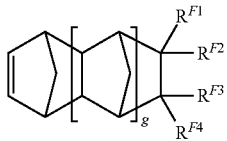

wherein "g" is an integer from 0 to 5, and $R^{F1}$ to $R^{F4}$ are as previously defined for structure (F).

Norbornadiene and higher Diels-Alder adducts thereof similarly can be prepared by the thermal reaction of cyclopentadiene and dicyclopentadiene in the presence of an acetylenic reactant as shown below in Scheme 3:

SCHEME 3

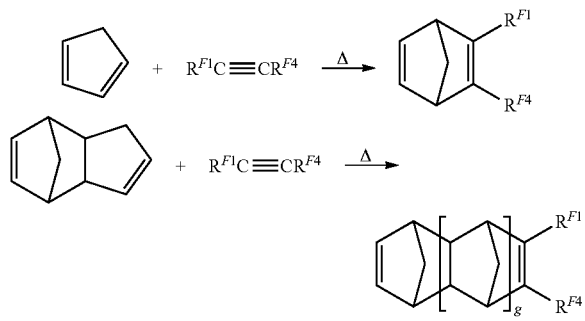

wherein "g" is an integer from 0 to 5, $R^{F1}$ and $R^{F4}$ are as previously defined for structure (F)

Examples of bicyclic and polycyclic olefins thus include, without limitation, dicyclopentadiene (DCPD); trimer and other higher order oligomers of cyclopentadiene including without limitation tricyclopentadiene (cyclopentadiene trimer), cyclopentadiene tetramer, and cyclopentadiene pentamer; ethylidenenorbornene; dicyclohexadiene; norbornene; 5-methyl-2-norbornene; 5-ethyl-2-norbornene; 5-isobutyl-2-norbornene; 5,6-dimethyl-2-norbornene; 5-phenylnorbornene; 5-benzylnorbornene; 5-acetylnorbornene; 5-methoxycarbonylnorbornene; 5-ethyoxycarbonyl-1-norbornene; 5-methyl-5-methoxy-carbonylnorbornene; 5-cyanonorbornene; 5,5,6-trimethyl-2-norbornene; cyclo-hexenylnorbornene; endo, exo-5,6-dimethoxynorbornene; endo, endo-5,6-dimethoxynorbornene; endo, exo-5,6-dimethoxycarbonylnorbornene; endo,endo-5,6-dimethoxycarbonylnorbornene; 2,3-dimethoxynorbornene; norbornadiene; tricycloundecene; tetracyclododecene; 8-methyltetracyclododecene; 8-ethyltetracyclododecene; 8-methoxycarbonyltetracyclododecene; 8-methyl-8-tetracyclododecene; 8-cyanotetracyclododecene; pentacyclopentadecene; pentacyclohexadecene; and the like, and their structural isomers, stereoisomers, and mixtures thereof. Additional examples of bicyclic and polycyclic olefins include, without limitation, $C_2$-$C_{12}$ hydrocarbyl substituted norbornenes such as 5-butyl-2-norbornene, 5-hexyl-2-norbornene, 5-octyl-2-norbornene, 5-decyl-2-norbornene, 5-dodecyl-2-norbornene, 5-vinyl-2-norbornene, 5-ethylidene-2-norbornene, 5-isopropenyl-2-norbornene, 5-propenyl-2-norbornene, and 5-butenyl-2-norbornene, and the like.

Preferred cyclic olefins include $C_5$ to $C_{24}$ unsaturated hydrocarbons. Also preferred are $C_5$ to $C_{24}$ cyclic hydrocarbons that contain one or more (typically 2 to 12) heteroatoms such as O, N, S, or P. For example, crown ether cyclic olefins may include numerous O heteroatoms throughout the cycle, and these are within the scope of the invention. In addition, preferred cyclic olefins are $C_5$ to $C_{24}$ hydrocarbons that contain one or more (typically 2 or 3) olefins. For example, the cyclic olefin may be mono-, di-, or tri-unsaturated. Examples of cyclic olefins include without limitation cyclooctene, cyclododecene, and (c,t,t)-1,5,9-cyclododecatriene.

The cyclic olefins may also comprise multiple (typically 2 or 3) rings. For example, the cyclic olefin may be mono-, di-, or tri-cyclic. When the cyclic olefin comprises more than one ring, the rings may or may not be fused. Preferred examples of cyclic olefins that comprise multiple rings include norbornene, dicyclopentadiene, tricyclopentadiene, and 5-ethylidene-2-norbornene.

The cyclic olefin may also be substituted, for example, a $C_5$ to $C_{24}$ cyclic hydrocarbon wherein one or more (typically 2, 3, 4, or 5) of the hydrogens are replaced with non-hydrogen substituents. Suitable non-hydrogen substituents may be chosen from the substituents described hereinabove. For example, functionalized cyclic olefins, i.e., $C_5$ to $C_{24}$ cyclic hydrocarbons wherein one or more (typically 2, 3, 4, or 5) of the hydrogens are replaced with functional groups, are within the scope of the invention. Suitable functional groups may be chosen from the functional groups described hereinabove. For example, a cyclic olefin functionalized with an alcohol group may be used to prepare a telechelic polymer comprising pendent alcohol groups. Functional groups on the cyclic olefin may be protected in cases where the functional group interferes with the metathesis catalyst, and any of the protecting groups commonly used in the art may be employed. Acceptable protecting groups may be found, for example, in Greene et al., Protective Groups in Organic Synthesis, 3rd Ed. (New York: Wiley, 1999). Examples of functionalized cyclic olefins include without limitation 2-hydroxymethyl-5-norbornene, 2-[(2-hydroxyethyl)carboxylate]-5-norbornene, cydecanol, 5-n-hexyl-2-norbornene, 5-n-butyl-2-norbornene.

Cyclic olefins incorporating any combination of the abovementioned features (i.e., heteroatoms, substituents, multiple olefins, multiple rings) are suitable for the methods disclosed herein. Additionally, cyclic olefins incorporating any combination of the abovementioned features (i.e., heteroatoms, substituents, multiple olefins, multiple rings) are suitable for the invention disclosed herein.

The cyclic olefins useful in the methods disclosed herein may be strained or unstrained. It will be appreciated that the amount of ring strain varies for each cyclic olefin compound, and depends upon a number of factors including the size of the ring, the presence and identity of substituents, and the presence of multiple rings. Ring strain is one factor in determining the reactivity of a molecule towards ring-opening olefin metathesis reactions. Highly strained cyclic olefins, such as certain bicyclic compounds, readily undergo ring opening reactions with olefin metathesis catalysts. Less strained cyclic olefins, such as certain unsubstituted hydrocarbon monocyclic olefins, are generally less reactive. In some cases, ring opening reactions of relatively unstrained (and therefore relatively unreactive) cyclic olefins may become possible when performed in the presence of the olefinic compounds disclosed herein. Additionally, cyclic olefins useful in the invention disclosed herein may be strained or unstrained.

The resin compositions of the present invention may comprise a plurality of cyclic olefins. A plurality of cyclic olefins may be used to prepare metathesis polymers from the olefinic compound. For example, two cyclic olefins selected from the cyclic olefins described hereinabove may be employed in order to form metathesis products that incorporate both cyclic olefins. Where two or more cyclic olefins are used, one example of a second cyclic olefin is a cyclic alkenol, i.e., a $C_5$-$C_{24}$ cyclic hydrocarbon wherein at least one of the hydrogen substituents is replaced with an alcohol or protected alcohol moiety to yield a functionalized cyclic olefin.

The use of a plurality of cyclic olefins, and in particular when at least one of the cyclic olefins is functionalized, allows for further control over the positioning of functional groups within the products. For example, the density of cross-linking points can be controlled in polymers and macromonomers prepared using the methods disclosed herein. Control over the quantity and density of substituents and functional groups also allows for control over the physical properties (e.g., melting point, tensile strength, glass transition temperature, etc.) of the products. Control over these and other properties is possible for reactions using only a single cyclic olefin, but it will be appreciated that the use of a plurality of cyclic olefins further enhances the range of possible metathesis products and polymers formed.

More preferred cyclic olefins include dicyclopentadiene; tricyclopentadiene; dicyclohexadiene; norbornene; 5-methyl-2-norbornene; 5-ethyl-2-norbornene; 5-isobutyl-2-norbornene; 5,6-dimethyl-2-norbornene; 5-phenylnorbornene; 5-benzylnorbornene; 5-acetylnorbornene; 5-methoxycarbonylnorbornene; 5-ethoxycarbonyl-1-norbornene; 5-methyl-5-methoxy-carbonylnorbornene; 5-cyanonorbornene; 5,5,6-trimethyl-2-norbornene; cyclo-hexenylnorbornene; endo, exo-5,6-dimethoxynorbornene; endo, endo-5,6-dimethoxynorbornene; endo, exo-5-6-dimethoxycarbonylnorbornene; endo, endo-5,6-dimethoxycarbonylnorbornene; 2,3-dimethoxynorbornene; norbornadiene; tricycloundecene; tetracyclododecene; 8-methyltetracyclododecene; 8-ethyl-tetracyclododecene; 8-methoxycarbonyltetracyclododecene; 8-methyl-8-tetracyclo-dodecene; 8-cyanotetracyclododecene; pentacyclopentadecene; pentacyclohexadecene; higher order oligomers of cyclopentadiene such as cyclopentadiene tetramer, cyclopentadiene pentamer, and the like; and $C_2$-$C_{12}$ hydrocarbyl substituted norbornenes such as 5-butyl-2-norbornene; 5-hexyl-2-norbornene; 5-octyl-2-norbornene; 5-decyl-2-norbornene; 5-dodecyl-2-norbornene; 5-vinyl-2-norbornene; 5-ethylidene-2-norbornene; 5-isopropenyl-2-norbornene; 5-propenyl-2-norbornene; and 5-butenyl-2-norbornene, and the like. Even more preferred cyclic olefins include dicyclopentadiene, tricyclopentadiene, and higher order oligomers of cyclopentadiene, such as cyclopentadiene tetramer, cyclopentadiene pentamer, and the like, tetracyclododecene, norbornene, and $C_2$-$C_{12}$ hydrocarbyl substituted norbornenes, such as 5-butyl-2-norbornene, 5-hexyl-2-norbornene, 5-octyl-2-norbornene, 5-decyl-2-norbornene, 5-dodecyl-2-norbornene, 5-vinyl-2-norbornene, 5-ethylidene-2-norbornene, 5-isopropenyl-2-norbornene, 5-propenyl-2-norbornene, 5-butenyl-2-norbornene, and the like. Examples of cyclic olefins include dicyclopentadiene, tricyclopentadiene, and higher order oligomers of cyclopentadiene, such as cyclopentadiene tetramer, cyclopentadiene pentamer, and the like, including structural isomers and/or stereoisomers, any and all of which are suitable for use in the present invention. Examples of cyclic olefins include dicyclopentadiene, tricyclopentadiene, and tetracyclopentadiene, including structural isomers and/or stereoisomers, any and all of which are suitable for use in the present invention. Examples of cyclic olefins include dicyclopentadiene and tricyclopentadiene, including structural isomers and/or stereoisomers, any and all of which are suitable for use in the present invention.

Metal Carbene Olefin Metathesis Catalysts

A metal carbene olefin metathesis catalyst that may be used in the invention disclosed herein, is preferably a Group 8 transition metal complex having the structure of formula (I)

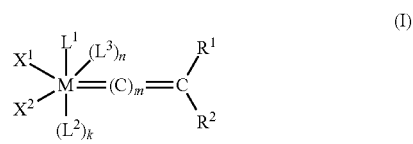

in which:
M is a Group 8 transition metal;
$L^1$, $L^2$, and $L^3$ are neutral electron donor ligands;
n is 0 or 1, such that $L^3$ may or may not be present;
m is 0, 1, or 2;
k is 0 or 1;
$X^1$ and $X^2$ are anionic ligands; and
$R^1$ and $R^2$ are independently selected from hydrogen, hydrocarbyl, substituted hydrocarbyl, heteroatom-containing hydrocarbyl, substituted heteroatom-containing hydrocarbyl, and functional groups,
wherein any two or more of $X^1$, $X^2$, $L^1$, $L^2$, $L^3$, $R^1$, and $R^2$ can be taken together to form one or more cyclic groups, and further wherein any one or more of $X^1$, $X^2$, $L^1$, $L^2$, $L^3$, $R^1$, and $R^2$ may be attached to a support.

Additionally, in formula (I), one or both of $R^1$ and $R^2$ may have the structure —$(W)_n$—$U^+V^-$, in which W is selected from hydrocarbylene, substituted hydrocarbylene, heteroatom-containing hydrocarbylene, or substituted heteroatom-containing hydrocarbylene; U is a positively charged Group 15 or Group 16 element substituted with hydrogen, hydrocarbyl, substituted hydrocarbyl, heteroatom-containing hydrocarbyl, or substituted heteroatom-containing hydrocarbyl; V is a negatively charged counterion; and n is zero or 1. Furthermore, $R^1$ and $R^2$ may be taken together to form an indenylidene moiety, preferably phenylindenylidene.

Preferred metal carbene olefin metathesis catalysts contain Ru or Os as the Group 8 transition metal, with Ru particularly preferred.

Numerous embodiments of the metal carbene olefin metathesis catalysts useful in the reactions disclosed herein are described in more detail infra. For the sake of convenience, the metal carbene olefin metathesis catalysts are described in groups, but it should be emphasized that these groups are not meant to be limiting in any way. That is, any of the metal carbene olefin metathesis catalysts useful in the invention may fit the description of more than one of the groups described herein. Moreover, more than one metal carbene olefin metathesis catalyst may be used in the invention herein.

A first group of metal carbene olefin metathesis catalysts, then, are commonly referred to as First Generation Grubbs-type catalysts, and have the structure of formula (I). For the first group of metal carbene olefin metathesis catalysts, M is a Group 8 transition metal, m is 0, 1, or 2, and n, $X^1$, $X^2$, $L^1$, $L^2$, $L^3$, $R^1$, and $R^2$ are described as follows.

For the first group of metal carbene olefin metathesis catalysts, n is 0, and $L^1$ and $L^2$ are independently selected from phosphine, sulfonated phosphine, phosphite, phosphinite, phosphonite, arsine, stibine, ether, (including cyclic ethers), amine, amide, imine, sulfoxide, carboxyl, nitrosyl, pyridine, substituted pyridine, imidazole, substituted imidazole, pyrazine, substituted pyrazine and thioether. Exemplary ligands are trisubstituted phosphines. Preferred trisubstituted phosphines are of the formula $PR^{H1}R^{H2}R^{H3}$, where $R^{H1}$, $R^{H2}$, and $R^{H3}$ are each independently substituted or unsubstituted aryl or $C_1$-$C_{10}$ alkyl, particularly primary alkyl, secondary alkyl, or cycloalkyl. In the most preferred, $L^1$ and $L^2$ are independently selected from the group consisting of trimethylphosphine ($PMe_3$), triethylphosphine ($PEt_3$), tri-n-butylphosphine ($PBu_3$), tri(ortho-tolyl)phosphine (P-o-tolyl$_3$), tri-tert-butvlphosphine (P-tert-Bu$_3$), tricyclopentylphosphine (PCyclopentyl$_3$), tricyclohexylphosphine ($PCy_3$), triisopropylphosphine (P-i-Pr$_3$), trioctylphosphine (POct$_3$), triisobutylphosphine, (P-i-Bu$_3$), triphenylphosphine ($PPh_3$), tri(pentafluorophenyl)phosphine ($P(C_6F_5)_3$), methyldiphenylphosphine ($PMePh_2$), dimethylphenylphosphine ($PMe_2Ph$), and diethylphenylphosphine ($PEt_2Ph$). Alternatively, $L^1$ and $L^2$ may be independently selected from phosphabicycloalkane (e.g., monosubstituted 9-phosphabicyclo-[3.3.1]nonane, or monosubstituted 9-phosphabicyclo[4.2.1]nonane] such as cyclohexylphoban, isopropylphoban, ethylphoban, methylphoban, butylphoban, pentylphoban and the like).

$X^1$ and $X^2$ are anionic ligands, and may be the same or different, or are linked together to form a cyclic group, typically although not necessarily a five- to eight-membered ring. In preferred embodiments, $X^1$ and $X^2$ are each independently hydrogen, halide, or one of the following groups: $C_1$-$C_{20}$ alkyl, $C_5$-$C_{24}$ aryl, $C_1$-$C_{20}$ alkoxy, $C_5$-$C_{24}$ aryloxy, $C_2$-$C_{20}$ alkoxycarbonyl, $C_6$-$C_{24}$ aryloxycarbonyl, $C_2$-$C_{24}$ acyl, $C_2$-$C_{24}$ acyloxy, $C_1$-$C_{20}$ alkylsulfonato, $C_5$-$C_{24}$ arylsulfonato, $C_1$-$C_{20}$ alkylsulfanyl, $C_5$-$C_{24}$ arylsulfanyl, $C_1$-$C_{20}$ alkylsulfinyl, $NO_3$, —N=C=O, —N=C=S, or $C_5$-$C_{24}$ arylsulfinyl. Optionally, $X^1$ and $X^2$ may be substituted with one or more moieties selected from $C_1$-$C_{12}$ alkyl, $C_1$-$C_{12}$ alkoxy, $C_5$-$C_{24}$ aryl, and halide, which may, in turn, with the exception of halide, be further substituted with one or more groups selected from halide, $C_1$-$C_6$ alkyl, $C_1$-$C_6$ alkoxy, and phenyl. In more preferred embodiments, $X^1$ and $X^2$ are halide, benzoate, $C_2$-$C_6$ acyl, $C_2$-$C_6$ alkoxycarbonyl, $C_1$-$C_6$ alkyl, phenoxy, $C_1$-$C_6$ alkoxy, $C_1$-$C_6$ alkylsulfanyl, aryl, or $C_1$-$C_6$ alkylsulfonyl. In even more preferred embodiments, $X^1$ and $X^2$ are each halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethane-sulfonate. In the most preferred embodiments, $X^1$ and $X^2$ are each chloride.

$R^1$ and $R^2$ are independently selected from hydrogen, hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), heteroatom-containing hydrocarbyl (e.g., heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and substituted heteroatom-containing hydrocarbyl (e.g., substituted heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and functional groups. $R^1$ and $R^2$ may also be linked to form a cyclic group, which may be aliphatic or aromatic, and may contain substituents and/or heteroatoms. Generally, such a cyclic group will contain 4 to 12, preferably 5, 6, 7, or 8 ring atoms.

In preferred metal carbene olefin metathesis catalysts, $R^1$ is hydrogen and $R^2$ is selected from $C_1$-$C_{20}$ alkyl, $C_2$-$C_{20}$ alkenyl, and $C_5$-$C_{24}$ aryl, more preferably $C_1$-$C_6$ alkyl, $C_2$-$C_6$ alkenyl, and $C_5$-$C_{14}$ aryl. Still more preferably, $R^2$ is phenyl, vinyl, methyl, isopropyl, or t-butyl, optionally substituted with one or more moieties selected from $C_1$-$C_6$ alkyl, $C_1$-$C_6$ alkoxy, phenyl, and a functional group Fn as defined earlier herein. Most preferably, $R^2$ is phenyl or vinyl substituted with one or more moieties selected from methyl, ethyl, chloro, bromo, iodo, fluoro, nitro, dimethylamino, methyl, methoxy, and phenyl. Optimally, $R^2$ is phenyl or —CH=C(CH$_3$)$_2$.

Any two or more (typically two, three, or four) of $X^1$, $X^2$, $L^1$, $L^2$, $L^3$, $R^1$, and $R^2$ can be taken together to form a cyclic group, including bidentate or multidentate ligands, as disclosed, for example, in U.S. Pat. No. 5,312,940, the disclosure of which is incorporated herein by reference. When any of $X^1$, $X^2$, $L^1$, $L^2$, $L^3$, $R^1$, and $R^2$ are linked to form cyclic groups, those cyclic groups may contain 4 to 12, preferably 4, 5, 6, 7 or 8 atoms, or may comprise two or three of such rings, which may be either fused or linked. The cyclic groups may be aliphatic or aromatic, and may be heteroatom-containing and/or substituted. The cyclic group may, in some cases, form a bidentate ligand or a tridentate ligand. Examples of bidentate ligands include, but are not limited to, bisphosphines, dialkoxides, alkyldiketonates, and aryldiketonates.

A second group of metal carbene olefin metathesis catalysts, commonly referred to as Second Generation Grubbs-type catalysts, have the structure of formula (I), wherein $L^1$ is a carbene ligand having the structure of formula (II)

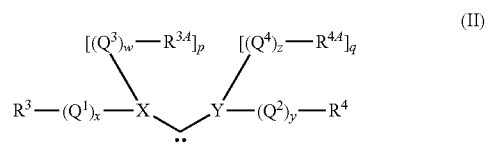

(II)

such that the complex may have the structure of formula (III)

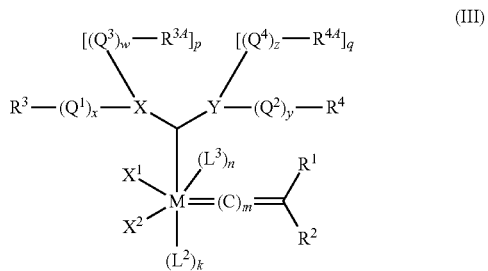

(III)

wherein M, m, n, $X^1$, $X^2$, $L^2$, $L^3$, $R^1$, and $R^2$ are as defined for the first group of metal carbene olefin metathesis catalysts, and the remaining substituents are as follows;

X and Y are heteroatoms typically selected from N, O, S, and P. Since O and S are divalent, p is necessarily zero when X is O or S, q is necessarily zero when Y is O or S, and k is zero or 1. However, when X is N or P, then p is 1, and when Y is N or P, then q is 1. In a preferred embodiment, both X and Y are N;

$Q^1$, $Q^2$, $Q^3$, and $Q^4$ are linkers, e.g., hydrocarbylene (including substituted hydrocarbylene, heteroatom-containing hydrocarbylene, and substituted heteroatom-containing hydrocarbylene, such as substituted and/or heteroatom-containing alkylene) or —(CO)—, and w, x, y, and z are independently zero or 1, meaning that each linker is optional. Preferably, w, x, y, and z are all zero. Further, two or more substituents on adjacent atoms within $Q^1$, $Q^2$, $Q^3$, and $Q^4$ may be linked to form an additional cyclic group; and $R^3$, $R^{3A}$, $R^4$, and $R^{4A}$ are independently selected from hydrogen, hydrocarbyl, substituted hydrocarbyl, heteroatom-containing hydrocarbyl, and substituted heteroatom-containing hydrocarbyl. In addition, X and Y may be independently selected from carbon and one of the heteroatoms mentioned above, preferably no more than one of X or Y is carbon. Also, $L^2$ and $L^3$ may be taken together to form a single bindentate electron-donating heterocyclic ligand. Furthermore, $R^1$ and $R^2$ may be taken together to form an indenylidene moiety, preferably phenylindenylidene. Moreover, $X^1$, $X^2$, $L^2$, $L^3$, X and Y may be further coordinated to boron or to a carboxylate.

In addition, any two or more of $X^1$, $X^2$, $L^1$, $L^2$, $L^3$, $R^1$, $R^2$, $R^3$, $R^{3A}$, $R^{4A}$, $Q^1$, $Q^2$, $Q^3$, and $Q^4$ can be taken together to form a cyclic group, and any one or more of $X^1$, $X^2$, $L^2$, $L^3$, $Q^1$, $Q^2$, $Q^3$, $Q^4$, $R^1$, $R^2$, $R^3$, $R^{3A}$, $R^4$, and $R^{4A}$ may be attached to a support. Any two or more of $X^1$, $X^2$, L, $L^2$, $L^3$, $R^1$, $R^2$, $R^3$, $R^{3A}$, $R^4$, and $R^{4A}$ can also be taken to be -A-Fn, wherein "A" is a divalent hydrocarbon moiety selected from alkylene and arylalkylene, wherein the alkyl portion of the alkylene and arylalkylene groups can be linear or branched, saturated or unsaturated, cyclic or acyclic, and substituted or unsubstituted, wherein the aryl portion of the of arylalkylene can be substituted or unsubstituted, and wherein hetero atoms and/or functional groups may be present in either the aryl or the alkyl portions of the alkylene and arylalkylene groups, and Fn is a functional group, or together to form a cyclic group, and any one or more of $X^1$, $X^2$, $L^2$, $L^3$, $Q^1$, $Q^2$, $Q^3$, $Q^4$, $R^1$, $R^2$, $R^3$, $R^{3A}$, $R^4$, and $R^{4A}$ may be attached to a support.

A particular class of carbene ligands having the structure of formula (II), where $R^{3A}$ and $R^{4A}$ are linked to form a cyclic group and at least one of X or Y is a nitrogen, or at least one of $Q^3$ or $Q^4$ is a heteroatom-containing hydrocarbylene or substituted heteroatom-containing hydrocarbylene, where at least one heteroatom is a nitrogen, are commonly referred to as N-heterocyclic carbene (NHC) ligands. Preferably, $R^{3A}$ and $R^{4A}$ are linked to form a cyclic group so that the carbene ligand has the structure of formula (IV)

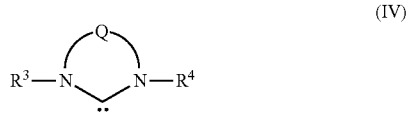

(IV)

wherein $R^3$ and $R^4$ are as defined for the second group of metal carbene olefin metathesis catalysts above, with preferably at least one of $R^3$ and $R^4$, and more preferably both $R^3$ and $R^4$, being alicyclic or aromatic of one to about five rings, and optionally containing one or more heteroatoms and/or substituents. Q is a linker, typically a hydrocarbylene linker, including substituted hydrocarbylene, heteroatom-containing hydrocarbylene, and substituted heteroatom-containing hydrocarbylene linkers, wherein two or more substituents on adjacent atoms within Q may also be linked to form an additional cyclic structure, which may be similarly substituted to provide a fused polycyclic structure of two to about five cyclic groups. Q is often, although not necessarily, a two-atom linkage or a three-atom linkage.

Examples of N-heterocyclic carbene (NHC) ligands and acyclic diaminocarbene ligands suitable as $L^1$ thus include, but are not limited to, the following where DIPP or DiPP is diisopropylphenyl and Mes is 2,4,6-trimethylphenyl:

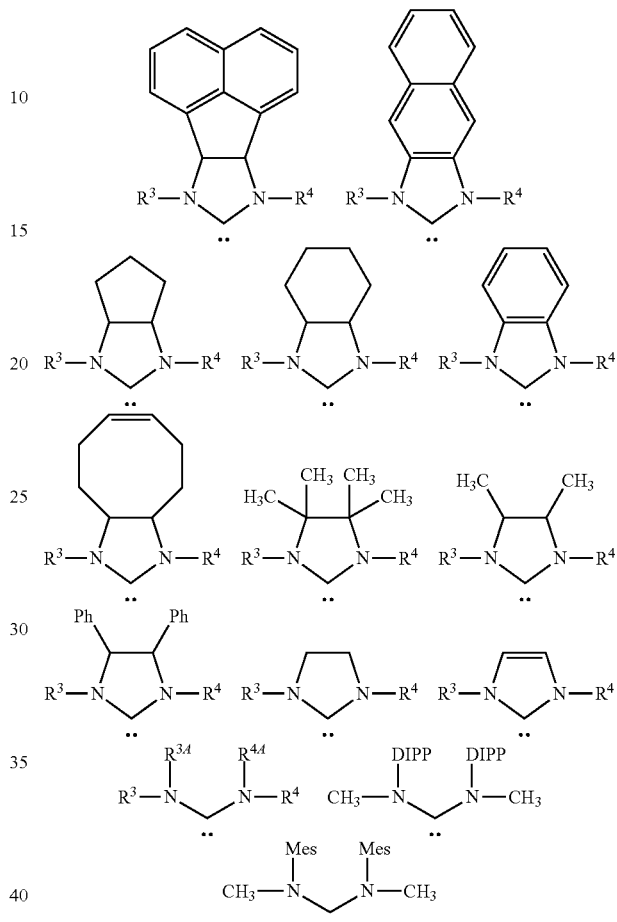

Additional examples of N-heterocyclic carbene (NHC) ligands and acyclic diaminocarbene ligands suitable as $L^1$ thus include, but are not limited to the following:

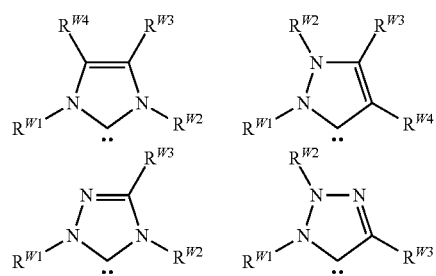

wherein $R^{W1}$, $R^{W2}$, $R^{W3}$, $R^{W4}$ are independently hydrogen, unsubstituted hydrocarbyl, substituted hydrocarbyl, or heteroatom containing hydrocarbyl, and where one or both of $R^{W3}$ and $R^{W4}$ may be in independently selected from halogen, nitro, amido, carboxyl, alkoxy, aryloxy, sulfonyl, carbonyl, thio, or nitroso groups.

Additional examples of N-heterocyclic carbene (NHC) ligands suitable as $L^1$ are further described in U.S. Pat. Nos.

7,378,528; 7,652,145; 7,294,717; 6,787,620; 6,635,768; and 6,552,139, the contents of each are incorporated herein by reference.

Additionally, thermally activated N-Heterocyclic Carbene Precursors as disclosed in U.S. Pat. No. 6,838,489, the contents of which are incorporated herein by reference, may also be used with the present invention.

When M is ruthenium, then, the preferred complexes have the structure of formula (V)

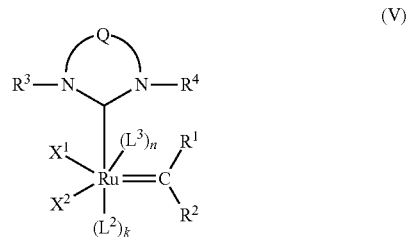

(V)

In a more preferred embodiment, Q is a two-atom linkage having the structure —$CR^{11}R^{12}$—$CR^{13}R^{14}$— or —$CR^{11}$=$CR^{13}$—, preferably —$CR^{11}R^{12}$—$CR^{13}R^{14}$—, wherein $R^{11}$, $R^{12}$, $R^{13}$, and $R^{14}$ are independently selected from hydrogen, hydrocarbyl, substituted hydrocarbyl, heteroatom-containing hydrocarbyl, substituted heteroatom-containing hydrocarbyl, and functional groups. Examples of functional groups here include without limitation carboxyl, $C_1$-$C_{20}$ alkoxy, $C_5$-$C_{24}$ aryloxy, $C_2$-$C_{20}$ alkoxycarbonyl, $C_5$-$C_{24}$ alkoxycarbonyl, $C_2$-$C_{24}$ acyloxy, $C_1$-$C_{20}$ alkylthio, $C_5$-$C_{24}$ arylthio, $C_1$-$C_{20}$ alkylsulfonyl, and $C_1$-$C_{20}$ alkylsulfinyl, optionally substituted with one or more moieties selected from $C_1$-$C_{12}$ alkyl, $C_1$-$C_{12}$ alkoxy, $C_5$-$C_{14}$ aryl, hydroxyl, sulfhydryl, formyl, and halide. $R^{11}$, $R^{12}$, $R^{13}$, and $R^{14}$ are preferably independently selected from hydrogen, $C_1$-$C_{12}$ alkyl, substituted $C_1$-$C_{12}$ alkyl, $C_1$-$C_{12}$ heteroalkyl, substituted $C_1$-$C_{12}$ heteroalkyl, phenyl, and substituted phenyl. Alternatively, any two of $R^{11}$, $R^{12}$, $R^{13}$, and $R^4$ may be linked together to form a substituted or unsubstituted, saturated or unsaturated ring structure, e.g., a $C_4$-$C_{12}$ alicyclic group or a $C_5$ or $C_6$ aryl group, which may itself be substituted, e.g., with linked or fused alicyclic or aromatic groups, or with other substituents. In one further aspect, any one or more of $R^{11}$, $R^{12}$, $R^{13}$, and $R^{14}$ comprises one or more of the linkers. Additionally, $R^3$ and $R^4$ may be unsubstituted phenyl or phenyl substituted with one or more substituents selected from $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, or halide. Furthermore, $X^1$ and $X^2$ may be halogen.

When $R^3$ and $R^4$ are aromatic, they are typically although not necessarily composed of one or two aromatic rings, which may or may not be substituted, e.g., $R^3$ and $R^4$ may be phenyl, substituted phenyl, biphenyl, substituted biphenyl, or the like. In one preferred embodiment, $R^3$ and $R^4$ are the same and are each unsubstituted phenyl or phenyl substituted with up to three substituents selected from $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, or halide. Preferably, any substituents present are hydrogen, $C_1$-$C_{12}$ alkyl, $C_1$-$C_{12}$ alkoxy, $C_5$-$C_{14}$ aryl, substituted $C_5$-$C_{14}$ aryl, or halide. As an example, $R^3$ and $R^4$ are mesityl (i.e., Mes as defined herein).

In a third group of metal carbene olefin metathesis catalysts having the structure of formula (I), M, m, n, $X^1$, $X^2$, $R^1$, and $R^2$ are as defined for the first group of metal carbene olefin metathesis catalysts, $L^1$ is a strongly coordinating neutral electron donor ligand such as any of those described for the first and second group of metal carbene olefin metathesis catalysts, and $L^2$ and $L^3$ are weakly coordinating neutral electron donor ligands in the form of optionally substituted heterocyclic groups. Again, n is zero or 1, such that $L^3$ may or may not be present. Generally, in the third group of metal carbene olefin metathesis catalysts, $L^2$ and $L^3$ are optionally substituted five- or six-membered monocyclic groups containing 1 to 4, preferably 1 to 3, most preferably 1 to 2 heteroatoms, or are optionally substituted bicyclic or polycyclic structures composed of 2 to 5 such five- or six-membered monocyclic groups. If the heterocyclic group is substituted, it should not be substituted on a coordinating heteroatom, and any one cyclic moiety within a heterocyclic group will generally not be substituted with more than 3 substituents.

For the third group of metal carbene olefin metathesis catalysts, examples of $L^2$ and $L^3$ include, without limitation, heterocycles containing nitrogen, sulfur, oxygen, or a mixture thereof.

Examples of nitrogen-containing heterocycles appropriate for $L^2$ and $L^3$ include pyridine, bipyridine, pyridazine, pyrimidine, bipyridamine, pyrazine, 1,3,5-triazine, 1,2,4-triazine, 1,2,3-triazine, pyrrole, 2H-pyrrole, 3H-pyrrole, pyrazole, 2H-imidazole, 1,2,3-triazole, 1,2,4-triazole, indole, 3H-indole, 1H-isoindole, cyclopenta(b)pyridine, indazole, quinoline, bisquinoline, isoquinoline, biisoquinoline, cinnoline, quinazoline, naphthyridine, piperidine, piperazine, pyrrolidine, pyrazolidine, quinuclidine, imidazolidine, picolylamine, purine, benzimidazole, bisimidazole, phenazine, acridine, and carbazole. Additionally, the nitrogen-containing heterocycles may be optionally substituted on a non-coordinating heteroatom with a non-hydrogen substitutent.

Examples of sulfur-containing heterocycles appropriate for $L^2$ and $L^3$ include thiophene, 1,2-dithiole, 1,3-dithiole, thiepin, benzo(b)thiophene, benzo(c)thiophene, thionaphthene, dibenzothiophene, 2H-thiopyran, 4H-thiopyran, and thioanthrene.

Examples of oxygen-containing heterocycles appropriate for $L^2$ and $L^3$ include 2H-pyran, 4H-pyran, 2-pyrone, 4-pyrone, 1,2-dioxin, 1,3-dioxin, oxepin, furan, 2H-1-benzopyran, coumarin, coumarone, chromene, chroman-4-one, isochromen-1-one, isochromen-3-one, xanthene, tetrahydrofuran, 1,4-dioxan, and dibenzofuran.

Examples of mixed heterocycles appropriate for $L^2$ and $L^3$ include isoxazole, oxazole, thiazole, isothiazole, 1,2,3-oxadiazole, 1,2,4-oxadiazole, 1,3,4-oxadiazole, 1,2,3,4-oxatriazole, 1,2,3,5-oxatriazole, 3H-1,2,3-dioxazole, 3H-1,2-oxathiole, 1,3-oxathiole, 4H-1,2-oxazine, 2H-1,3-oxazine, 1,4-oxazine, 1,2,5-oxathiazine, o-isooxazine, phenoxazine, phenothiazine, pyrano[3,4-b]pyrrole, indoxazine, benzoxazole, anthranil, and morpholine.

Preferred $L^2$ and $L^3$ ligands are aromatic nitrogen-containing and oxygen-containing heterocycles, and particularly preferred $L^2$ and $L^3$ ligands are monocyclic N-heteroaryl ligands that are optionally substituted with 1 to 3, preferably 1 or 2, substituents. Specific examples of particularly preferred $L^2$ and $L^3$ ligands are pyridine and substituted pyridines, such as 3-bromopyridine, 4-bromopyridine, 3,5-dibromopyridine, 2,4,6-tribromopyridine, 2,6-dibromopyridine, 3-chloropyridine, 4-chloropyridine, 3,5-dichloropyridine, 2,4,6-trichloropyridine, 2,6- dichloropyridine, 4-iodopyridine, 3,5-diiodopyridine, 3,5-dibromo-4-methylpyridine, 3,5-dichloro-4-methylpyridine, 3,5-dimethyl-4-bromopyridine, 3,5-dimethylpyridine, 4-methylpyridine, 3,5-diisopropylpyridine, 2,4,6-trimethylpyridine, 2,4,6-triisopropylpyridine, 4-(tert-butyl)pyridine, 4-phenylpyridine, 3,5-diphenylpyridine, 3,5-dichloro-4-phenylpyridine, and the like.

In general, any substituents present on $L^2$ and/or $L^3$ are selected from halo, $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, substituted $C_5$-$C_{24}$ heteroaryl, $C_6$-$C_{24}$ alkaryl, substituted $C_6$-$C_{24}$ alkaryl, $C_6$-$C_{24}$ heteroalkaryl, substituted $C_6$-$C_{24}$ heteroalkaryl, $C_6$-$C_{24}$ aralkyl, substituted $C_6$-$C_{24}$ aralkyl, $C_6$-$C_{24}$ heteroaralkyl, substituted $C_6$-$C_{24}$ heteroaralkyl, and functional groups, with suitable functional groups including, without limitation, $C_1$-$C_{20}$ alkoxy, $C_5$-$C_{24}$ aryloxy, $C_2$-$C_{20}$ alkylcarbonyl, $C_6$-$C_{24}$ arylcarbonyl, $C_2$-$C_{20}$ alkylcarbonyloxy, $C_6$-$C_{24}$ arylcarbonyloxy, $C_2$-$C_{20}$ alkoxycarbonyl, $C_6$-$C_{24}$ aryloxycarbonyl, halocarbonyl, $C_2$-$C_{20}$ alkylcarbonato, $C_6$-$C_{24}$ arylcarbonato, carboxy, carboxylato, carbamoyl, mono-($C_1$-$C_{20}$ alkyl)-substituted carbamoyl, di-($C_1$-$C_{20}$ alkyl)-substituted carbamoyl, di-N—($C_1$-$C_{20}$ alkyl), N—($C_5$-$C_{24}$ aryl)-substituted carbamoyl, mono-($C_5$-$C_{24}$ aryl)-substituted carbamoyl, di-($C_6$-$C_{24}$ aryl)-substituted carbamoyl, thiocarbamoyl, mono-($C_1$-$C_{20}$ alkyl)-substituted thiocarbamoyl, di-($C_1$-$C_{20}$ alkyl)-substituted thiocarbamoyl, di-N—($C_1$-$C_{20}$ alkyl)-N—($C_6$-$C_{24}$ aryl)-substituted thiocarbamoyl, mono-($C_6$-$C_{24}$ aryl)-substituted thiocarbamoyl, di-($C_6$-$C_{24}$ aryl)-substituted thiocarbamoyl, carbamido, formyl, thioformyl, amino, mono-($C_1$-$C_{20}$ alkyl)-substituted amino, di-($C_1$-$C_{20}$ alkyl)-substituted amino, mono-($C_5$-$C_{24}$ aryl)-substituted amino, di-($C_5$-$C_{24}$ aryl)-substituted amino, di-N—($C_1$-$C_{20}$ alkyl),N—($C_5$-$C_{24}$ aryl)-substituted amino, $C_2$-$C_{20}$ alkylamido, $C_6$-$C_{24}$ arylamido, imino, $C_1$-$C_{20}$ alkylimino, $C_5$-$C_{24}$ arylimino, nitro, and nitroso. In addition, two adjacent substituents may be taken together to form a ring, generally a five- or six-membered alicyclic or aryl ring, optionally containing 1 to 3 heteroatoms and 1 to 3 substituents as above.

Preferred substituents on $L^2$ and $L^3$ include, without limitation, halo, $C_1$-$C_{12}$ alkyl, substituted $C_1$-$C_{12}$ alkyl, $C_1$-$C_{12}$ heteroalkyl, substituted $C_1$-$C_{12}$ heteroalkyl, $C_5$-$C_{14}$ aryl, substituted $C_5$-$C_{14}$ aryl, $C_5$-$C_{14}$ heteroaryl, substituted $C_5$-$C_{14}$ heteroaryl, $C_6$-$C_{16}$ alkaryl, substituted $C_6$-$C_{16}$ alkaryl, $C_6$-$C_{16}$ heteroalkaryl, substituted $C_6$-$C_{16}$ heteroalkaryl, $C_6$-$C_{16}$ aralkyl, substituted $C_6$-$C_{16}$ aralkyl, $C_6$-$C_{16}$ heteroaralkyl, substituted $C_6$-$C_{16}$ heteroaralkyl, $C_1$-$C_{12}$ alkoxy, $C_5$-$C_{14}$ aryloxy, $C_2$-$C_{12}$ alkylcarbonyl, $C_6$-$C_{14}$ arylcarbonyl, $C_2$-$C_{12}$ alkylcarbonyloxy, $C_6$-$C_{16}$ arylcarbonyloxy, $C_2$-$C_{12}$ alkoxycarbonyl, $C_6$-$C_{14}$ aryloxycarbonyl, halocarbonyl, formyl, amino, mono-($C_1$-$C_{12}$ alkyl)-substituted amino, di-($C_1$-$C_{12}$ alkyl)-substituted amino, mono-($C_5$-$C_{14}$ aryl)-substituted amino, di-($C_5$-$C_4$ aryl)-substituted amino, and nitro.

Of the foregoing, the most preferred substituents are halo, $C_1$-$C_6$ alkyl, $C_1$-$C_6$ haloalkyl, $C_1$-$C_6$ alkoxy, phenyl, substituted phenyl, formyl, N,N-di($C_1$-$C_6$ alkyl)amino, nitro, and nitrogen heterocycles as described above (including, for example, pyrrolidine, piperidine, piperazine, pyrazine, pyrimidine, pyridine, pyridazine, etc.).

In certain embodiments, $L^2$ and $L^3$ may also be taken together to form a bidentate or multidentate ligand containing two or more, generally two, coordinating heteroatoms such as N, O, S, or P, with preferred such ligands being diimine ligands of the Brookhart type. One representative bidentate ligand has the structure of formula (VI)

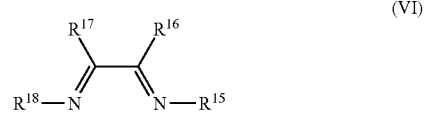

(VI)

wherein $R^{15}$, $R^{16}$, $R^{17}$, and $R^{18}$ hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, or $C_6$-$C_{24}$ aralkyl), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, or $C_6$-$C_{24}$ aralkyl), heteroatom-containing hydrocarbyl (e.g., $C_1$-$C_{20}$ heteroalkyl, $C_5$-$C_{24}$ heteroaryl, heteroatom-containing $C_6$-$C_{24}$ aralkyl, or heteroatom-containing $C_6$-$C_{24}$ alkaryl), or substituted heteroatom-containing hydrocarbyl (e.g., substituted $C_1$-$C_{20}$ heteroalkyl, $C_5$-$C_{24}$ heteroaryl, heteroatom-containing $C_6$-$C_{24}$ aralkyl, or heteroatom-containing $C_6$-$C_{24}$ alkaryl), or (1) $R^{15}$ and $R^{16}$, (2) $R^{17}$ and $R^{18}$, (3) $R^{16}$ and $R^{17}$, or (4) both $R^{15}$ and $R^{16}$, and $R^{17}$ and $R^{18}$, may be taken together to form a ring, i.e., an N-heterocycle. Preferred cyclic groups in such a case are five- and six-membered rings, typically aromatic rings.

In a fourth group of metal carbene olefin metathesis catalysts that have the structure of formula (I), two of the substituents are taken together to form a bidentate ligand or a tridentate ligand. Examples of bidentate ligands include, but are not limited to, bisphosphines, dialkoxides, alkyldiketonates, and aryldiketonates. Specific examples include —P(Ph)$_2$CH$_2$CH$_2$P(Ph)$_2$-, —As(Ph)$_2$CH$_2$CH$_2$As(Ph$_2$)-, —P(Ph)$_2$CH$_2$CH$_2$C(CF$_3$)$_2$O—, binaphtholate dianions, pinacolate dianions, —P(CH$_3$)$_2$(CH$_2$)$_2$P(CH$_3$)$_2$—, and —OC(CH$_3$)$_2$(CH$_3$)$_2$CO—. Preferred bidentate ligands are —P(Ph)$_2$ CH$_2$CH$_2$P(Ph)$_2$- and —P(CH$_3$)$_2$(CH$_2$)$_2$P(CH$_3$)$_2$. Tridentate ligands include, but are not limited to, (CH$_3$)$_2$NCH$_2$CH$_2$P(Ph)CH$_2$CH$_2$N(CH$_3$)$_2$. Other preferred tridentate ligands are those in which any three of $X^1$, $X^2$, $L^1$, $L^2$, $L^3$, $R^1$, and $R^2$ (e.g., $X^1$, $L^1$, and $L^2$) are taken together to be cyclopentadienyl, indenyl, or fluorenyl, each optionally substituted with $C_2$-$C_{20}$ alkenyl, $C_2$-$C_{20}$ alkynyl, $C_1$-$C_{20}$ alkyl, $C_5$-$C_{20}$ aryl, $C_1$-$C_{20}$ alkoxy, $C_2$-$C_{20}$ alkenyloxy, $C_2$-$C_{20}$ alkynyloxy, $C_5$-$C_{20}$ aryloxy, $C_2$-$C_{20}$ alkoxycarbonyl, $C_1$-$C_{20}$ alkylthio, $C_1$-$C_{20}$ alkylsulfonyl, or $C_1$-$C_{20}$ alkylsulfinyl, each of which may be further substituted with $C_1$-$C_6$ alkyl, halide, $C_1$-$C_6$ alkoxy or with a phenyl group optionally substituted with halide, $C_1$-$C_6$ alkyl, or $C_1$-$C_6$ alkoxy. More preferably, in compounds of this type, X, $L^1$, and $L^2$ are taken together to be cyclopentadienyl or indenyl, each optionally substituted with vinyl, $C_1$-$C_{10}$ alkyl, $C_5$-$C_{20}$ aryl, $C_1$-$C_{10}$ carboxylate, $C_2$-$C_{10}$ alkoxycarbonyl, $C_1$-$C_{10}$ alkoxy, or $C_5$-$C_{20}$ aryloxy, each optionally substituted with $C_1$-$C_6$ alkyl, halide, $C_1$-$C_6$ alkoxy or with a phenyl group optionally substituted with halide, $C_1$-$C_6$ alkyl or $C_1$-$C_6$ alkoxy. Most preferably, X, $L^1$ and $L^2$ may be taken together to be cyclopentadienyl, optionally substituted with vinyl, hydrogen, methyl, or phenyl. Tetradentate ligands include, but are not limited to O$_2$C(CH$_2$)$_2$P(Ph)(CH$_2$)$_2$P(Ph)(CH$_2$)$_2$CO$_2$, phthalocyanines, and porphyrins.

Complexes wherein Y is coordinated to the metal are examples of a fifth group of metal carbene olefin metathesis catalysts, and are commonly called "Grubbs-Hoveyda" catalysts. Grubbs-Hoveyda metathesis-active metal carbene complexes may be described by the formula (VII)

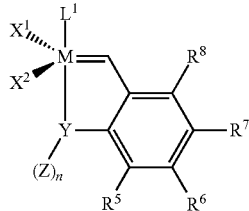

(VII)

wherein,

M is a Group 8 transition metal, particularly Ru or Os, or, more particularly, Ru;

$X^1$, $X^2$, and $L^1$ are as previously defined herein for the first and second groups of metal carbene olefin metathesis catalysts;

Y is a heteroatom selected from N, O, S, and P; preferably Y is O or N;

$R^5$, $R^6$, $R^7$, and $R^8$ are each, independently, selected from the group consisting of hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, borate, or -A-Fn, wherein "A" and Fn have been defined above; and any combination of Y, Z, $R^5$, $R^6$, $R^7$, and $R^8$ can be linked to form one or more cyclic groups;

n is 0, 1, or 2, such that n is 1 for the divalent heteroatoms O or S, and n is 2 for the trivalent heteroatoms N or P; and Z is a group selected from hydrogen, alkyl, aryl, functionalized alkyl, functionalized aryl where the functional group(s) may independently be one or more or the following: alkoxy, aryloxy, halogen, carboxylic acid, ketone, aldehyde, nitrate, cyano, isocyanate, hydroxyl, ester, ether, amine, imine, amide, trifluoroamide, sulfide, disulfide, carbamate, silane, siloxane, phosphine, phosphate, or borate; methyl, isopropyl, sec-butyl, t-butyl, neopentyl, benzyl, phenyl and trimethylsilyl; and wherein any combination or combinations of $X^1$, $X^2$, $L^1$, Y, Z, $R^5$, $R^6$, $R^7$, and $R^8$ may be linked to a support. Additionally, $R^5$, $R^6$, $R^7$, $R^8$, and Z may independently be thioisocyanate, cyanato, or thiocyanato.

Examples of complexes comprising Grubbs-Hoveyda ligands suitable in the invention include:

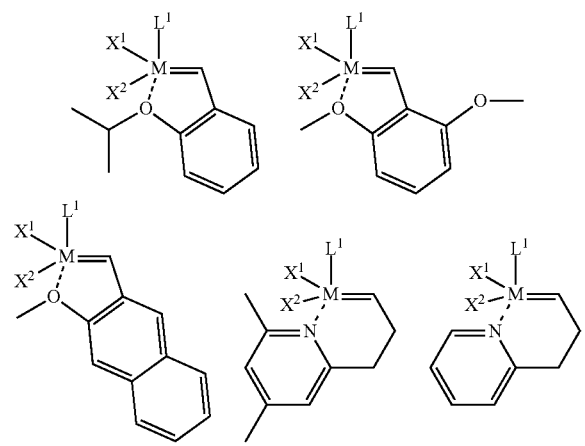

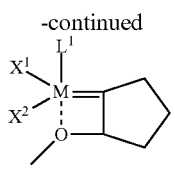

wherein, $L^1$, $X^1$, $X^2$, and M are as described for any of the other groups of metal carbene olefin metathesis catalysts. Suitable chelating carbenes and carbene precursors are further described by Pederson et al. (U.S. Pat. Nos. 7,026,495 and 6,620,955, the disclosures of both of which are incorporated herein by reference) and Hoveyda et al. (U.S. Pat. No. 6,921,735 and WO0214376, the disclosures of both of which are incorporated herein by reference).

Other useful complexes include structures wherein $L^2$ and $R^2$ according to formulae (I), (III), or (V) are linked, such as styrenic compounds that also include a functional group for attachment to a support. Examples in which the functional group is a trialkoxysilyl functionalized moiety include, but are not limited to, the following:

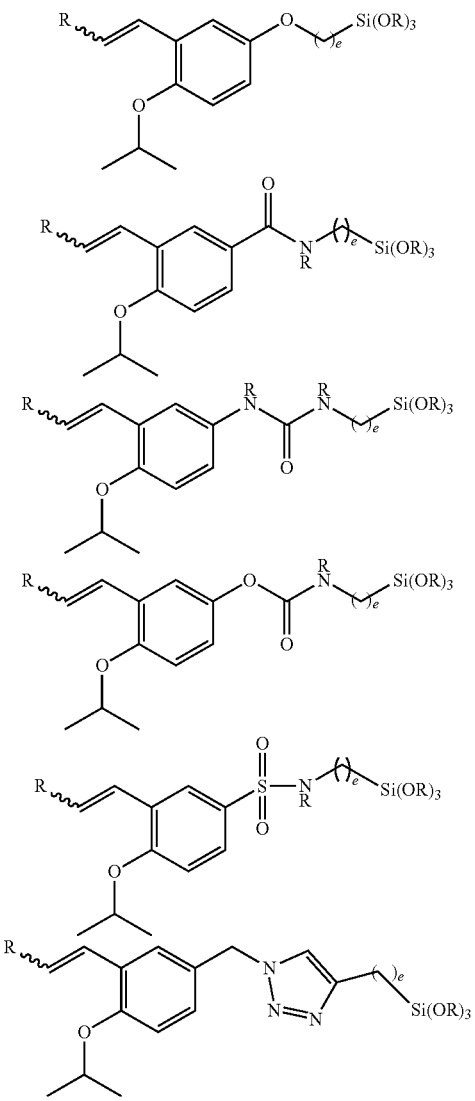

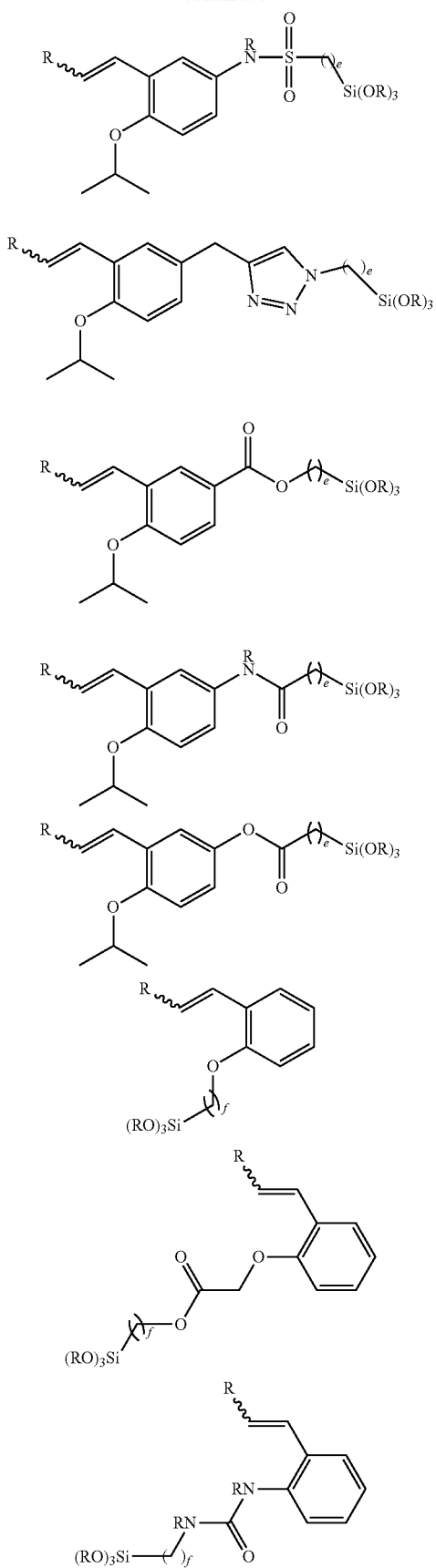

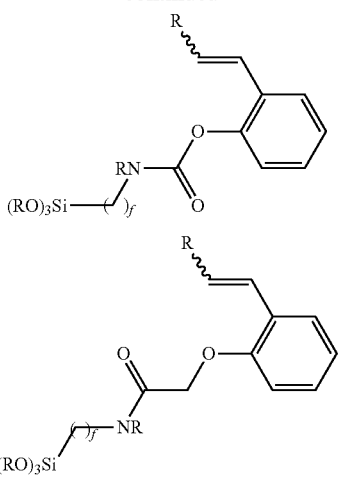

Further examples of complexes having linked ligands include those having linkages between a neutral NHC ligand and an anionic ligand, a neutral NHC ligand and an alkylidine ligand, a neutral NHC ligand and an $L^2$ ligand, a neutral NHC ligand and an $L^3$ ligand, an anionic ligand and an alkylidine ligand, and any combination thereof. While the possible structures are too numerous to list herein, some suitable structures based on formula (III) include:

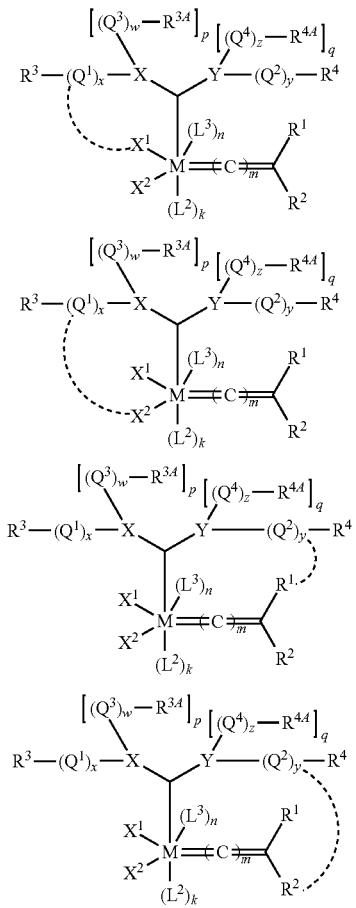

-continued

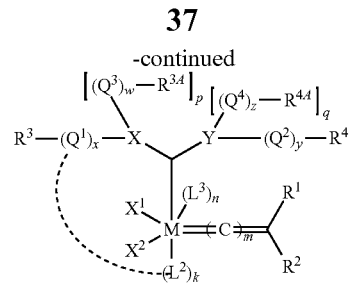

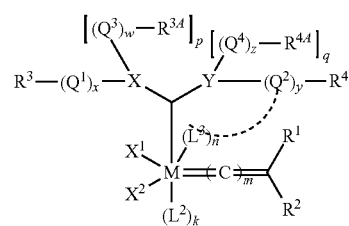

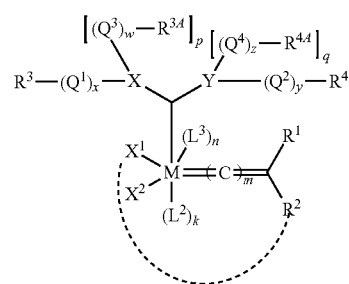

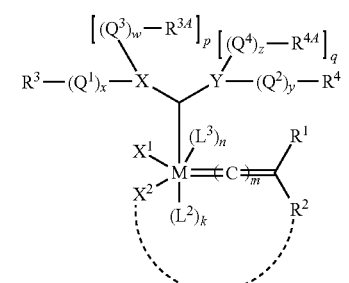

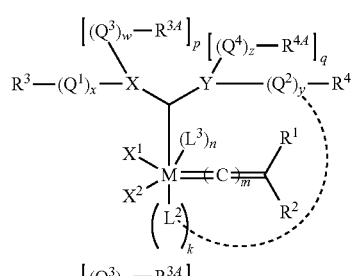

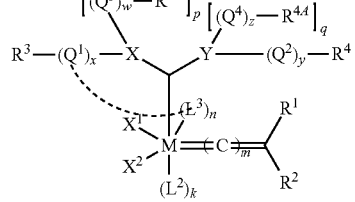

-continued

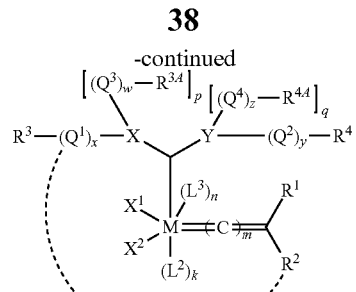

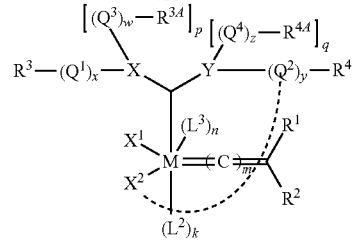

In addition to the metal carbene olefin metathesis catalysts that have the structure of formula (I), as described above, other transition metal carbene complexes include, but are not limited to:

neutral ruthenium or osmium metal carbene complexes containing metal centers that are formally in the +2 oxidation state, have an electron count of 16, are penta-coordinated, and are of the general formula (IX);

neutral ruthenium or osmium metal carbene complexes containing metal centers that are formally in the +2 oxidation state, have an electron count of 18, are hexa-coordinated, and are of the general formula (X);

cationic ruthenium or osmium metal carbene complexes containing metal centers that are formally in the +2 oxidation state, have an electron count of 14, are tetra-coordinated, and are of the general formula (XI); and cationic ruthenium or osmium metal carbene complexes containing metal centers that are formally in the +2 oxidation state, have an electron count of 14 or 16, are tetra-coordinated or penta-coordinated, respectively, and are of the general formula (XII)

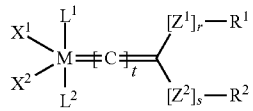 (IX)

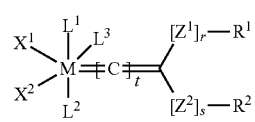 (X)

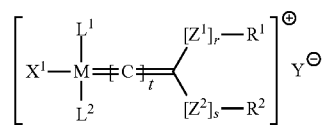 (XI)

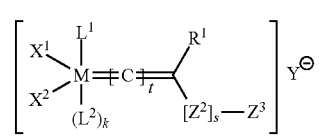 (XII)

wherein:

M, $X^1$, $X^2$, $L^1$, $L^2$, $L^3$, $R^1$, and $R^2$ are as defined for any of the previously defined four groups of metal carbene olefin metathesis catalysts;

r and s are independently zero or 1;

t is an integer in the range of zero to 5;

k is an integer in the range of zero to 1;

Y is any non-coordinating anion (e.g., a halide ion, $BF_4^-$, etc.);

$Z^1$ and $Z^2$ are independently selected from —O—, —S—, —$NR^2$—, —$PR^2$—, —P(=O)$R^2$—, —P($OR^2$)—, —P(=O)($OR^2$)—, —C(=O)—, —C(=O)O—, —OC(=O)—, —OC(=O)O—, —S(=O)—, —S(=O)$_2$—, and an optionally substituted and/or optionally heteroatom-containing $C_1$-$C_{20}$ hydrocarbylene linkage;

$Z^3$ is any cationic moiety such as —P($R^2$)$_3^+$ or —N($R^2$)$_3^+$; and any two or more of $X^1$, $X^2$, $L^1$, $L^2$, $L^3$, $Z^1$, $Z^2$, $Z^3$, $R^1$, and $R^2$ may be taken together to form a cyclic group, e.g., a multidentate ligand, and wherein any one or more of $X^1$, $X^2$, $L^1$, $L^2$, $L^3$, $Z^1$, $Z^2$, $Z^3$, $R^1$, and $R^2$ may be attached to a support.

Additionally, another group of metal carbene olefin metathesis catalysts that may be used in the invention disclosed herein, is a Group 8 transition metal complex having the structure of formula (XIII):

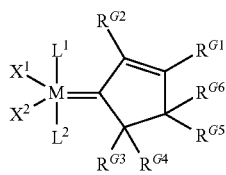

(XIII)

wherein M is a Group 8 transition metal, particularly ruthenium or osmium, or more particularly, ruthenium;

$X^1$, $X^2$, $L^1$ and $L^2$ are as defined for the first and second groups of metal carbene olefin metathesis catalysts defined above; and $R^{G1}$, $R^{G2}$, $R^{G3}$, $R^{G4}$, $R^{G5}$, and $R^{G6}$ are each independently selected from the group consisting of hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, thioisocyanate, cyanato, thiocyanato, hydroxyl, ester, ether, thioether, amine, alkylamine, imine, amide, halogen-substituted amide, trifluoroamide, sulfide, disulfide, sulfonate, carbamate, silane, siloxane, phosphine, phosphate, borate, or -A-Fn, wherein "A" is a divalent hydrocarbon moiety selected from alkylene and arylalkylene, wherein the alkyl portion of the alkylene and arylalkylene groups can be linear or branched, saturated or unsaturated, cyclic or acyclic, and substituted or unsubstituted, wherein the aryl portion of the arylalkylene can be substituted or unsubstituted, and wherein hetero atoms and/or functional groups may be present in either the aryl or the alkyl portions of the alkylene and arylalkylene groups, and Fn is a functional group, or any one or more of the $R^{G1}$, $R^{G2}$, $R^{G3}$, $R^{G4}$, $R^{G5}$, and $R^{G6}$ may be linked together to form a cyclic group, or any one or more of the $R^{G1}$, $R^{G2}$, $R^{G3}$, $R^{G4}$, $R^{G5}$, and $R^{G6}$ may be attached to a support.

Additionally, one preferred embodiment of the Group 8 transition metal complex of formula XIII is a Group 8 transition metal complex of formula (XIV):

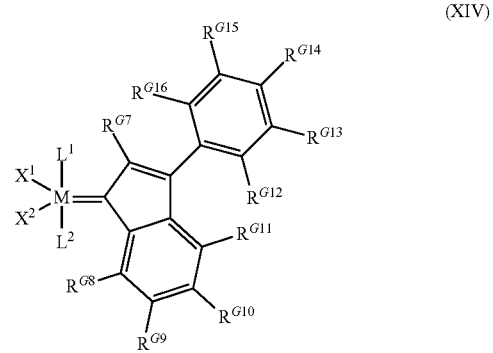

(XIV)

wherein M, $X^1$, $X^2$, $L^1$, $L^2$ are as defined above for Group 8 transition metal complex of formula XIII; and $R^{G7}$, $R^{G8}$, $R^{G9}$, $R^{G10}$, $R^{G11}$, $R^{G12}$, $R^{G13}$, $R^{G14}$, $R^{G15}$ and $R^{G16}$ are as defined above for $R^{G1}$, $R^{G2}$, $R^{G3}$, $R^{G4}$, $R^{G5}$, and $R^{G6}$ for Group 8 transition metal complex of formula XIII or any one or more of the $R^{G7}$, $R^{G8}$, $R^{G9}$, $R^{G10}$, $R^{G11}$, $R^{G12}$, $R^{G13}$, $R^{G14}$, $R^{G15}$ and $R^{G16}$ may be linked together to form a cyclic group, or any one or more of the $R^{G7}$, $R^{G8}$, $R^{G9}$, $R^{G10}$, $R^{G11}$, $R^{G12}$, $R^{G13}$, $R^{G14}$, $R^{G15}$ and $R^{G16}$ may be attached to a support.

Additionally, another preferred embodiment of the Group 8 transition metal complex of formula XIII is a Group 8 transition metal complex of formula (XV):

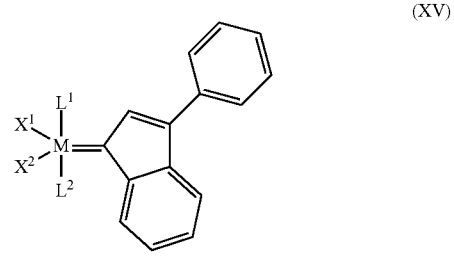

(XV)

wherein M, $X^1$, $X^2$, $L^1$, $L^2$ are as defined above for Group 8 transition metal complex of formula XIII.

Additionally, another group of metal carbene olefin metathesis catalysts that may be used in the invention disclosed herein, is a Group 8 transition metal complex comprising a Schiff base ligand having the structure of formula (XVI):

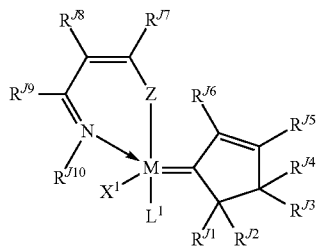

(XVI)

wherein M is a Group 8 transition metal, particularly ruthenium or osmium, or more particularly, ruthenium;

$X^1$ and $L^1$ are as defined for the first and second groups of metal carbene olefin metathesis catalysts defined above;

Z is selected from the group consisting of oxygen, sulfur, selenium, $NR^{J11}$, $PR^{J11}$, $AsR^{J11}$, and $SbR^{J11}$; and $R^{J1}$, $R^{J2}$, $R^{J3}$, $R^{J4}$, $R^{J5}$, $R^{J6}$, $R^{J7}$, $R^{J8}$, $R^{J9}$, $R^{J10}$, and $R^{J11}$ are each independently selected from the group consisting of hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, thioisocyanate, cyanato, thiocyanato, hydroxyl, ester, ether, thioether, amine, alkylamine, imine, amide, halogen-substituted amide, trifluoroamide, sulfide, disulfide, sulfonate, carbamate, silane, siloxane, phosphine, phosphate, borate, or -A-Fn, wherein "A" is a divalent hydrocarbon moiety selected from alkylene and arylalkylene, wherein the alkyl portion of the alkylene and arylalkylene groups can be linear or branched, saturated or unsaturated, cyclic or acyclic, and substituted or unsubstituted, wherein the aryl portion of the arylalkylene can be substituted or unsubstituted, and wherein hetero atoms and/or functional groups may be present in either the aryl or the alkyl portions of the alkylene and arylalkylene groups, and Fn is a functional group, or any one or more of the $R^{J1}$, $R^{J2}$, $R^{J3}$, $R^{J4}$, R, $R^{J6}$, $R^{J7}$, $R^{J8}$, $R^{J9}$, $R^{J10}$, and $R^{J11}$ may be linked together to form a cyclic group, or any one or more of the $R^{J1}$, $R^{J2}$, $R^{J3}$, $R^{J4}$, $R^{J5}$, $R^{J6}$, $R^{J7}$, $R^{J8}$, $R^{J9}$, $R^{J10}$, and $R^{J11}$ may be attached to a support.

Additionally, one preferred embodiment of the Group 8 transition metal complex of formula (XVI) is a Group 8 transition metal complex comprising a Schiff base ligand having the structure of formula (XVII):

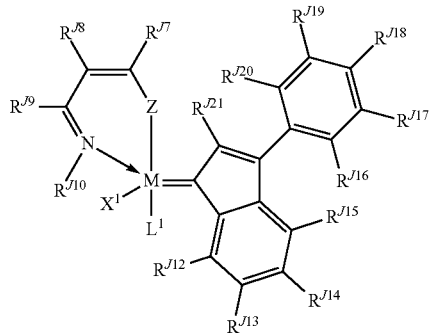

(XVII)

wherein M, $X^1$, $L^1$, Z, $R^{J7}$, $R^{J8}$, $R^{J9}$, $R^{J10}$, and $R^{J11}$ are as defined above for Group 8 transition metal complex of formula XVI; and $R^{J12}$, $R^{J13}$, $R^{J14}$, $R^{J15}$, $R^{J16}$, $R^{J17}$, $R^{J18}$, $R^{J19}$, $R^{J20}$, and $R^{J21}$ are as defined above for $R^{J1}$, $R^{J2}$, $R^{J3}$, $R^{J4}$, $R^{J5}$, and $R^{J6}$ for Group 8 transition metal complex of formula XVI, or any one or more of the $R^{J7}$, $R^{J8}$, $R^{J9}$, $R^{J10}$, $R^{J11}$, $R^{J12}$, $R^{J13}$, $R^{J14}$, $R^{J15}$, $R^{J16}$, $R^{J17}$, $R^{J18}$, $R^{J19}$, $R^{J20}$, and $R^{J21}$ may be linked together to form a cyclic group, or any one or more of the $R^{J7}$, $R^{J8}$, $R^{J9}$, $R^{J10}$, $R^{J11}$, $R^{J12}$, $R^{J13}$, $R^{J14}$, $R^{J15}$, $R^{J16}$, $R^{J17}$, $R^{J18}$, $R^{J19}$, $R^{J20}$, and $R^{J21}$ may be attached to a support.

Additionally, another preferred embodiment of the Group 8 transition metal complex of formula (XVI) is a Group 8 transition metal complex comprising a Schiff base ligand having the structure of formula (XVIII):

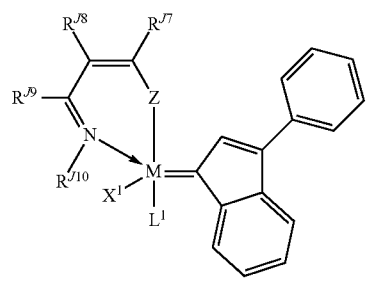

(XVIII)

wherein M, $X^1$, $L^1$, Z, $R^{J7}$, $R^{J8}$, $R^{J9}$, $R^{J10}$, and $R^{J11}$ are as defined above for Group 8 transition metal complex of formula (XVI).

Additionally, another group of metal carbene olefin metathesis catalysts that may be used in the invention disclosed herein, is a Group 8 transition metal complex comprising a Schiff base ligand having the structure of formula (XIX):

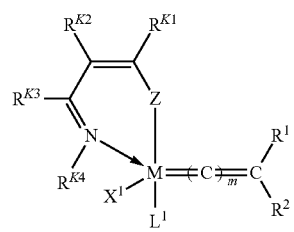

(XIX)

wherein M is a Group 8 transition metal, particularly ruthenium or osmium, or more particularly, ruthenium;

$X^1$, $L^1$, $R^1$, and $R^2$ are as defined for the first and second groups of metal carbene olefin metathesis catalysts defined above;

Z is selected from the group consisting of oxygen, sulfur, selenium, $NR^{K5}$, $PR^{K5}$, $AsR^{K5}$, and $SbR^{K5}$;

m is 0, 1, or 2; and $R^{K1}$, $R^{K2}$, $R^{K3}$, $R^{K4}$, and $R^{K5}$ are each independently selected from the group consisting of hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, thioisocyanate, cyanato, thiocyanato, hydroxyl, ester, ether, thioether, amine, alkylamine, imine, amide, halogen-substituted amide, trifluoroamide, sulfide, disulfide, sulfonate, carbamate, silane, siloxane, phosphine, phosphate, borate, or -A-Fn, wherein "A" is a divalent hydrocarbon moiety selected from alkylene and arylalkylene, wherein the alkyl portion of the alkylene and arylalkylene groups can be linear or branched, saturated or unsaturated, cyclic or acyclic, and substituted or unsubstituted, wherein the aryl portion of the arylalkylene can be substituted or unsubstituted, and wherein hetero atoms and/or functional groups may be present in either the aryl or the alkyl portions of the alkylene and arylalkylene groups, and Fn is a functional group, or any one or more of the $R^{K1}$, $R^{K2}$, $R^{K3}$, $R^{K4}$, and $R^{K5}$ may be linked together to form a cyclic group, or any one or more of the $R^{K1}$, $R^{K2}$, $R^{K3}$, $R^{K4}$, and $R^{K5}$ may be attached to a support.

In addition, metal carbene olefin metathesis catalysts of formulas (XVI) to (XIX) may be optionally contacted with an activating compound, where at least partial cleavage of a bond between the Group 8 transition metal and at least one Schiff base ligand occurs, wherein the activating compound is either a metal or silicon compound selected from the group consisting of copper (I) halides; zinc compounds of the formula $Zn(R^{Y1})_2$, wherein $R^{Y1}$ is halogen, $C_1$-$C_7$ alkyl or aryl; tin compounds represented by the formula $SnR^{Y2}R^{Y3}R^{Y4}R^{Y5}$ wherein each of $R^{Y2}$, $R^{Y3}$, $R^{Y4}$ and $R^{Y5}$ is independently selected from the group consisting of halogen, $C_1$-$C_{20}$ alkyl, $C_3$-$C_{10}$ cycloalkyl, aryl, benzyl and $C_2$-$C_7$ alkenyl; and silicon compounds represented by the formula $SiR^{Y6}R^{Y7}R^{Y8}R^{Y9}$ wherein each of $R^{Y6}$, $R^{Y7}$, $R^{Y8}$, $R^{Y9}$ is independently selected from the group consisting of hydrogen, halogen, $C_1$-$C_{20}$ alkyl, halo, $C_1$-$C_7$ alkyl, aryl, heteroaryl, and vinyl. In addition, metal carbene olefin metathesis catalysts of formulas (XVI) to (XIX) may be optionally contacted with an activating compound where at least partial cleavage of a bond between the Group 8 transition metal and at least one Schiff base ligand occurs, wherein the activating compound is an inorganic acid such as hydrogen iodide, hydrogen bromide, hydrogen chloride, hydrogen fluoride, sulfuric acid, nitric acid, iodic acid, periodic acid, perchloric acid, HOClO, $HOClO_2$ and $HOIO_3$. In addition, metal carbene olefin metathesis catalysts of formulas (XVI) to (XIX) may be optionally contacted with an activating compound where at least partial cleavage of a bond between the Group 8 transition metal and at least one Schiff base ligand occurs, wherein the activating compound is an organic acid such as sulfonic acids including but not limited to methanesulfonic acid, aminobenzenesulfonic acid, benzenesulfonic acid, napthalenesulfonic acid, sulfanilic acid and trifluoromethanesulfonic acid; monocarboxylic acids including but not limited to acetoacetic acid, barbituric acid, bromoacetic acid, bromobenzoic acid, chloroacetic acid, chlorobenzoic acid, chlorophenoxyacetic acid, chloropropionic acid, cis-cinnamic acid, cyanoacetic acid, cyanobutyric acid, cyanophenoxyacetic acid, cyanopropionic acid, dichloroacetic acid, dichloroacetylacetic acid, dihydroxybenzoic acid, dihydroxymalic acid, dihydroxytartaric acid, dinicotinic acid, diphenylacetic acid, fluorobenzoic acid, formic acid, furancarboxylic acid, furoic acid, glycolic acid, hippuric acid, iodoacetic acid, iodobenzoic acid, lactic acid, lutidinic acid, mandelic acid, α-naphtoic acid, nitrobenzoic acid, nitrophenylacetic acid, o-phenylbenzoic acid, thioacetic acid, thiophene-carboxylic acid, trichloroacetic acid, and trihydroxybenzoic acid; and other acidic substances such as but not limited to picric acid and uric acid.

In addition, other examples of metal carbene olefin metathesis catalysts that may be used with the present invention are located in the following disclosures, each of which is incorporated herein by reference, U.S. Pat. Nos. 7,687,635; 7,671,224; 6,284,852; 6,486,279; and 5,977,393; International Publication Number WO2010/037550; and U.S. patent application Ser. Nos. 12/303,615; 10/590,380; 11/465,651 (Publication No.: US 2007/0043188); and Ser. No. 11/465,651 (Publication No.: US 2008/0293905 Corrected Publication); and European Pat. Nos. EP1757613B1 and EP1577282B1.

Non-limiting examples of metal carbene olefin metathesis catalysts that may be used to prepare supported complexes and in the reactions disclosed herein include the following, some of which for convenience are identified throughout this disclosure by reference to their molecular weight:

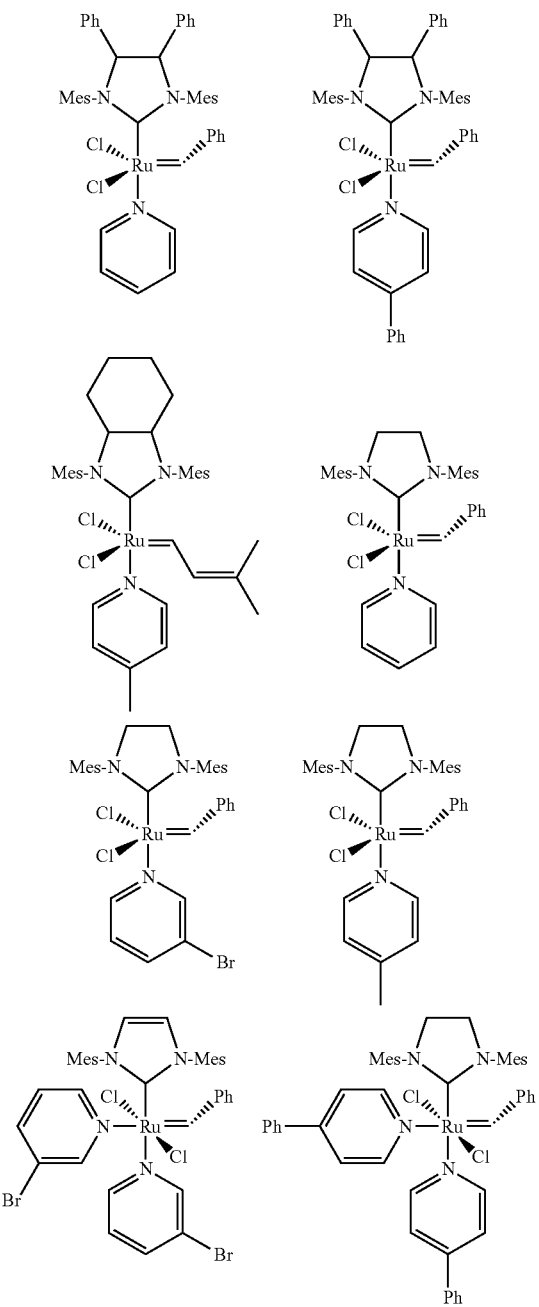

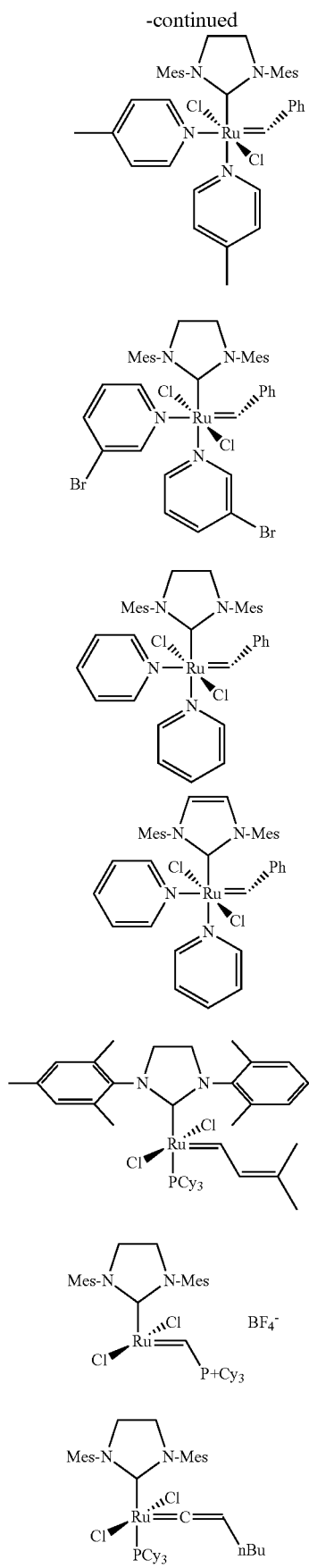
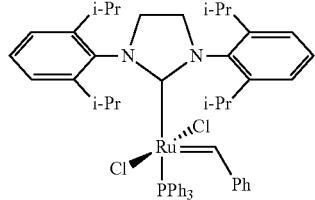
C916
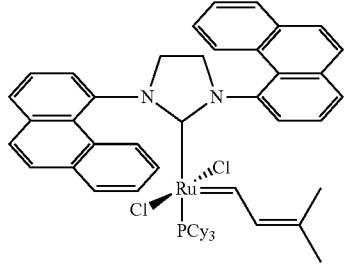
C965-p
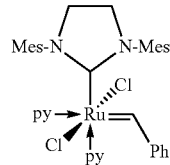
C727
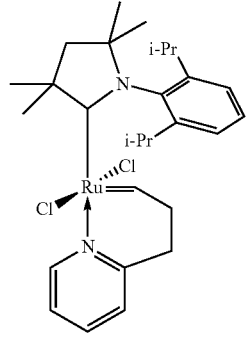
C577
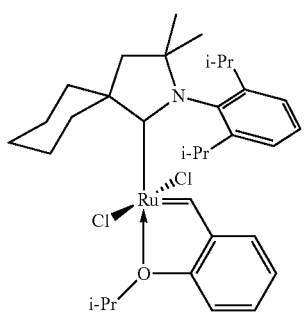
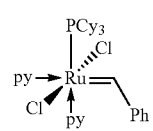
C701

-continued
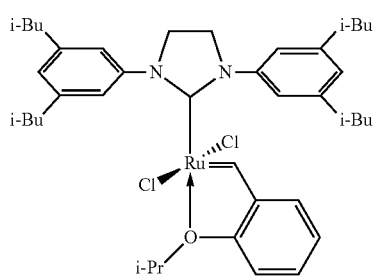
C767-m
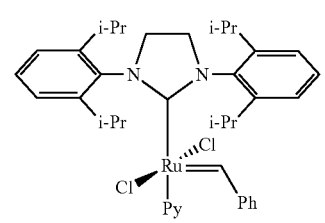
C811
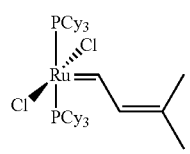
C801
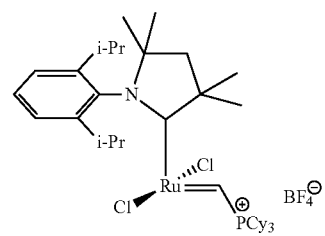
C838
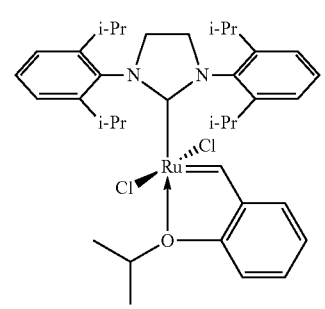
C712
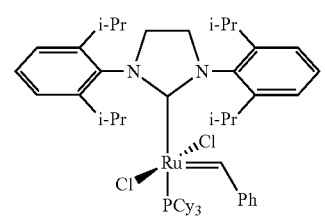
C933
-continued
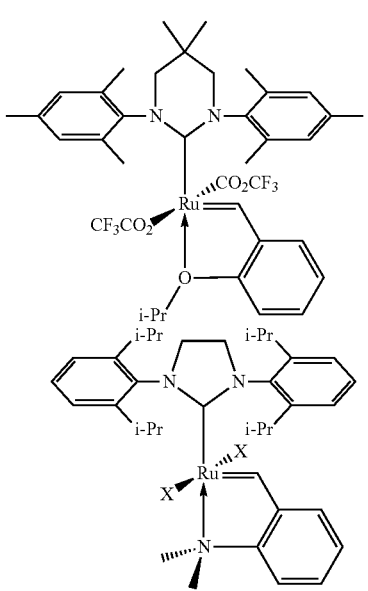
C824
C697 (X = Cl)
C785 (X = Br)
C879 (X = I)
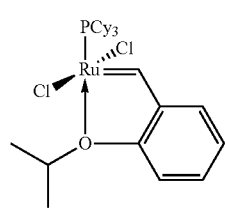
C601
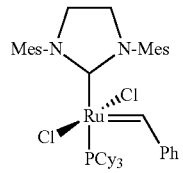
C848
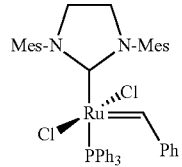
C831
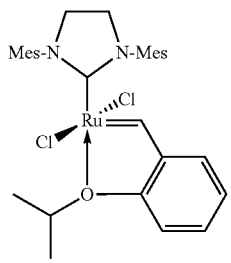
C627
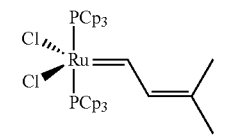
C716

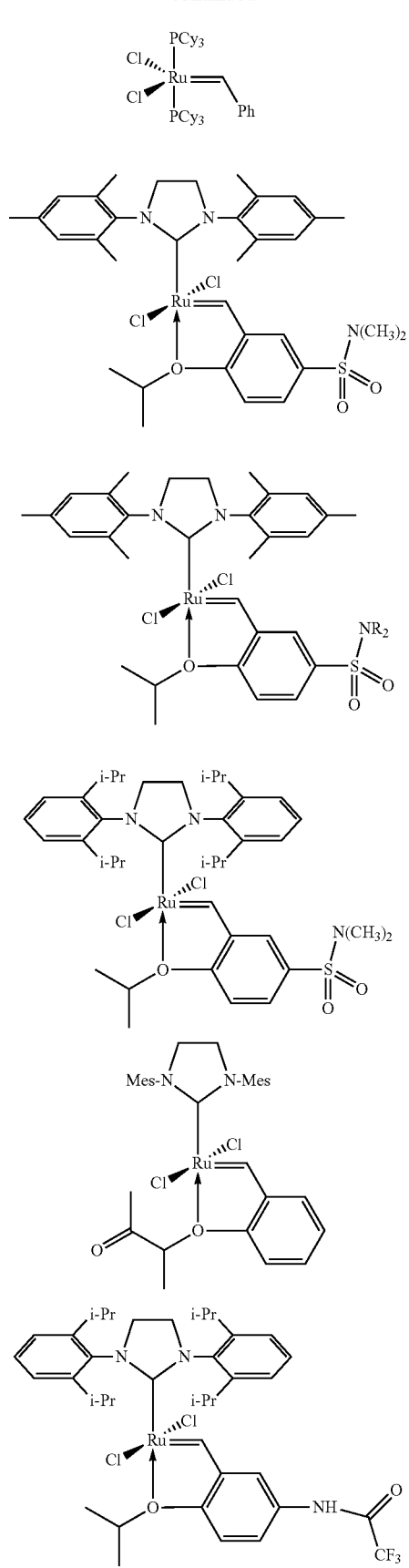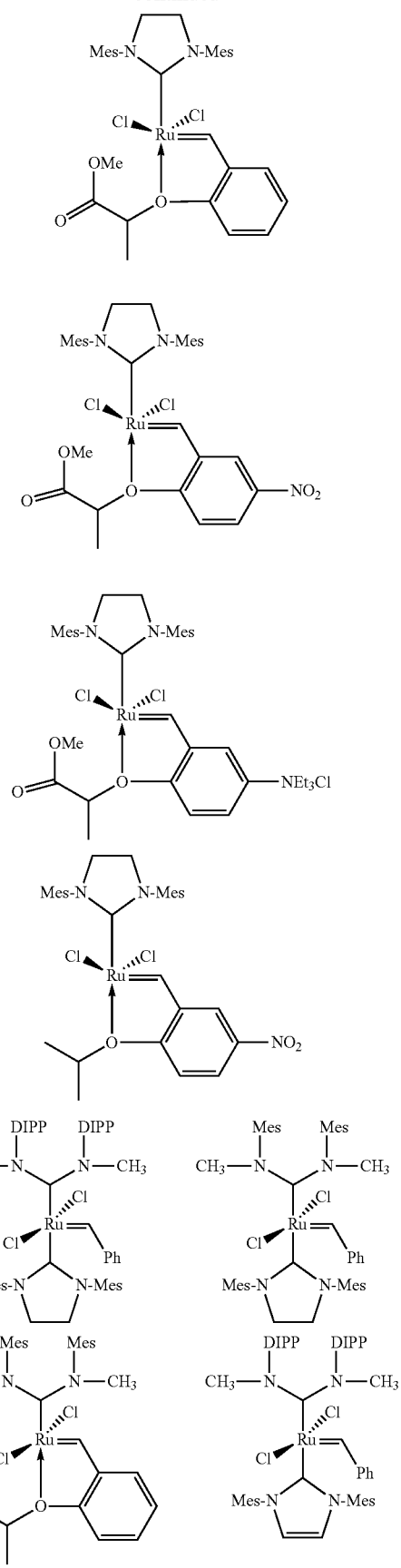

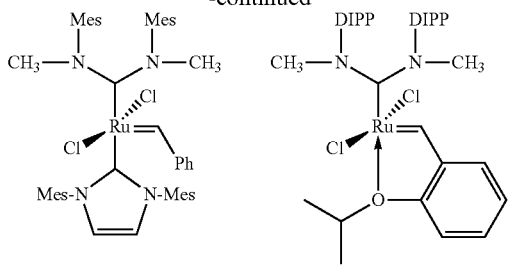

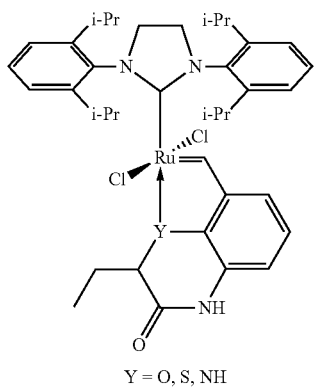

Y = O, S, NH

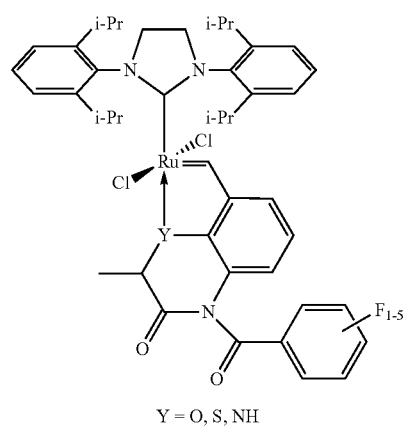

Y = O, S, NH

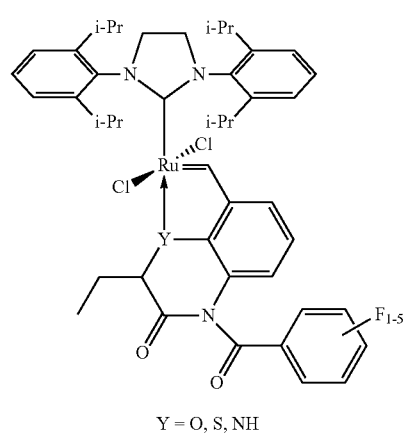

Y = O, S, NH

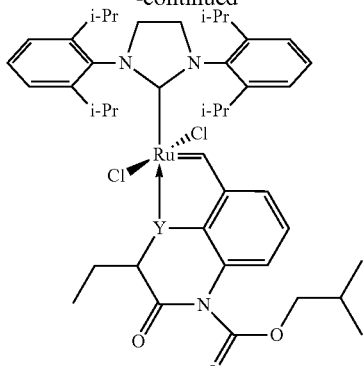

Y = O, S, NH

In the foregoing molecular structures and formulae, Ph represents phenyl, Cy represents cyclohexyl, Cp represents cyclopentyl, Me represents methyl, Bu represents n-butyl, t-Bu represents tert-butyl, i-Pr represents isopropyl, py represents pyridine (coordinated through the N atom), Mes represents mesityl (i.e., 2,4,6-trimethylphenyl), DiPP and DIPP represents 2,6-diisopropylphenyl, and MiPP represents 2-isopropylphenyl.

Further examples of metal carbene olefin metathesis catalysts useful to prepare supported complexes and in the reactions disclosed herein include the following: ruthenium (II) dichloro (3-methyl-2-butenylidene) bis(tricyclopentylphosphine) (C716); ruthenium (II) dichloro (3-methyl-2-butenylidene) bis(tricyclohexylphosphine) (C801); ruthenium (II) dichloro(phenylmethylene) bis (tricyclohexylphosphine) (C823); ruthenium (II) (1,3-bis-(2, 4,6-trimethylphenyl)-2-imidazolidinylidene) dichloro (phenylmethylene) (triphenylphosphine) (C830); ruthenium (II) dichloro (phenylvinylidene) bis(tricyclohexylphosphine) (C835); ruthenium (II) dichloro (tricyclohexylphosphine) (o-isopropoxyphenylmethylene) (C601); ruthenium (II) (1,3-bis-(2, 4,6-trimethylphenyl)-2-imidazolidinylidene) dichloro (phenylmethylene) bis(3-bromopyridine) (C884); [1,3-bis-(2,4,6-trimethylphenyl)-2-imidazolidinylidene]dichloro(o-isopropoxyphenylmethylene)ruthenium(II) (C627); [1,3-bis-(2,4,6-trimethylphenyl)-2-imidazolidinylidene] dichloro (benzylidene) (triphenylphosphine) ruthenium(II) (C831); [1,3-bis-(2,4,6-trimethylphenyl)-2-imidazolidinylidene] dichloro (benzylidene)(methyldiphenylphosphine)ruthenium(II) (C769); [1,3-bis-(2,4,6-trimethylphenyl)-2-imidazolidinylidene]dichloro(benzylidene) (tricyclohexylphosphine)ruthenium(II) (C848); [1,3-bis-(2, 4,6-trimethylphenyl)-2-imidazolidinylidene] dichloro (benzylidene) (diethylphenylphosphine) ruthenium(II) ($C_{735}$); [1,3-bis-(2,4,6-trimethylphenyl)-2-imidazolidinylidene]dichloro(benzylidene)(tri-n-butylphosphine)ruthenium(II) (C771); [1,3-bis-(2,4,6-trimethylphenyl)-2-imidazolidinylidene]dichloro(3-methyl-2-butenylidene) (triphenylphosphine)ruthenium(II) (C809); [1,3-bis-(2,4,6-trimethylphenyl)-2-imidazolidinylidene]dichloro(3-methyl-2-butenylidene)(methyldiphenylphosphine)ruthenium(II) (C747); [1,3-bis-(2,4,6-trimethylphenyl)-2-imidazolidinylidene]dichloro(3-methyl-2-butenylidene) (tricyclohexylphosphine) ruthenium(II) (C827); [1,3-bis-(2,4,6-trimethylphenyl)-2-imidazolidinylidene]dichloro(3-methyl-2-butenylidene)(diethylphenylphosphine)ruthenium(II) (C713); [1,3-bis-(2,4,6-trimethylphenyl)-2-imidazolidinylidene] dichloro (3-methyl-2-butenylidene) (tri-n-butylphosphine)ruthenium(II) (C749); [1,3-bis-(2,4,6-trimethylphenyl)-2-imidazolidinylidene]dichloro(phenylindenylidene)(tripenylphosphine)ruthenium(II) (C931); [1,3-bis-(2,4,6-trimethylphenyl)-2-imidazolidinylidene] dichloro (phenylindenylidene) (methylphenylphosphine) ruthenium(II) (C869); [1,3-bis-(2,4,6-trimethylphenyl)-2-imidazolidinylidene] dichloro (phenylindenylidene) (tricyclohexylphosphine) ruthenium(II) (C949); [1,3-bis-(2,4,6-trimethylphenyl)-2-imidazolidinylidene]dichloro (phenylindenylidene)(diethylphenylphosphine)ruthenium (II) (C835); [1,3-bis-(2,4,6-trimethylphenyl)-2-imidazolidinylidene]dichloro(phenylindenylidene)(tri-n-butylphosphine)ruthenium(II) (C871); ruthenium (II) dichloro (tert-butylvinylidene) bis(tricyclohexylphosphine) (C815); [1,3-bis-(2,4,6-trimethylphenyl)-2-imidazolidinylidene]dichloro(phenylvinylidene)(tricyclohexylphosphine)ruthenium(II); and [1,3-bis-(2,4,6-trimethylphenyl)-2-imidazolidinylidene]dichloro(tert-butylvinylidene) (tricyclohexylphosphine) ruthenium(II) (C841).

Still further metal carbene olefin metathesis catalysts useful in ROMP reactions, and/or in other metathesis reactions, such as ring-closing metathesis, cross metathesis, ring-opening cross metathesis, self-metathesis, ethenolysis, alkenolysis, acyclic diene metathesis polymerization, and combinations thereof, include the following structures:

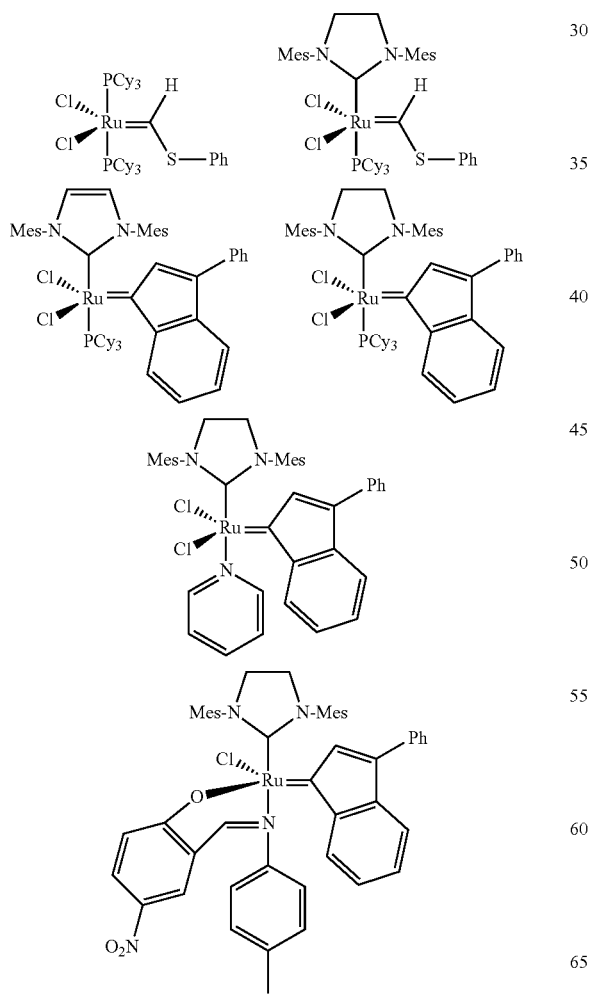

-continued

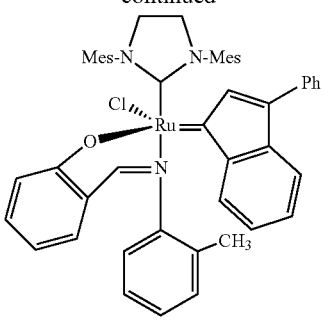

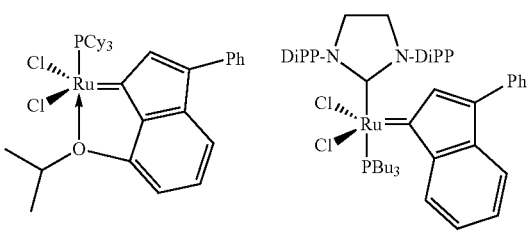

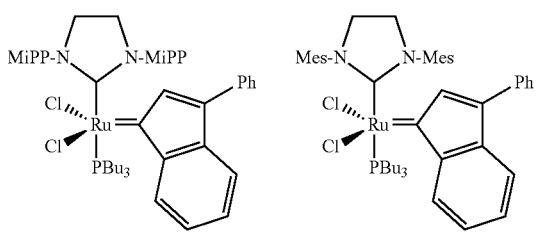

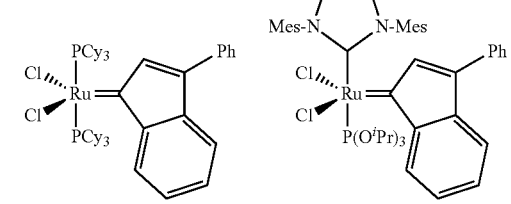

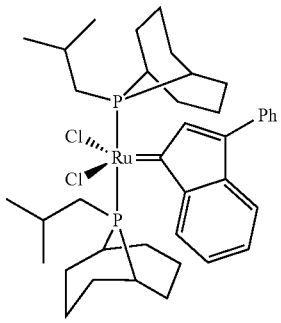

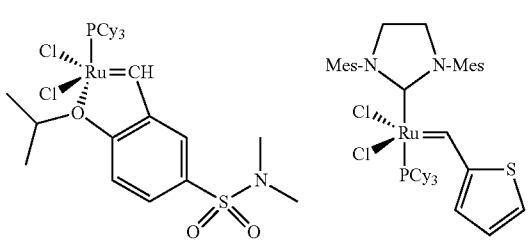

-continued

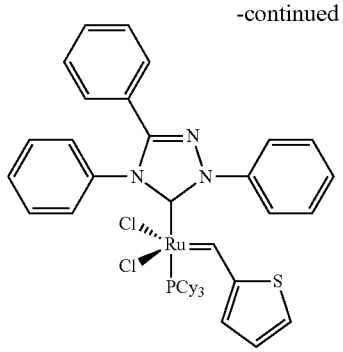

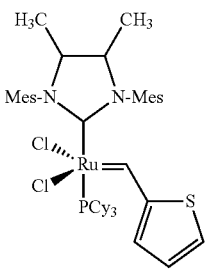

In general, the transition metal complexes (metal carbene olefin metathesis catalysts) used herein can be prepared by several different methods, such as those described by Schwab et al. (1996) *J. Am. Chem. Soc.* 118:100-110, Scholl et al. (1999) *Org. Lett.* 6:953-956, Sanford et al. (2001) *J. Am. Chem. Soc.* 123:749-750, U.S. Pat. No. 5,312,940, and U.S. Pat. No. 5,342,909, the disclosures of each of which are incorporated herein by reference. Also see U.S. Pat. Pub. No. 2003/0055262 to Grubbs et al., WO 02/079208, and U.S. Pat. No. 6,613,910 to Grubbs et al., the disclosures of each of which are incorporated herein by reference. Preferred synthetic methods are described in WO 03/11455A1 to Grubbs et al., the disclosure of which is incorporated herein by reference.

Preferred metal carbene olefin metathesis catalysts are Group 8 transition metal complexes having the structure of formula (I) commonly called "First Generation Grubbs" catalysts, formula (III) commonly called "Second Generation Grubbs" catalysts, or formula (VII) commonly called "Grubbs-Hoveyda" catalysts.

More preferred metal carbene olefin metathesis catalysts have the structure of formula (I)

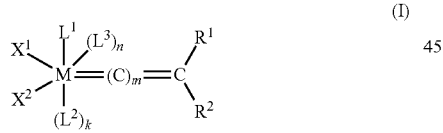

in which:
M is a Group 8 transition metal;
$L^1$, $L^2$, and $L^3$ are neutral electron donor ligands;
n is 0 or 1;
m is 0, 1, or 2;
k is 0 or 1;
$X^1$ and $X^2$ are anionic ligands;
$R^1$ and $R^2$ are independently selected from hydrogen, hydrocarbyl, substituted hydrocarbyl, heteroatom-containing hydrocarbyl, substituted heteroatom-containing hydrocarbyl, and functional groups,
wherein any two or more of $X^1$, $X^2$, $L^1$, $L^2$, $L^3$, $R^1$, and $R^2$ can be taken together to form one or more cyclic groups, and further wherein any one or more of $X^1$, $X^2$, $L^1$, $L^2$, $L^3$, $R^1$, and $R^2$ may be attached to a support;

and formula (VII)

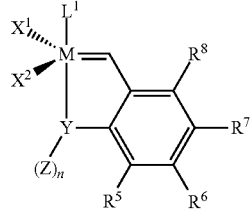

wherein,
M is a Group 8 transition metal;
$L^1$ is a neutral electron donor ligand;
$X^1$ and $X^2$ are anionic ligands;
Y is a heteroatom selected from O or N;
$R^5$, $R^6$, $R^7$, and $R^8$ are independently selected from hydrogen, hydrocarbyl, substituted hydrocarbyl, heteroatom-containing hydrocarbyl, substituted heteroatom-containing hydrocarbyl, and functional groups;
n is 0, 1, or 2; and
Z is selected from hydrogen, hydrocarbyl, substituted hydrocarbyl, heteroatom-containing hydrocarbyl, substituted heteroatom-containing hydrocarbyl, and functional groups,
wherein any combination of Y, Z, $R^5$, $R^6$, R, and $R^8$ can be linked to form one or more cyclic groups, and further wherein any combination of $X^1$, $X^2$, L, Y, Z, $R^5$, $R^6$, $R^7$, and $R^8$ may be attached to a support.

Most preferred metal carbene olefin metathesis catalysts have the structure of formula (I)

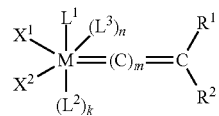

in which:
M is ruthenium;
n is 0;
m is 0;
k is 1;
$L^1$ and $L^2$ are trisubstituted phosphines independently selected from the group consisting of tri-n-butylphosphine (Pn-Bu$_3$), tricyclopentylphosphine (PCp$_3$), tricyclohexylphosphine (PCy$_3$), triisopropylphosphine (P-i-Pr$_3$), triphenylphosphine (PPh$_3$), methyldiphenylphosphine (PMePh$_2$), dimethylphenylphosphine (PMe$_2$Ph), and diethylphenylphosphine (PEt$_2$Ph); or $L^1$ is an N-heterocyclic carbene selected from the group consisting of 1,3-bis(2,4,6-trimethylphenyl)-2-imidazolidinylidene, 1,3-bis(2,4,6-trimethylphenyl)imidazol-2-ylidene, 1,3-bis(2,6-di-isopropylphenyl)-2-imidazolidinylidene, and 1,3-bis(2,6-di-isopropylphenyl)imidazol-2-ylidene and $L^2$ is a trisubstituted phosphine selected from the group consisting of tri-n-butylphosphine (Pn-Bu$_3$), tricyclopentylphosphine (PCp$_3$), tricyclohexylphosphine (PCy$_3$), triisopropylphosphine (P-i-Pr$_3$), triphenylphosphine (PPh$_3$), methyldiphenylphosphine (PMePh$_2$), dimethylphenylphosphine (PMe$_2$Ph), and diethylphenylphosphine (PEt$_2$Ph);
$X^1$ and $X^2$ are chloride;
$R^1$ is hydrogen and $R^2$ is phenyl or —CH═C(CH$_3$)$_2$ or thienyl or phenylthio; or $R^1$ and $R^2$ are taken together to form phenylindenylidene;

and formula (VII)

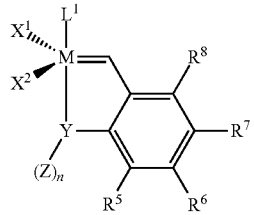

(VII)

wherein,

M is ruthenium;

L¹ is a trisubstituted phosphine selected from the group consisting of tri-n-butylphosphine (Pn-Bu₃), tricyclopentylphosphine (PCp₃), tricyclohexylphosphine (PCy₃), triisopropylphosphine (P-i-Pr₃), triphenylphosphine (PPh₃), methyldiphenylphosphine (PMePh₂), dimethylphenylphosphine (PMe₂Ph), and diethylphenylphosphine (PEt₂Ph); or L¹ is an N-heterocyclic carbene selected from the group consisting of 1,3-bis(2,4,6-trimethylphenyl)-2-imidazolidinylidene, 1,3-bis(2,4,6-trimethylphenyl)imidazol-2-ylidene, 1,3-bis(2,6-di-isopropylphenyl)-2-imidazolidinylidene, and 1,3-bis(2,6-di-isopropylphenyl)imidazol-2-ylidene;

$X^1$ and $X^2$ are chloride;

Y is oxygen;

$R^5$, $R^6$, $R^7$, and $R^8$ are each hydrogen;

n is 1; and

Z is isopropyl.

Examples of preferred metal carbene olefin metathesis catalysts have the structure of formula (I)

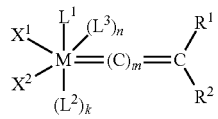

(I)

in which:

M is Ruthenium;

n is 0;

m is 0;

k is 1;

L¹ is an N-heterocyclic carbene selected from the group consisting of 1,3-bis(2,4,6-trimethylphenyl)-2-imidazolidinylidene and 1,3-bis(2,4,6-trimethylphenyl)imidazol-2-ylidene;

L² is a trisubstituted phosphine independently selected from the group consisting of tri-n-butylphosphine (Pn-Bu₃), tricyclopentylphosphine (PCp₃), tricyclohexylphosphine (PCy₃), triisopropylphosphine (P-i-Pr₃), triphenylphosphine (PPh₃), methyldiphenylphosphine (PMePh₂), dimethylphenylphosphine (PMe₂Ph), and diethylphenylphosphine (PEt₂Ph);

$X^1$ and $X^2$ are chloride;

$R^1$ is hydrogen and $R^2$ is phenyl or —CH=C(CH₃)₂ or thienyl; or $R^1$ and $R^2$ are taken together to form phenylindenylidene.

Examples of preferred metal carbene olefin metathesis catalysts have the structure of formula (I)

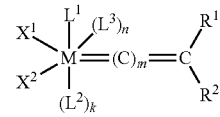

(I)

in which:

M is Ruthenium;

n is 0;

m is 0;

k is 1;

L¹ is an N-heterocyclic carbene 1,3-bis(2,4,6-trimethylphenyl)-2-imidazolidinylidene;

L² is a trisubstituted phosphine independently selected from the group consisting of tri-n-butylphosphine (Pn-Bu₃), tricyclopentylphosphine (PCp₃), tricyclohexylphosphine (PCy₃), triisopropylphosphine (P-i-Pr₃), triphenylphosphine (PPh₃), methyldiphenylphosphine (PMePh₂), dimethylphenylphosphine (PMe₂Ph), and diethylphenylphosphine (PEt₂Ph);

$X^1$ and $X^2$ are chloride;

$R^1$ is hydrogen and $R^2$ is phenyl or —CH=C(CH₃)₂ or thienyl; or $R^1$ and $R^2$ are taken together to form phenylindenylidene.

Examples of preferred metal carbene olefin metathesis catalysts have the structure of formula (I)

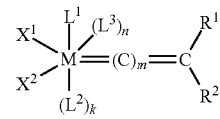

(I)

in which:

M is Ruthenium;

n is 0;

m is 0;

k is 1;

L¹ is an N-heterocyclic carbene 1,3-bis(2,4,6-trimethylphenyl)imidazol-2-ylidene;

L² is a trisubstituted phosphine independently selected from the group consisting of tri-n-butylphosphine (Pn-Bu₃), tricyclopentylphosphine (PCp₃), tricyclohexylphosphine (PCy₃), triisopropylphosphine (P-i-Pr₃), triphenylphosphine (PPh₃), methyldiphenylphosphine (PMePh₂), dimethylphenylphosphine (PMe₂Ph), and diethylphenylphosphine (PEt₂Ph);

$X^1$ and $X^2$ are chloride;

$R^1$ is hydrogen and $R^2$ is phenyl or —CH=C(CH₃)₂ or thienyl; or $R^1$ and $R^2$ are taken together to form phenylindenylidene.

Examples of preferred metal carbene olefin metathesis catalysts have the structure of formula (I)

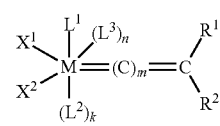

(I)

in which:
M is Ruthenium;
n is 0;
m is 0;
k is 1;
L¹ is an N-heterocyclic carbene selected from the group consisting of 1,3-bis(2,4,6-trimethylphenyl)-2-imidazolidinylidene and 1,3-bis(2,4,6-trimethylphenyl)imidazol-2-ylidene;
L² is a trisubstituted phosphine independently selected from the group consisting of tri-n-butylphosphine (Pn-Bu₃), tricyclopentylphosphine (PCp₃), tricyclohexylphosphine (PCy₃), triisopropylphosphine (P-i-Pr₃), triphenylphosphine (PPh₃), methyldiphenylphosphine (PMePh₂), dimethylphenylphosphine (PMe₂Ph), and diethylphenylphosphine (PEt₂Ph);
X¹ and X² are chloride; and
R¹ is hydrogen and R² is phenyl or —CH=C(CH₃)₂; or R¹ and R² are taken together to form phenylindenylidene.

Examples of preferred metal carbene olefin metathesis catalysts have the structure of formula (I)

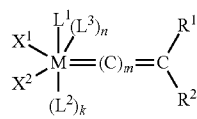
(I)

in which:
M is Ruthenium;
n is 0;
m is 0;
k is 1;
L¹ is an N-heterocyclic carbene 1,3-bis(2,4,6-trimethylphenyl)-2-imidazolidinylidene;
L² is a trisubstituted phosphine independently selected from the group consisting of tri-n-butylphosphine (Pn-Bu₃), tricyclopentylphosphine (PCp₃), tricyclohexylphosphine (PCy₃), triisopropylphosphine (P-i-Pr₃), triphenylphosphine (PPh₃), methyldiphenylphosphine (PMePh₂), dimethylphenylphosphine (PMe₂Ph), and diethylphenylphosphine (PEt₂Ph);
X¹ and X² are chloride; and
R¹ is hydrogen and R² is phenyl or —CH=C(CH₃)₂; or R¹ and R² are taken together to form phenylindenylidene.

Examples of preferred metal carbene olefin metathesis catalysts have the structure of formula (I)

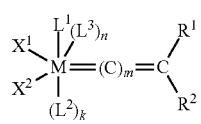
(I)

in which:
M is Ruthenium;
n is 0;
m is 0;
k is 1;
L¹ is an N-heterocyclic carbene 1,3-bis(2,4,6-trimethylphenyl)imidazol-2-ylidene;
L² is a trisubstituted phosphine independently selected from the group consisting of tri-n-butylphosphine (Pn-Bu₃), tricyclopentylphosphine (PCp₃), tricyclohexylphosphine (PCy₃), triisopropylphosphine (P-i-Pr₃), triphenylphosphine (PPh₃), methyldiphenylphosphine (PMePh₂), dimethylphenylphosphine (PMe₂Ph), and diethylphenylphosphine (PEt₂Ph);
X¹ and X² are chloride; and
R¹ is hydrogen and R² is phenyl or —CH=C(CH₃)₂; or R¹ and R² are taken together to form phenylindenylidene.

Examples of preferred metal carbene olefin metathesis catalysts have the structure of formula (I)

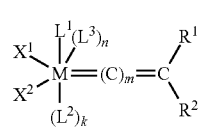
(I)

in which:
M is Ruthenium;
n is 0;
m is 0;
k is 1;
L¹ is an N-heterocyclic carbene selected from the group consisting of 1,3-bis(2,4,6-trimethylphenyl)-2-imidazolidinylidene and 1,3-bis(2,4,6-trimethylphenyl)imidazol-2-ylidene;
L² is a trisubstituted phosphine independently selected from the group consisting of tri-n-butylphosphine (Pn-Bu₃), tricyclopentylphosphine (PCp₃), tricyclohexylphosphine (PCy₃), triisopropylphosphine (P-i-Pr₃), triphenylphosphine (PPh₃), methyldiphenylphosphine (PMePh₂), dimethylphenylphosphine (PMe₂Ph), and diethylphenylphosphine (PEt₂Ph);
X¹ and X² are chloride;
R¹ is hydrogen; and
R² is phenyl or —CH=C(CH₃)₂.

Examples of preferred metal carbene olefin metathesis catalysts have the structure of formula (I)

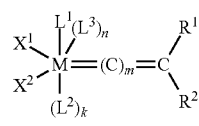
(I)

in which:
M is Ruthenium;
n is 0;
m is 0;
k is 1;
L¹ is an N-heterocyclic carbene 1,3-bis(2,4,6-trimethylphenyl)-2-imidazolidinylidene;
L² is a trisubstituted phosphine independently selected from the group consisting of tri-n-butylphosphine (Pn-Bu₃), tricyclopentylphosphine (PCp₃), tricyclohexylphosphine (PCy₃), triisopropylphosphine (P-i-Pr₃), triphenylphosphine (PPh₃), methyldiphenylphosphine (PMePh₂), dimethylphenylphosphine (PMe₂Ph), and diethylphenylphosphine (PEt₂Ph);
X¹ and X² are chloride;
R¹ is hydrogen; and
R² is phenyl or —CH=C(CH₃)₂.

Examples of preferred metal carbene olefin metathesis catalysts have the structure of formula (I)

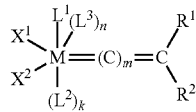
(I)

in which:
M is Ruthenium;
n is 0;
m is 0;
k is 1;
L¹ is an N-heterocyclic carbene 1,3-bis(2,4,6-trimethylphenyl)imidazol-2-ylidene;
L² is a trisubstituted phosphine independently selected from the group consisting of tri-n-butylphosphine (Pn-Bu₃), tricyclopentylphosphine (PCp₃), tricyclohexylphosphine (PCy₃), triisopropylphosphine (P-i-Pr₃), triphenylphosphine (PPh₃), methyldiphenylphosphine (PMePh₂), dimethylphenylphosphine (PMe₂Ph), and diethylphenylphosphine (PEt₂Ph);
X¹ and X² are chloride;
R¹ is hydrogen; and
R² is phenyl or —CH═C(CH₃)₂.

Examples of preferred metal carbene olefin metathesis catalysts have the structure of formula (I)

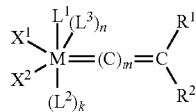
(I)

in which:
M is Ruthenium;
n is 0;
m is 0;
k is 1;
L¹ is an N-heterocyclic carbene selected from the group consisting of 1,3-bis(2,4,6-trimethylphenyl)-2-imidazolidinylidene and 1,3-bis(2,4,6-trimethylphenyl)imidazol-2-ylidene;
L² is a trisubstituted phosphine independently selected from the group consisting of tri-n-butylphosphine (Pn-Bu₃), tricyclopentylphosphine (PCp₃), tricyclohexylphosphine (PCy₃), triisopropylphosphine (P-i-Pr₃), triphenylphosphine (PPh₃), methyldiphenylphosphine (PMePh₂), dimethylphenylphosphine (PMe₂Ph), and diethylphenylphosphine (PEt₂Ph);
X¹ and X² are chloride; and
R¹ and R² are taken together to form phenylindenylidene.

Examples of preferred metal carbene olefin metathesis catalysts have the structure of formula (I)

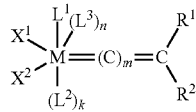
(I)

in which:
M is Ruthenium;
n is 0;
m is 0;
k is 1;
L¹ is an N-heterocyclic carbene 1,3-bis(2,4,6-trimethylphenyl)-2-imidazolidinylidene;
L² is a trisubstituted phosphine independently selected from the group consisting of tri-n-butylphosphine (Pn-Bu₃), tricyclopentylphosphine (PCp₃), tricyclohexylphosphine (PCy₃), triisopropylphosphine (P-i-Pr₃), triphenylphosphine (PPh₃), methyldiphenylphosphine (PMePh₂), dimethylphenylphosphine (PMe₂Ph), and diethylphenylphosphine (PEt₂Ph);
X¹ and X² are chloride; and
R¹ and R² are taken together to form phenylindenylidene.

Examples of preferred metal carbene olefin metathesis catalysts have the structure of formula (I)

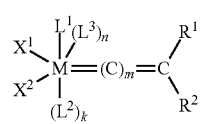
(I)

in which:
M is ruthenium;
n is 0;
m is 0;
k is 1;
L¹ is an N-heterocyclic carbene 1,3-bis(2,4,6-trimethylphenyl)imidazol-2-ylidene;
L² is a trisubstituted phosphine independently selected from the group consisting of tri-n-butylphosphine (Pn-Bu₃), tricyclopentylphosphine (PCp₃), tricyclohexylphosphine (PCy₃), triisopropylphosphine (P-i-Pr₃), triphenylphosphine (PPh₃), methyldiphenylphosphine (PMePh₂), dimethylphenylphosphine (PMe₂Ph), and diethylphenylphosphine (PEt₂Ph);
X¹ and X² are chloride; and
R¹ and R² are taken together to form phenylindenylidene.

Examples of preferred metal carbene olefin metathesis catalysts have the structure of formula (I)

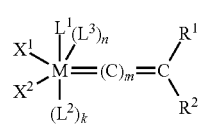
(I)

in which:
M is ruthenium;
n is 0;
m is 1;
k is 1;
L¹ and L² are trisubstituted phosphines independently selected from the group consisting of tri-n-butylphosphine (Pn-Bu₃), tricyclopentylphosphine (PCp₃), tricyclohexylphosphine (PCy₃), triisopropylphosphine (P-i-Pr₃), triphenylphosphine (PPh₃), methyldiphenylphosphine (PMePh₂), dimethylphenylphosphine (PMe₂Ph), and diethylphenylphosphine (PEt₂Ph); or L¹ is an N-heterocyclic carbene selected from the group consisting of 1,3-bis(2,4,6-trimethylphenyl)-2-imidazolidinylidene, and 1,3-bis(2,4,6-trimethylphenyl)imidazol-2-ylidene, and L² is a trisubstituted phosphine selected from the group consisting of tri-n-butylphosphine (Pn-Bu₃), tricyclopentylphosphine (PCp₃), tricyclohexylphosphine (PCy₃), triisopropylphosphine (P-i-Pr₃), triphenylphosphine (PPh₃), methyldiphenylphosphine (PMePh₂), dimethylphenylphosphine (PMe₂Ph), and diethylphenylphosphine (PEt₂Ph);

$X^1$ and $X^2$ are chloride;

$R^1$ is hydrogen; and $R^2$ is phenyl or tert-butyl.

Examples of preferred metal carbene olefin metathesis catalysts have the structure of formula (I)

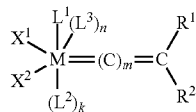

(I)

in which:

M is ruthenium;

n is 0;

m is 1;

k is 1;

$L^1$ is an N-heterocyclic carbene selected from the group consisting of 1,3-bis(2,4,6-trimethylphenyl)-2-imidazolidinylidene and 1,3-bis(2,4,6-trimethylphenyl)imidazol-2-ylidene;

$L^2$ is a trisubstituted phosphine selected from the group consisting of tri-n-butylphosphine (Pn-Bu₃), tricyclopentylphosphine (PCp₃), tricyclohexylphosphine (PCy₃), triisopropylphosphine (P-i-Pr₃), triphenylphosphine (PPh₃), methyldiphenylphosphine (PMePh₂), dimethylphenylphosphine (PMe₂Ph), and diethylphenylphosphine (PEt₂Ph);

$X^1$ and $X^2$ are chloride;

$R^1$ is hydrogen; and $R^2$ is phenyl or tert-butyl.

Examples of preferred metal carbene olefin metathesis catalysts have the structure of formula (I)

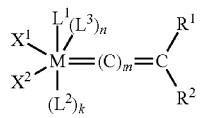

(I)

in which:

M is ruthenium;

n is 0;

m is 1;

k is 1;

$L^1$ is an N-heterocyclic carbene 1,3-bis(2,4,6-trimethylphenyl)-2-imidazolidinylidene;

$L^2$ is a trisubstituted phosphine selected from the group consisting of tri-n-butylphosphine (Pn-Bu₃), tricyclopentylphosphine (PCp₃), tricyclohexylphosphine (PCy₃), triisopropylphosphine (P-i-Pr₃), triphenylphosphine (PPh₃), methyldiphenylphosphine (PMePh₂), dimethylphenylphosphine (PMe₂Ph), and diethylphenylphosphine (PEt₂Ph);

$X^1$ and $X^2$ are chloride;

$R^1$ is hydrogen; and $R^2$ is phenyl or tert-butyl.

Examples of preferred metal carbene olefin metathesis catalysts have the structure of formula (I)

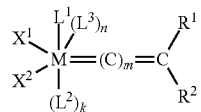

(I)

in which:

M is ruthenium;

n is 0;

m is 1;

k is 1;

$L^1$ is an N-heterocyclic carbene 1,3-bis(2,4,6-trimethylphenyl)imidazol-2-ylidene;

$L^2$ is a trisubstituted phosphine selected from the group consisting of tri-n-butylphosphine (Pn-Bu₃), tricyclopentylphosphine (PCp₃), tricyclohexylphosphine (PCy₃), triisopropylphosphine (P-i-Pr₃), triphenylphosphine (PPh₃), methyldiphenylphosphine (PMePh₂), dimethylphenylphosphine (PMe₂Ph), and diethylphenylphosphine (PEt₂Ph);

$X^1$ and $X^2$ are chloride;

$R^1$ is hydrogen; and $R^2$ is phenyl or tert-butyl.

Suitable supports for any of the metal carbene olefin metathesis catalysts described herein may be of synthetic, semi-synthetic, or naturally occurring materials, which may be organic or inorganic, e.g., polymeric, ceramic, or metallic. Attachment to the support will generally, although not necessarily, be covalent, and the covalent linkage may be direct or indirect. Indirect covalent linkages are typically, though not necessarily, through a functional group on a support surface. Ionic attachments are also suitable, including combinations of one or more anionic groups on the metal complexes coupled with supports containing cationic groups, or combinations of one or more cationic groups on the metal complexes coupled with supports containing anionic groups.

When utilized, suitable supports may be selected from silicas, silicates, aluminas, aluminum oxides, silica-aluminas, aluminosilicates, zeolites, titanias, titanium dioxide, magnetite, magnesium oxides, boron oxides, clays, zirconias, zirconium dioxide, carbon, polymers, cellulose, cellulosic polymers amylose, amylosic polymers, or a combination thereof. The support preferably comprises silica, a silicate, or a combination thereof.

In certain embodiments, it is also possible to use a support that has been treated to include functional groups, inert moieties, and/or excess ligands. Any of the functional groups described herein are suitable for incorporation on the support, and may be generally accomplished through techniques known in the art. Inert moieties may also be incorporated on the support to generally reduce the available attachment sites on the support, e.g., in order to control the placement, or amount, of a complex linked to the support.

The metal carbene olefin metathesis catalysts that are described infra may be utilized in olefin metathesis reactions according to techniques known in the art. The metal carbene olefin metathesis catalyst is typically added to the resin composition as a solid, a solution, or as a suspension. When the metal carbene olefin metathesis catalyst is added to the resin composition as a suspension, the metal carbene olefin metathesis catalyst is suspended in a dispersing carrier such as mineral oil, paraffin oil, soybean oil, tri-isopropylbenzene, or any hydrophobic liquid which has a sufficiently high viscosity so as to permit effective dispersion of the metal carbene olefin metathesis catalyst, and which is sufficiently inert and which has a sufficiently high boiling point so that is does not act as a low-boiling impurity in the olefin metathesis reaction. It will be appreciated that the amount of metal carbene olefin metathesis catalyst that is used (i.e., the "catalyst loading") in the reaction is dependent upon a variety of factors such as the identity of the reactants and the reaction conditions that are employed. It is therefore understood that catalyst loading may be optimally and independently chosen for each reaction. In general, however, the metal carbene olefin metathesis catalyst will be present in an amount that ranges from a low of about 0.1 ppm, 1 ppm, or 5 ppm, to a high of about 10 ppm, 15 ppm, 25 ppm, 50 ppm, 100 ppm, 200 ppm, 500 ppm, or 1000 ppm relative to the amount of an olefinic substrate.

The metal carbene olefin metathesis catalyst will generally be present in an amount that ranges from a low of about 0.00001 mol %, 0.0001 mol %, or 0.0005 mol %, to a high of about 0.001 mol %, 0.0015 mol %, 0.0025 mol %, 0.005 mol %, 0.01 mol %, 0.02 mol %, 0.05 mol %, or 0.1 mol % relative to the olefinic substrate.

When expressed as the molar ratio of monomer to catalyst, the catalyst (the "monomer to catalyst ratio"), loading will generally be present in an amount that ranges from a low of about 10,000,000:1, 1,000,000:1, or 200,00:1, to a high of about 100,000:1 66,667:1, 40,000:1, 20,000:1, 10,000:1, 5,000:1, or 1,000:1.

Cyclic Olefin (Resin) Compositions and Articles

Cyclic olefin resin, particularly ROMP, compositions according to the invention, generally comprise at least one cyclic olefin, at least one metal carbene olefin metathesis catalyst, at least one adhesion promoter comprising at least one compound containing at least two isocyanate groups, at least one functional elastomer of the invention, and at least one substrate material, such as, for example, a glass or carbon substrate material. In another embodiment, cyclic olefin resin, particularly ROMP, compositions according to the invention, generally comprise at least one cyclic olefin, at least one metal carbene olefin metathesis catalyst, at least one adhesion promoter comprising at least one compound containing at least two isocyanate groups, at least one functional elastomer of the invention, and at least one heteroatom-functionalized substrate. The cyclic olefins described hereinabove are suitable for use and may be functionalized or unfunctionalized, and may be substituted or unsubstituted. In general, particularly advantageous results may be obtained for ROMP resin compositions wherein a functional elastomer of the invention is present in an amount effective to improve the adhesion of the ROMP composition to the substrate material and improve the impact properties (e.g., impact strength or impact toughness) of the polymer-matrix composite when the ROMP composition is subjected to metathesis catalysis conditions in the presence of the substrate material. Additionally, cyclic olefin resin compositions according to the invention may also comprise at least one cyclic olefin, at least one adhesion promoter comprising at least one compound containing at least two isocyanate groups, and at least one functional elastomer of the invention, where the resin composition is combined with at least one metal carbene olefin metathesis catalyst, and the resulting resin composition is applied to at least one substrate, such as, for example, a glass substrate or carbon substrate. Additionally, cyclic olefin resin compositions according to the invention may also comprise at least one cyclic olefin, at least one adhesion promoter comprising at least one compound containing at least two isocyanate groups, and at least one functional elastomer of the invention, where the resin composition is combined with at least one metal carbene olefin metathesis catalyst, and the resulting resin composition is applied to at least one substrate, wherein the substrate may be functionalized substrate, such as, for example, a heteroatom-functionalized substrate, such as, for example, an amino-functionalized substrate.

The amounts of the adhesion promoter in the resin composition may vary over a wide range and may vary depending on the manufacturing operation or the particular end-use application. Generally, any level of adhesion promoter which produces a desired increase in mechanical properties is of particular interest. When formulated or combined with a resin composition, the concentration of the adhesion promoter typically ranges from 0.001-50 phr, particularly 0.05-10 phr, more particularly 0.1-10 phr, or even more particularly 0.5-4.0 phr.

The amounts of the functional elastomer of the invention in the resin composition may vary over a wide range and may vary depending on the manufacturing operation or the particular end-use application. Generally, any level of functional elastomer of the invention which produces a desired improvement in mechanical properties is of particular interest. When formulated or combined with a resin composition, the concentration of the functional elastomer of the invention typically ranges from 0.001-10 phr, particularly 0.05-10 phr, more particularly 0.1-10 phr, or even more particularly 0.5-4.0 phr.

In a preferred aspect of the invention, increased mechanical properties may also be obtained for resin compositions comprising at least one cyclic olefin, at least one metal carbene olefin metathesis catalyst, at least one adhesion promoter comprising at least one compound containing at least two isocyanate groups, at least one functional elastomer of the invention, and at least one substrate material, or resin compositions comprising at least one cyclic olefin, at least one metal carbene olefin metathesis catalyst, at least one adhesion promoter comprising at least one compound containing at least two isocyanate groups, and at least one functional elastomer of the invention where the resin composition is applied to at least one substrate material, compared to such resin compositions without the functional elastomer of the invention. For example, the inclusion of a functional elastomer of the invention may provide an improvement in mechanical properties, such as interlaminar shear strength (ILSS) and impact strength or impact toughness compared to the same resin composition that does not contain a functional elastomer of the invention. In particular aspects of the present invention, substrate materials may advantageously comprise an aminosilane-treated substrate.

In another embodiment, resin compositions according to the invention may additionally comprise an exogenous inhibitor. Exogenous inhibitors or "gel modification additives", for use in the present invention are disclosed in U.S. Pat. No. 5,939,504, the contents of which are incorporated herein by reference. In another embodiment, resin compositions according to the invention may additionally comprise a hydroperoxide gel modifier. Hydroperoxide gel modifiers for use in the present invention are disclosed in International Pat. App. No. PCT/US2012/042850, the contents of which are incorporated herein by reference.

Resin compositions of the invention may be optionally formulated with additives. Suitable additives include, but are not limited to, gel modifiers, hardness modulators, antioxidants, antiozonants, stabilizers, crosslinkers, fillers, binders, coupling agents, thixotropes, wetting agents, biocides, plasticizers, pigments, flame retardants, dyes, fibers and reinforcement materials, including sized reinforcements and substrates, such as those treated with finishes, coatings, coupling agents, film formers and/or lubricants. Furthermore, the amount of additives present in the resin compositions may vary depending on the particular type of additive used. The concentration of the additives in the resin compositions typically ranges from, for example, 0.001-85 percent by weight, particularly, from 0.1-75 percent by weight, or even more particularly, from 2-60 percent by weight.

Resin compositions of the invention may be optionally formulated with or without a crosslinker, for example, a crosslinker selected from dialkyl peroxides, diacyl peroxides, and peroxyacids.

Antioxidants and antiozonants include any antioxidant or antiozonant used in the rubber or plastics industry. An "Index of Commercial Antioxidants and Antiozonants, Fourth Edition" is available from Goodyear Chemicals, The Goodyear Tire and Rubber Company, Akron, Ohio 44316. Suitable stabilizers (i.e., antioxidants or antiozonants) include without limitation: 2,6-di-tert-butyl-4-methylphenol (BHT); styrenated phenol, such as Wingstay® S (Goodyear); 2- and 3-tert-butyl-4-methoxyphenol; alkylated hindered phenols, such as Wingstay C (Goodyear); 4-hydroxymethyl-2,6-di-tert-butylphenol; 2,6-di-tert-butyl-4-sec-butylphenol; 2,2'-methylenebis(4-methyl-6-tert-butylphenol); 2,2'-methylenebis(4-ethyl-6-tert-butylphenol); 4,4'-methylenebis(2,6-di-tert-butylphenol); miscellaneous bisphenols, such as Cyanox® 53 (Cytec Industries Inc.) and Permanax WSO; 2,2'-ethylidenebis(4,6-di-tert-butylphenol); 2,2'-methylenebis(4-methyl-6-(1-methylcyclohexyl)phenol); 4,4'-butylidenebis(6-tert-butyl-3-methylphenol); polybutylated Bisphenol A; 4,4'-thiobis(6-tert-butyl-3-methylphenol); 4,4'-methylenebis(2,6-dimethylphenol); 1,1'-thiobis(2-naphthol); methylene bridged polyaklylphenol, such as Ethyl antioxidant 738; 2,2'-thiobis(4-methyl-6-tert-butylphenol); 2,2'-isobutylidenebis(4,6-dimethylphenol); 2,2'-methylenebis(4-methyl-6-cyclohexylphenol); butylated reaction product of p-cresol and dicyclopentadiene, such as Wingstay L; tetrakis(methylene-3,5-di-tert-butyl-4-hydroxyhydrocinnamate)methane, i.e., Irganox® 1010 (BASF); 1,3,5-trimethyl-2,4,6-tris(3,5-di-tert-butyl-4-hydroxybenzyl)benzene, e.g., Ethanox® 330 (Albemarle Corporation); 4,4'-methylenebis (2,6-di-tertiary-butylphenol), e.g., Ethanox 4702 or Ethanox 4710; 1,3,5-tris(3,5-di-tert-butyl-4-hydroxybenzyl)isocyanurate, i.e., Good-rite® 3114 (Emerald Performance Materials), 2,5-di-tert-amylhydroquinone, tert-butylhydroquinone, tris(nonylphenylphosphite), bis(2,4-di-tert-butyl)pentaerythritol) diphosphite, distearyl pentaerythritol diphosphite, phosphited phenols and bisphenols, such as Naugard® 492 (Chemtura Corporation), phosphite/phenolic antioxidant blends, such as Irganox B215; di-n-octadecyl(3,5-di-tert-butyl-4-hydroxybenzyl)phosphonate, such as Irganox 1093; 1,6-hexamethylene bis(3-(3,5-di-tert-butyl-4-hydroxyphenylpropionate), such as Irganox 259, and octadecyl-3,5-di-tert-butyl-4-hydroxyhydrocinnamate, i.e., Irganox 1076, tetrakis(2,4-di-tert-butylphenyl)4,4'-biphenylylenediphosphonite, diphenylamine, and 4,4'-diemthoxydiphenylamine. Such materials are normally employed in the resin composition at levels of about 0.10 phr to 10 phr, but more preferably at levels of about 0.1 phr to 5 phr.

Suitable reinforcing materials include those that add to the strength or stiffness of a polymer composite when incorporated with the polymer. Reinforcing materials can be in the form of filaments, fibers, rovings, mats, weaves, fabrics, knitted material, cloth, or other known structures. Suitable reinforcement materials include glass fibers and fabrics, carbon fibers and fabrics, aramid fibers and fabrics, polyolefin fibers or fabrics (including ultrahigh molecular weight polyethylene fabrics such as those produced by Honeywell under the Spectra® trade name), and polyoxazole fibers or fabrics (such as those produced by the Toyobo Corporation under the Zylon® trade name). Reinforcing materials containing surface finishes, sizings, or coatings are particularly suitable for the described invention including Ahlstrom glass roving (R338-2400), Johns Manville glass roving (Star ROV®-086), Owens Corning rovings (OCV 366-AG-207, R25H-X14-2400, SE1200-207, SE1500-2400, SE2350-250), PPG glass rovings (Hybon® 2002, Hybon® 2026), Toho Tenax® carbon fiber tow (HTR-40), and Zoltek carbon fiber tow (Panex® 35). Furthermore, any fabrics prepared using reinforcing materials containing surface finishes, sizings or coatings are suitable for the invention. Advantageously, the invention does not require the expensive process of removing of surface finishes, sizings, or coatings from the reinforcing materials. Additionally, glass fibers or fabrics may include without limitation A-glass, E-glass or S-glass, S-2 glass, C-glass, R-glass, ECR-glass, M-glass, D-glass, and quartz, and silica/quartz. Preferred glass fiber reinforcements are those with finishes formulated for use with epoxy, vinyl ester, and/or polyurethane resins. When formulated for use with a combination of these resin types, the reinforcements are sometimes described as "multi-compatible." Such reinforcements are generally treated during their manufacture with organosilane coupling agents comprising vinyl, amino, glycidoxy, or methacryloxy functional groups (or various combinations thereof) and are coated with a finish to protect the fiber surface and facilitate handling and processing (e.g., spooling and weaving). Finishes typically comprise a mixture of chemical and polymeric compounds such as film formers, surfactants, and lubricants. Especially preferred glass reinforcements are those containing some amount of amino-functionalized silane coupling agent. Especially preferred finishes are those comprising and epoxy-based and/or polyurethane-based film formers. Examples of preferred glass-fiber reinforcements are those based on Hybon® 2026, 2002, and 2001 (PPG) multi-compatible rovings; Ahlstrom R338 epoxysilane-sized rovings; StarRov® 086 (Johns Manville) soft silane sized multi-compatible rovings; OCV™ 366, SE 1200, and R25H (Owens Corning) multi-compatible rovings; OCV™ SE 1500 and 2350 (Owens Corning) epoxy-compatible rovings; and Jushi Group multi-compatible glass rovings (752 type, 396 type, 312 type, 386 type). Additional suitable polymer fibers and fabrics may include without limitation one or more of polyester, polyamide (for example, NYLON polamide available from E.I. DuPont, aromatic polyamide (such as KEVLAR aromatic polyamide available from E.I. DuPont, or P84 aromatic polyamide available from Lenzing Aktiengesellschaft), polyimide (for example KAPTON polyimide available from E.I. DuPont, polyethylene (for example, DYNEEMA polyethylene from Toyobo Co., Ltd.). Additional suitable carbon fibers may include without limitation AS2C, AS4, AS4C, AS4D, AS7, IM6, IM7, IM9, and PV42/850 from Hexcel Corporation; TORAYCA T300, T300J, T400H, T600S, T700S, T700G, T800H, T800S, T1000G, M35J, M40J, M46J, M50J, M55J, M60J, M30S, M30G and M40 from Toray Industries, Inc.; HTS12K/24K, G30-500 3k/6K/12K, G30-500 12K, G30-700 12K, G30-7000 24K F402, G40-800 24K, STS 24K, HTR 40 F22 24K 1550tex from Toho Tenax, Inc.; 34-700, 34-700WD, 34-600, 34-600WD, and 34-600 unsized from Grafil Inc.; T-300, T-650/35, T-300C, and T-650/35C from Cytec Industries. Additionally suitable carbon fibers may include without limitation AKSACA (A42/D011), AKSACA (A42/D012), Blue Star Starafil (10253512-90), Blue Star Starafil (10254061-130), SGL Carbon (C30 T050 1.80), SGL Carbon (C50 T024 1.82), Grafil (347R1200U), Grafil (THR 6014A), Grafil (THR 6014K), Hexcel Carbon (AS4C/EXP 12K), Mitsubishi (Pyrofil TR 50S 12L AF), Mitsubishi (Pyrofil TR 50S 12L AF), Toho Tenax (T700SC 12000-50C), Toray (T700SC 12000-90C), Zoltek (Panex 35 50K, sizing 11), Zoltek (Panex 35 50K, sizing 13). Additional suitable carbon fabrics may include without limitation Carbon fabrics by Vectorply (C-L 1800) and Zoltek (Panex 35 UD Fabic-PX35UD0500-1220). Additionally suitable glass fabrics may include without limitation glass fabrics as supplied by Vectorply (E-LT 3500-10) based on PPG Hybon® 2026; Saertex (U14EU970-01190-T2525-125000) based on PPG Hybon® 2002; Chongqing Polycomp Internation Corp. (CPIC® Fiberglass) (EKU 1150(0)/50-600); and Owens Corning (L1020/07A06 Xweft 200tex).

Other suitable fillers include, for example, metallic density modulators, microparticulate density modulators, such as, for example, microspheres, and macroparticulate density modulators, such as, for example, glass or ceramic beads. Metallic density modulators include, but are not limited to, powdered, sintered, shaved, flaked, filed, particulated, or granulated metals, metal oxides, metal nitrides, and/or metal carbides, and the like. Preferred metallic density modulators include, among others, tungsten, tungsten carbide, aluminum, titanium, iron, lead, silicon oxide, aluminum oxide, boron carbide, and silicon carbide. Microparticulate density modulators include, but are not limited to, glass, metal, thermoplastic (either expandable or pre-expanded) or thermoset, and/or ceramic/silicate microspheres. Macroparticulate density modulators include, but are not limited to, glass, plastic, or ceramic beads; metal rods, chunks, pieces, or shot; hollow glass, ceramic, plastic, or metallic spheres, balls, or tubes; and the like.

The invention is also directed to articles manufactured from a resin composition comprising at least one cyclic olefin, at least one metal carbene olefin metathesis catalyst, at least one adhesion promoter comprising at least one compound containing at least two isocyanate groups, at least one functional elastomer of the invention, and at least one substrate material. Additionally, the invention is directed to articles manufactured from a resin composition comprising at least one cyclic olefin, at least one metal carbene olefin metathesis catalyst, at least one adhesion promoter comprising at least one compound containing at least two isocyanate groups, and at least one functional elastomer of the invention, where the resin composition is combined with at least one metal carbene olefin metathesis catalyst, and the resulting resin composition is applied to at least one substrate, which may be, for example, a functionalized substrate, such as, for example, a heteroatom-functionalized substrate, such as, for example, an amino-functionalized substrate. Articles may include, but are not limited to, those formed by standard manufacturing techniques including casting, centrifugal casting, pultrusion, molding, rotational molding, open molding, reaction injection molding (RIM), resin transfer molding (RTM), pouring, vacuum impregnation, surface coating, filament winding and other methods known to be useful for production of polymer articles. Molded parts include but are not limited to reaction injection molding, resin transfer molding, and vacuum assisted resin transfer molding. Furthermore, the compositions and articles of manufacture of the invention are not limited to a single polymer-surface interface but include also multilayers and laminates containing multiple polymer-surface interfaces. The invention is also suitable for manufacture of articles by the infusion of the resin into a porous material. Such porous materials include but are not limited to wood, cement, concrete, open-cell and reticulated foams and sponges, papers, cardboards, felts, ropes or braids of natural or synthetic fibers, and various sintered materials. Additionally, other manufacturing techniques include without limitation cell casting, dip casting, continuous casting, embedding, potting, encapsulation, film casting or solvent casting, gated casting, mold casting, slush casting, extrusion, mechanical foaming, chemical foaming, physical foaming, compression molding or matched die molding, spray up, Vacuum Assisted Resin Transfer Molding (VARTM), Seeman's Composite Resin Infusion Molding Process (SCRIMP), blow molding, in mold coating, in-mold painting or injection, vacuum forming, Reinforced Reaction Injection Molding (RRIM), Structural Reaction Injection Molding (SRIM), thermal expansion transfer molding (TERM), resin injection recirculation molding (RICM), controlled atmospheric pressure resin infusion (CAPRI), hand-layup. For manufacturing techniques requiring the use of a RIM or impingement style mixhead, including without limitation RIM, SRIM, and RRIM, articles of manufacture may be molded using a single mixhead or a plurality of mixheads as well as a plurality of material injection streams (e.g., two resin streams and one catalyst stream).

Furthermore, the present invention also allows for the making of articles of manufacture of any configuration, weight, size, thickness, or geometric shape. Examples of articles of manufacture include without limitation any molded or shaped article for use as an aerospace component, a marine component, an automotive component, a sporting goods component, an electrical component, and industrial component, medical component, dental component, or military component. In one embodiment an article may be a turbine component used on aircraft or general power generation. In one embodiment, turbine components may include without limitation one or more of an inlet, pylon, pylon fairing, an acoustic panel, a thrust reverser panel, a fan blade, a fan containment case, a bypass duct, an aerodynamic cowl, or an airfoil component. In one embodiment, an article may be a turbine blade component or may be a turbine blade. In one embodiment, an article may be a wind rotor blade, tower, spar cap, or nacelle for wind turbines. In one embodiment, an article may be an airframe component. Examples of aerospace components may include without limitation one or more of fuselage skin, wing, fairing, doors, access panel, aerodynamic control surface, or stiffener. In one embodiment an article may be an automotive component. Examples of automotive components may include without limitation one or more of body panel, fender, spoiler, truck bad, protective plate, hood, longitudinal rail, pillar, or door. Examples of industrial components may include without limitation one or more of risers platforms, impact protection structures for oil and gas; bridges, pipes, pressure vessels, power poles, coils, containers, tanks, liners, containment vessels, articles for application in corrosive environments (e.g., chlor-alkali, caustic, acidic, brine, etc.), reinforcement structures for concrete architectures and roads, or radiators. Examples of electrical components may include without limitation one or more wound articles, such as coils or electric motors, or insulating devices. In one embodiment, an article may be an eddy-current shielding component of a magnetic resonance imaging system or shielding component for any electromagnetic radiation. In one embodiment, an article may be a military component including without limitation ballistics resistant armor for personnel or vehicles, or ballistics resistant structures for protecting personnel or equipment. In one embodiment, an article may be a sporting goods component including without limitation an arrow shaft, a tennis racket frame, a hockey stick, compound bow limbs, or a golf club shaft.

Resin compositions according to the invention may further comprise a sizing composition, or be used to provide improved adhesion to substrate materials that are sized with certain commercial silanes commonly used in the industry. As is known in the art, glass fibers are typically treated with a chemical solution (e.g., a sizing composition) soon after their formation to reinforce the glass fibers and protect the strands' mechanical integrity during processing and composite manufacture. Sizing treatments compatible with metal carbene olefin metathesis catalysts and polydicyclopentadiene composites have been described in U.S. Pat. Nos. 6,890,650 and 6,436,476, the disclosures of both of which are incorporated herein by reference. However, these disclosures are based on the use of specialty silane treatments that are not commonly used in industrial glass manufacture. By comparison, the current invention may provide improved mechanical properties for polymer-glass composites that are sized with silanes commonly used in the industry.

Glass sizing formulations typically comprise at least one film former (typically a film forming polymer), at least one silane, and at least one lubricant. Any components of a sizing formulation that do not interfere with or substantially decrease the effectiveness of the metal carbene olefin metathesis catalyst or olefin polymerization reaction are considered to be compatible with the current invention and may generally be used herein.

Film formers that are compatible with ROMP catalysts (metal carbene olefin metathesis catalysts) include epoxies, polyesters, polyurethanes, polyolefins, and/or polyvinyl acetates. Other common film formers that do not adversely affect the performance of the metal carbene olefin metathesis catalyst may also be used. Film formers are typically used as nonionic, aqueous emulsions. More than one film former may be used in a given sizing formulation, to achieve a desired balance of glass processability and composite mechanical properties.

More particularly, the film former may comprise a low molecular weight epoxy emulsion, defined as an epoxy monomer or oligomer with an average molecular weight per epoxide group (EEW) of less than 500, and/or a high molecular weight epoxy emulsion, defined as an epoxy monomer or oligomer with an average molecular weight per epoxide group (EEW) of greater than 500. Examples of suitable low molecular weight products include aqueous epoxy emulsions produced by Franklin International, including Franklin K8-0203 (EEW 190) and Franklin E-102 (EEW 225-275). Other examples of low molecular weight epoxy emulsions are available from Hexion, including EPI-REZ™ 3510-W-60 (EEW 185-215), and EPI-REZ™ 3515-W-60 (EEW 225-275). Further examples of low molecular weight epoxy emulsions are available from COIM, including Filco 309 (EEW 270) and Filco 306 (EEW 330). Further examples of low molecular weight epoxy emulsions are available from DSM, including Neoxil® 965 (EEW 220-280) and Neoxil® 4555 (EEW 220-260). Examples of suitable high molecular weight epoxy emulsion products include epoxy emulsions produced by Hexion, including EPI-REZ™ 3522-W-60 (EEW 615-715).

Aqueous emulsions of modified epoxies, polyesters, and polyurethanes may also be used in the film former. Examples of suitable modified epoxy products include emulsions produced by DSM, including Neoxil® 2626 (a plasticized epoxy with an EEW of 500-620), Neoxil® 962/D (an epoxy-ester with an EEW of 470-550), Neoxil® 3613 (an epoxy-ester with an EEW of 500-800), Neoxil® 5716 (an epoxy-novolac with an EEW of 210-290), Neoxil® 0035 (a plasticized epoxy-ester with an EEW of 2500), and Neoxil® 729 (a lubricated epoxy with an EEW of 200-800). Further examples of modified epoxy emulsions are available from COIM, including Filco 339 (an unsaturated polyester-epoxy with an EEW of 2000) and Filco 362 (an epoxy-ester with an EEW of 530). Examples of suitable polyester products include emulsions produced by DSM, including Neoxil® 954/D, Neoxil® 2635, and Neoxil® 4759 (unsaturated bisphenolic polyesters). Additional suitable products from DSM include Neoxil® 9166 and Neoxil® 968/60 (adipate polyesters). Further examples of suitable products include emulsions produced by COIM, including Filco 354/N (unsaturated bisphenolic polyester), Filco 350 (unsaturated polyester), and Filco 368 (saturated polyester). Examples of suitable polyurethane products include emulsions produced by Bayer Material Science, including Baybond® 330 and Baybond® 401.

The film former may also comprise polyolefins or polyolefin-acrylic copolymers, polyvinylacetates, modified polyvinylacetates, or polyolefin-acetate copolymers. Suitable polyolefins include, but are not limited to, polyethylenes, polypropylenes, polybutylenes, and copolymers thereof, and the polyolefins may be oxidized, maleated, or otherwise treated for effective film former use. Examples of suitable products include emulsions produced by Michelman, including Michem® Emulsion 91735, Michem® Emulsion 35160, Michem® Emulsion 42540, Michem® Emulsion 69230, Michem® Emulsion 34040M1, Michem® Prime 4983R, and Michem® Prime 4982SC. Examples of suitable products include emulsions produced by HB Fuller, including PD 708H, PD 707, and PD 0166. Additional suitable products include emulsions produced by Franklin International, including Duracet® 637. Additional suitable products include emulsions produced by Celanese, including Vinamul® 8823 (plasticized polyvinylacetate), Dur-O-Set® E-200 (ethylene-vinyl acetate copolymer), Dur-O-Set® TX840 (ethylene-vinyl acetate copolymer), and Resyn® 1971 (epoxy-modified polyvinylacetate).

While not limited thereto, preferred film formers include low- and high-molecular weight epoxies, saturated and unsaturated polyesters, and polyolefins, such as Franklin K80-203, Franklin E-102, Hexion 3510-W-60, Hexion 3515-W-60, and Michelman 35160.

Nonionic lubricants may also be added to the sizing composition. Suitable nonionic lubricants that are compatible with ROMP compositions include esters of polyethylene glycols and block copolymers of ethylene oxide and propylene oxide. More than one nonionic lubricant may be used in a given sizing formulation if desired, e.g., to achieve a desired balance of glass processability and composite mechanical properties.

Suitable lubricants may contain polyethylene glycol (PEG) units with an average molecular weight between 200 and 2000, preferably between 200-600. These PEG units can be esterified with one or more fatty acids, including oleate, tallate, laurate, stearate, and others. Particularly preferred lubricants include PEG 400 dilaurate, PEG 600 dilaurate, PEG 400 distearate, PEG 600 distearate, PEG 400 dioleate, and PEG 600 dioleate. Examples of suitable products include compounds produced by BASF, including MAPEG® 400 DO, MAPEG® 400 DOT, MAPEG® 600 DO, MAPEG® 600 DOT, and MAPEG® 600 DS. Additional suitable products include compounds produced by Zschimmer & Schwarz, including Mulsifan 200 DO, Mulsifan 400 DO, Mulsifan 600 DO, Mulsifan 200 DL, Mulsifan 400 DL, Mulsifan 600 DL, Mulsifan 200 DS, Mulsifan 400 DS, and Mulsifan 600 DS. Additional suitable products include compounds produced by Cognis, including Agnique® PEG 300 DO, Agnique® PEG 400 DO, and Agnique® PEG 600 DO.

Suitable nonionic lubricants also include block copolymers of ethylene oxide and propylene oxide. Examples of suitable products include compounds produced by BASF, including Pluronic® L62, Pluronic® L101, Pluronic® P103, and Pluronic® P105.

Cationic lubricants may also be added to the sizing composition. Cationic lubricants that are compatible with ROMP include modified polyethyleneimines, such as Emery 6760L produced by Pulcra Chemicals.

Silane coupling agent may optionally be added to the sizing composition, non-limiting examples including, methacrylate, acrylate, amino, or epoxy functionalized silanes along with alkyl, alkenyl, and norbomenyl silanes.

Optionally, the sizing composition may contain one or more additives for modifying the pH of the sizing resin. One preferred pH modifier is acetic acid.

The sizing composition may optionally contain other additives useful in glass sizing compositions. Such additives may include emulsifiers, defoamers, cosolvents, biocides, antioxidants, and additives designed to improve the effectiveness of the sizing composition. The sizing composition can be prepared by any method and applied to substrate materials for use herein, such as glass fibers or fabric, by any technique or method.

In a preferred embodiment, the metathesis reactions disclosed herein are carried out under a dry, inert atmosphere. Such an atmosphere may be created using any inert gas, including such gases as nitrogen and argon. The use of an inert atmosphere is optimal in terms of promoting catalyst activity, and reactions performed under an inert atmosphere typically are performed with relatively low catalyst loading. The reactions disclosed herein may also be carried out in an oxygen-containing and/or a water-containing atmosphere, and in one embodiment, the reactions are carried out under ambient conditions. The presence of oxygen or water in the reaction may, however, necessitate the use of higher catalyst loadings as compared with reactions performed under an inert atmosphere. Where the vapor pressure of the reactants allows, the reactions disclosed herein may also be carried out under reduced pressure.

The reactions disclosed herein may be carried out in a solvent, and any solvent that is inert towards cross-metathesis may be employed. Generally, solvents that may be used in the metathesis reactions include organic, protic, or aqueous solvents, such as aromatic hydrocarbons, chlorinated hydrocarbons, ethers, aliphatic hydrocarbons, alcohols, water, or mixtures thereof. Example solvents include benzene, toluene, p-xylene, methylene chloride, 1,2-dichloroethane, dichlorobenzene, chlorobenzene, tetrahydrofuran, diethyl ether, pentane, methanol, ethanol, water, or mixtures thereof. In a preferred embodiment, the reactions disclosed herein are carried out neat, i.e., without the use of a solvent.

It will be appreciated that the temperature at which a metathesis reaction according to methods disclosed herein is conducted can be adjusted as needed, and may be at least about −78° C., −40° C., −10° C., 0° C., 10° C., 20° C., 25° C., 35° C., 50° C., 70° C., 100° C., or 150° C., or the temperature may be in a range that has any of these values as the upper or lower bounds. In a preferred embodiment, the reactions are carried out at a temperature of at least about 35° C., and in another preferred embodiment, the reactions are carried out at a temperature of at least about 50° C.

It is to be understood that while the invention has been described in conjunction with specific embodiments thereof, the description above as well as the examples that follow are intended to illustrate and not limit the scope of the invention. Other aspects, advantages, and modifications within the scope of the invention will be apparent to those skilled in the art to which the invention pertains.

EXPERIMENTAL

In the following examples, efforts have been made to ensure accuracy with respect to numbers used (e.g., amounts, temperature, etc.) but some experimental error and deviation should be accounted for. Unless indicated otherwise, temperature is in degrees Celsius (° C.), pressure is at or near atmospheric, viscosity is in centipoise (cP).

The following examples are to be considered as not being limiting of the invention as described herein, and are instead provided as representative examples of the impact modified compositions of the invention and the methods for their use.

EXAMPLES

Materials and Methods

All glassware was oven dried and reactions were performed under ambient conditions unless otherwise noted. All solvents and reagents were purchased from commercial suppliers and used as received unless otherwise noted.

Dicyclopentadiene (Ultrene® 99) (DCPD) was obtained from Cymetech Corporation. A modified DCPD base resin containing 20-25% tricyclopentadiene (and small amounts of higher cyclopentadiene homologs) was prepared by heat treatment of Ultrene® 99 generally as described in U.S. Pat. No. 4,899,005.

Liquid MDI (50/50 mixture of 4,4'-MDI and 2,4'-MDI) was used as received from Bayer Material Science (Mondur® MLQ) and was used where indicated. Ethanox® 4702 antioxidant (4,4'-methylenebis(2,6-di-tertiary-butylphenol), Albemarle Corporation) was used where indicated. Crystal Plus 70FG mineral oil, containing 2 phr Cab-o-sil TS610, was used to prepare the metal carbene olefin metathesis catalyst suspensions. Triphenylphosphine (TPP) was used as received from Arkema.

A series of styrene-ethylene/butylene-styrene (SEBS) hydrogenated copolymer impact modifiers were evaluated. These impact modifiers were obtained from Kraton Performance Polymers and used as received. According to data sheets and product brochures available from the manufacturer, Kraton Performance Polymers, and information provided on the manufacturer's website (www.kraton.com), the compositions of the evaluated impact modifiers are summarized in Table 1. Kraton FG1901G and FG1924G are linear styrenic triblock copolymers with a hydrogenated midblock of styrene-ethylene/butylene-styrene containing the indicated wt. % maleic anhydride grafted onto the midblock. Kraton G1650M and G1657M are linear styrenic triblock copolymers with a hydrogenated midblock of styrene-ethylene/butylene-styrene. According to the manufacturer's data sheets and product brochures for Kraton FG1901G, Kraton FG1924G, Kraton G1657M, and Kraton G1650M in the grade nomenclature "G" indicates Kraton G hydrogenated styrenic block copolymers and "FG" denotes functionalized Kraton G. Styrene-ethylene/butylene-styrene hydrogenated copolymers (Kraton G1657M and Kraton G1650M) and maleic anhydride grafted styrene-ethylene/butylene-styrene hydrogenated copolymers (Kraton FG1924G and Kraton FG1901G) were dissolved in modified DCPD (containing 20-25% tricyclopentadiene) by heating at approximately 52° C. with stirring under nitrogen.

TABLE 1

Impact Modifiers

| Product Name | Styrene Content | Functionality | Functional Content |
|---|---|---|---|
| Kraton G1650M | 30% | None | None |
| Kraton G1657M | 13% | None | None |
| Kraton FG1901G | 30% | Maleic anhydride | 1.4-2.0 wt. % |
| Kraton FG1924G | 13% | Maleic anhydride | 0.7-1.3 wt. % |

Metal carbene olefin metathesis catalysts were prepared by standard methods and include [1,3-bis-(2,4,6-trimethylphenyl)-2-imidazolidinylidene]dichloro(3-methyl-2-butenylidene) (tricyclohexylphosphine) ruthenium(II) (C827).

Glass fabrics were used as supplied by Vectorply (E-LT 3500-10) based on PPG Hybon® 2026 ("Vectorply Glass Fabric"); Saertex (U14EU970-01190-T2525-125000) based on PPG Hybon® 2002 ("Saertex Glass Fabric"); Chongqing Polycomp Internation Corp. (CPIC® Fiberglass) (EKU 1150 (0)/50-600) ("CPIC Glass Fabric"); Owens Corning (L1020/07A06 Xweft 200tex) ("OC Glass Fabric").

Carbon fabrics were used as supplied by Vectorply (C-L 1800) ("Vectorply Carbon Fabric"); Zoltek (Panex 35 UD Fabic-PX35UD0500-1220) ("Zoltek Carbon Fabric").

Additives to the resin are reported as ppm, which is defined as the weight in grams of additive per million grams of resin, or as phr, which is defined as the weight in grams of the additive per hundred grams of resin.

The glass composite laminates of the examples in Tables 1-6 presented below herein were prepared using the VARTM process. The bottom mold surface of the composite laminate consisted of a sealed and release-treated aluminum plate. The aluminum plate possessed inlet and outlet ports mechanically affixed to the bottom surface of the aluminum plate for resin infusion and vacuum source attachment, respectively. The glass composite laminates were constructed by cutting and arranging four plies of glass fabric, each ply having dimensions of 3"×6", on the top surface of the aluminum plate to achieve a ⅛" laminate thickness. A peel ply (Bron Aerotech; PTFE-coated) was placed over the four plies of glass fabric reinforcement material. Nylon resin distribution media (Airtech Greenflow 75) was positioned on top of the peel ply at opposite ends of the composite laminate corresponding to the position of the inlet port and outlet port, respectively. A sheet of vacuum bagging film (Umeco Process Materials Stretch-Vac 2000) was placed over the completed layup. The vacuum bagging film was affixed to the mold surface using sealant tape (Airtech AT200-Y tape) and a vacuum was applied to the outlet port to evacuate air from the layup to a vacuum level of between 28 inches-Hg to 29 inches-Hg. Resin prepared as per the examples presented below herein was degassed under vacuum with stirring for at least 20 minutes. Catalyst suspension was injected into the resin under vacuum and the catalyzed resin was stirred under vacuum for at least one minute. The resin and catalyst suspension were at ambient temperature (20-25° C.) immediately prior to mixing. After at least one minute, stirring of the catalyzed resin was stopped, the vacuum source was clamped off, and the catalyzed resin was backfilled with argon. The catalyzed resin was then infused in to the glass fabric, driven by the pressure gradient between the ambient pressure and the evacuated glass fabric layup. After the infusion was complete, the glass composite laminate was heated from ambient temperature (20-25° C.) to 35° C. for two hours. After two hours at 35° C. the glass composite laminate was heated to 100° C. at a heating rate of 1° C./min and held at 100° C. for 1 hour and then allowed to cool to ambient temperature (20-25° C.) and subsequently demolded.

The carbon composite laminates of the examples in Tables 1-6 presented below herein were prepared similarly using six plies of carbon fabric to achieve a ⅛" laminate thickness.

The mechanical properties were measured using standard techniques. Interlaminar shear strength (ILSS) at 10% strain was measured by the short-beam shear method according to ASTM D2344 on 1"×¼"×⅛" samples. The ILSS values were reported in units of pounds per square inch (psi). Interlaminar shear strength (ILSS) is a measure of the adhesion and/or compatibility between polymer matrix and fiber reinforcement in a composite. Reported ILSS values are the average of 3 samples. The following criteria, based on interlaminar shear strength values, was used to characterize the adhesion and/or compatibility between the polymer matrix and the glass or carbon fiber reinforcement materials. Composites having poor adhesion and/or compatibility between the polymer matrix and fiber reinforcement were characterized as having ILSS values less than 7,500 psi suggesting a lack of covalent adhesion between the polymer matrix and fiber reinforcement. Composites having ILSS values less than 7,500 psi are indicated with a negative sign (−) in Table 2 herein. Composites having superior adhesion and/or compatibility between the polymer matrix and fiber reinforcement were characterized as having ILSS values greater than or equal to 7,500 psi suggesting a higher degree of covalent adhesion between the polymer matrix and fiber reinforcement. Composites having ILSS greater than or equal to 7,500 psi are indicated with a positive sign (+) in Table 2 herein. All ILSS samples were stored and tested at ambient room conditions. Impact strength was measured using Notched Izod pendulum impact resistance was tested according to ASTM D256 using 2.5"×½"×¼" samples. The Notched Izod values were reported in units of ft-lbf/in. Reported Notched Izod values are the average of 5 samples and are reported in Table 3 herein. All Notched Izod samples were stored and tested at ambient room conditions.

Examples 1(a)-(f)

ILSS of Glass and Carbon Composites Prepared by VARTM

The modified DCPD (containing 20-25% tricyclopentadiene) was formulated with 0.6 phr TPP, 2 phr Ethanox® 4702 antioxidant. The resin was catalyzed by the addition of C827 (monomer to catalyst ratio 45,000:1) in a suspension of mineral oil. VARTM samples were prepared using commercial glass fabrics and commercial carbon fabrics as described above herein. The composite laminates were cured as described above herein. The ILSS of the resulting composites are shown in (Table 2).

Examples 2(a)-(f)

ILSS of Glass and Carbon Composites Prepared by VARTM

The modified DCPD (containing 20-25% tricyclopentadiene) was formulated with 0.6 phr TPP, 2 phr Ethanox®

4702 antioxidant, and 2 phr MDI (Mondur® MLQ). The resin was catalyzed by the addition of C827 (monomer to catalyst ratio 45,000:1) in a suspension of mineral oil. VARTM samples were prepared using commercial glass fabrics and commercial carbon fabrics as described above herein. The composite laminates were cured as described above herein. The ILSS of the resulting composites are shown in (Table 2).

Examples 3(a)-(f)

ILSS of Glass and Carbon Composites Prepared by VARTM

The modified DCPD (containing 20-25% tricyclopentadiene) was formulated with 0.6 phr TPP, 2 phr Ethanox® 4702 antioxidant, 2 phr MDI (Mondur® MLQ), and 1 phr styrene-ethylene/butylene-styrene hydrogenated copolymer (Kraton G1657M). The resin was catalyzed by the addition of C827 (monomer to catalyst ratio 45,000:1) in a suspension of mineral oil. VARTM samples were prepared using commercial glass fabrics and commercial carbon fabrics as described above herein. The composite laminates were cured as described above herein. The ILSS of the resulting composites are shown in (Table 2).

Examples 4(a)-(f)

ILSS of Glass and Carbon Composites Prepared by VARTM

The modified DCPD (containing 20-25% tricyclopentadiene) was formulated with 0.6 phr TPP, 2 phr Ethanox® 4702 antioxidant, 2 phr MDI (Mondur® MLQ), and 1 phr maleic anhydride grafted styrene-ethylene/butylene-styrene hydrogenated copolymer (Kraton FG1924G). The resin was catalyzed by the addition of C827 (monomer to catalyst ratio 45,000:1) in a suspension of mineral oil. VARTM samples were prepared using commercial glass fabrics and commercial carbon fabrics as described above herein. The composite laminates were cured as described above herein. The ILSS of the resulting composites are shown in (Table 2).

Examples 5(a)-(f)

ILSS of Glass and Carbon Composites Prepared by VARTM

The modified DCPD (containing 20-25% tricyclopentadiene) was formulated with 0.6 phr TPP, 2 phr Ethanox® 4702 antioxidant, 2 phr MDI (Mondur® MLQ), and 1 phr styrene-ethylene/butylene-styrene hydrogenated copolymer (Kraton G1650M). The resin was catalyzed by the addition of C827 (monomer to catalyst ratio 45,000:1) in a suspension of mineral oil. VARTM samples were prepared using commercial glass fabrics and commercial carbon fabrics as described above herein. The composite laminates were cured as described above herein. The ILSS of the resulting composites are shown in (Table 2).

Examples 6(a)-(f)

ILSS of Glass and Carbon Composites Prepared by VARTM

The modified DCPD (containing 20-25% tricyclopentadiene) was formulated with 0.6 phr TPP, 2 phr Ethanox® 4702 antioxidant, 2 phr MDI (Mondur® MLQ), and 1 phr maleic anhydride grafted styrene-ethylene/butylene-styrene hydrogenated copolymer (Kraton FG1901G). The resin was catalyzed by the addition of C827 (monomer to catalyst ratio 45,000:1) in a suspension of mineral oil. VARTM samples were prepared using commercial glass fabrics and commercial carbon fabrics as described above herein. The composite laminates were cured as described above herein. The ILSS of the resulting composites are shown in (Table 2).

TABLE 2

| | ILSS | | | | | |
|---|---|---|---|---|---|---|
| Example | Vectorply Carbon Fabric (a) | Zoltek Carbon Fabric (b) | Vectorply Glass Fabric (c) | Saertex Glass Fabric (d) | OC Glass Fabric (e) | CPIC Glass Fabric (f) |
| 1 | (−) | (−) | (−) | (−) | (−) | (−) |
| 2 | (+) | (−) | (+) | (−) | (+) | (+) |
| 3 | (−) | (−) | (−) | (−) | Not tested | (−) |
| 4 | (+) | (+) | (+) | (+) | (+) | Not tested |
| 5 | (+) | (−) | (+) | (−) | Not tested | (+) |
| 6 | (+) | (+) | (+) | (+) | (+) | Not tested |

Examples 7(a)-11(a)

Notched Izod Values of Molded Polymer Plaques

The modified DCPD (containing 20-25% tricyclopentadiene) was formulated with 0.6 phr TPP, 2 phr Ethanox® 4702 antioxidant, 2 phr MDI (Mondur® MLQ), and 1 phr of the appropriate impact modifier (Kraton G1657M or Kraton G1650M) or appropriate functional elastomer (Kraton FG1924G or Kraton FG1901G). The resin was catalyzed by the addition of C827 (monomer to catalyst ratio 45,000:1) in a suspension of mineral oil. The resin and catalyst suspension were at ambient temperature (20-25° C.) immediately prior to mixing. The catalyzed resin was stirred and poured into an aluminum mold having a 6"×4"×¼" cavity. The aluminum mold was at ambient temperature (20-25° C.) immediately before addition of the catalyzed resin. The aluminum mold containing the catalyzed resin was placed in a laboratory oven and heated from ambient temperature (20-25° C.) to 35° C. for two hours, then to 100° C. at a heating rate of 1° C./min and held at 100° C. for 1 hour and then allowed to cool to ambient temperature (20-25° C.) at which point the molded polymer plaques were demolded. The notched izod values of the molded polymer plaques are shown in (Table 3).

TABLE 3

| Notched Izod (ft-lbf/in) | | | | |
|---|---|---|---|---|
| Example | | | | |
| 7 No Impact Modifier No Functional Elastomer | 8 Impact Modifier Kraton G1657M | 9 Functional Elastomer Kraton FG1924G | 10 Impact Modifier Kraton G1650M | 11 Functional Elastomer Kraton FG1901G |
| a 0.62 | 0.78 | 0.91 | 0.83 | 0.93 |

The claimed invention is:

1. A composition, comprising:
   at least one cyclic olefin;
   at least one metal carbene olefin metathesis catalyst;
   at least one adhesion promoter comprising at least one compound containing at least two isocyanate groups; and
   at least one functional elastomer, wherein the at least one functional elastomer is a maleic anhydride grafted styrene-ethylene/butylene-styrene hydrogenated copolymer.

2. The composition of claim 1, further comprising at least one substrate material.

3. The composition of claim 1, wherein the at least one cyclic olefin is selected from strained cyclic olefins, unstrained cyclic olefins, acyclic olefins, dienes, and unsaturated polymers, or combinations thereof, wherein the cyclic olefin may contain a functional group, or be substituted with a group, selected from halogen, hydroxyl, hydrocarbyl, alkoxy, alkenyloxy, alkynyloxy, aryloxy, aralkyloxy, alkaryloxy, acyl, acyloxy, alkoxycarbonyl, alkylcarbonato, arylcarbonato, carboxy, carboxylato, carbamoyl, alkyl-substituted carbamoyl, haloalkyl-substituted carbamoyl, aryl-substituted carbamoyl, thiocarbamoyl alkyl-substituted thiocarbamoyl, aryl-substituted thiocarbamoyl, carbamido, cyano, cyanato, thiocyanato, formyl, thioformyl, amino, alkyl-substituted amino, aryl-substituted amino, alkylamido, arylamido, imino, alkylimino, arylimino, nitro, nitroso, sulfo, sulfonato, alkylsulfanyl, arylsulfanyl, alkylsulfinyl, arylsulfinyl, alkylsulfonyl, alkylaminosulfonyl, arylsulfonyl, boryl, borono, boronato, phosphono, phosphonato, phosphinato, phospho, phosphino, or a combination thereof.

4. The composition of claim 1, wherein the at least one metal carbene olefin metathesis catalyst is a Group 8 transition metal complex having the structure of formula (I)

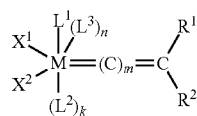

(I)

in which:
   M is a Group 8 transition metal;
   $L^1$, $L^2$, and $L^3$ are independently selected from neutral electron donor ligands;
   n is 0 or 1, such that $L^3$ may or may not be present;
   m is 0, 1, or 2;
   k is 0 or 1;
   $X^1$ and $X^2$ are independently anionic ligands; and
   $R^1$ and $R^2$ are independently selected from hydrogen, hydrocarbyl, substituted hydrocarbyl, heteroatom-containing hydrocarbyl, substituted heteroatom-containing hydrocarbyl, and functional groups; wherein one or both of $R^1$ and $R^2$ may have the structure $-(W)_n-U^+V^-$, in which W is selected from hydrocarbylene, substituted hydrocarbylene, heteroatom-containing hydrocarbylene, or substituted heteroatom-containing hydrocarbylene; U is a positively charged Group 15 or Group 16 element substituted with hydrogen, hydrocarbyl, substituted hydrocarbyl, heteroatom-containing hydrocarbyl, or substituted heteroatom-containing hydrocarbyl; V is a negatively charged counterion; and n is zero or 1,
   wherein any two or more of $X^1$, $X^2$, $L^1$, $L^2$, $L^3$, $R^1$, and $R^2$ can be taken together to form one or more cyclic groups, and further wherein any one or more of $X^1$, $X^2$, $L^1$, $L^2$, $L^3$, $R^1$, and $R^2$ may be attached to a support.

5. The composition of claim 1, wherein the at least one compound containing at least two isocyanate groups is a compound selected from hydrocarbyl, substituted hydrocarbyl, heteroatom-containing hydrocarbyl, substituted heteroatom-containing hydrocarbyl, functionalized hydrocarbyl compounds, or mixtures thereof.

6. The composition of claim 1, wherein the at least one compound containing at least two isocyanate groups is selected from at least one diisocyanate, triisocyanate, polyisocyanate compound, or mixtures thereof.

7. The composition of claim 1, wherein the at least one compound containing at least two isocyanate groups is a diisocyanate compound or mixtures thereof.

8. A method for improving the adhesion of a resin composition to a substrate material, comprising:
   combining at least one cyclic olefin, at least one metal carbene olefin metathesis catalyst, at least one adhesion promoter comprising at least one compound containing at least two isocyanate groups, and at least one functional elastomer to form a resin composition,
   contacting the resin composition with the substrate material, and
   subjecting the resin composition to conditions effective to promote an olefin metathesis reaction of the cyclic olefin,
   wherein the at least one functional elastomer is a maleic anhydride grafted styrene-ethylene/butylene-styrene hydrogenated copolymer.

9. The method of claim 8, wherein the at least one cyclic olefin is selected from strained cyclic olefins, unstrained cyclic olefins, acyclic olefins, dienes, and unsaturated polymers, or combinations thereof, wherein the cyclic olefin may contain a functional group, or be substituted with a group, selected from halogen, hydroxyl, hydrocarbyl, alkoxy, alkenyloxy, alkynyloxy, aryloxy, aralkyloxy, alkaryloxy, acyl, acyloxy, alkoxycarbonyl, alkylcarbonato, arylcarbonato, carboxy, carboxylato, carbamoyl, alkyl-substituted carbamoyl, haloalkyl-substituted carbamoyl, aryl-substituted carbamoyl, thiocarbamoyl alkyl-substituted thiocarbamoyl, aryl-substituted thiocarbamoyl, carbamido, cyano, cyanato, thiocyanato, formyl, thioformyl, amino, alkyl-substituted amino, aryl-substituted amino, alkylamido, arylamido, imino, alkylimino, arylimino, nitro, nitroso, sulfo, sulfonato, alkylsulfanyl, arylsulfanyl, alkylsulfinyl, arylsulfinyl, alkylsulfonyl, alkylaminosulfonyl, arylsulfonyl, boryl, borono, boronato, phosphono, phosphonato, phosphinato, phospho, phosphino, or a combination thereof.

10. The method of claim 8, wherein the at least one metal carbene olefin metathesis catalyst is a Group 8 transition metal complex having the structure of formula (I)

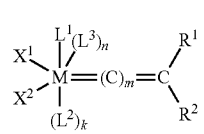

(I)

in which:
M is a Group 8 transition metal;
$L^1$, $L^2$, and $L^3$ are independently selected from neutral electron donor ligands;
n is 0 or 1, such that $L^3$ may or may not be present;
m is 0, 1, or 2;
k is 0 or 1;
$X^1$ and $X^2$ are independently anionic ligands; and
$R^1$ and $R^2$ are independently selected from hydrogen, hydrocarbyl, substituted hydrocarbyl, heteroatom-containing hydrocarbyl, substituted heteroatom-containing hydrocarbyl, and functional groups; wherein one or both of $R^1$ and $R^2$ may have the structure —$(W)_n$—$U^+V^-$, in which W is selected from hydrocarbylene, substituted hydrocarbylene, heteroatom-containing hydrocarbylene, or substituted heteroatom-containing hydrocarbylene; U is a positively charged Group 15 or Group 16 element substituted with hydrogen, hydrocarbyl, substituted hydrocarbyl, heteroatom-containing hydrocarbyl, or substituted heteroatom-containing hydrocarbyl; V is a negatively charged counterion; and n is zero or 1,
wherein any two or more of $X^1$, $X^2$, L, $L^2$, $L^3$, $R^1$, and $R^2$ can be taken together to form one or more cyclic groups, and further wherein any one or more of $X^1$, $X^2$, $L^1$, $L^2$, $L^3$, $R^1$, and $R^2$ may be attached to a support.

11. The method of claim 8, wherein the at least one compound containing at least two isocyanate groups is a compound selected from hydrocarbyl, substituted hydrocarbyl, heteroatom-containing hydrocarbyl, substituted heteroatom-containing hydrocarbyl, functionalized hydrocarbyl compounds, or mixtures thereof.

12. The method of claim 8, wherein the at least one compound containing at least two isocyanate groups is selected from at least one diisocyanate, triisocyanate, polyisocyanate compound, or mixtures thereof.

13. The method of claim 8, wherein the at least one compound containing at least two isocyanate groups is a diisocyanate compound or mixtures thereof.

14. An article of manufacture comprising at least one resin composition comprising at least one cyclic olefin, at least one metal carbene olefin metathesis catalyst, at least one adhesion promoter comprising at least one compound containing at least two isocyanate groups, at least one substrate material, and at least one functional elastomer, wherein the at least one functional elastomer is a maleic anhydride grafted styrene-ethylene/butylene-styrene hydrogenated copolymer.

15. The article of manufacture of claim 14, wherein the at least one cyclic olefin is selected from strained cyclic olefins, unstrained cyclic olefins, acyclic olefins, dienes, and unsaturated polymers, or combinations thereof, wherein the cyclic olefin may contain a functional group, or be substituted with a group, selected from halogen, hydroxyl, hydrocarbyl, alkoxy, alkenyloxy, alkynyloxy, aryloxy, aralkyloxy, alkaryloxy, acyl, acyloxy, alkoxycarbonyl, alkylcarbonato, arylcarbonato, carboxy, carboxylato, carbamoyl, alkyl-substituted carbamoyl, haloalkyl-substituted carbamoyl, aryl-substituted carbamoyl, thiocarbamoyl alkyl-substituted thiocarbamoyl, aryl-substituted thiocarbamoyl, carbamido, cyano, cyanato, thiocyanato, formyl, thioformyl, amino, alkyl-substituted amino, aryl-substituted amino, alkylamido, arylamido, imino, alkylimino, arylimino, nitro, nitroso, sulfo, sulfonato, alkylsulfanyl, arylsulfanyl, alkylsulfinyl, arylsulfinyl, alkylsulfonyl, alkylaminosulfonyl, arylsulfonyl, boryl, borono, boronato, phosphono, phosphonato, phosphinato, phospho, phosphino, or a combination thereof.

16. The article of manufacture of claim 14, wherein the at least one metal carbene olefin metathesis catalyst is a Group 8 transition metal complex having the structure of formula (I)

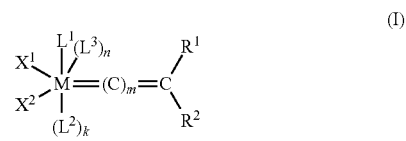

in which:
M is a Group 8 transition metal;
$L^1$, $L^2$, and $L^3$ are independently selected from neutral electron donor ligands;
n is 0 or 1, such that $L^3$ may or may not be present;
m is 0, 1, or 2;
k is 0 or 1;
$X^1$ and $X^2$ are independently anionic ligands; and
$R^1$ and $R^2$ are independently selected from hydrogen, hydrocarbyl, substituted hydrocarbyl, heteroatom-containing hydrocarbyl, substituted heteroatom-containing hydrocarbyl, and functional groups; wherein one or both of $R^1$ and $R^2$ may have the structure —$(W)_n$—$U^+V^-$, in which W is selected from hydrocarbylene, substituted hydrocarbylene, heteroatom-containing hydrocarbylene, or substituted heteroatom-containing hydrocarbylene; U is a positively charged Group 15 or Group 16 element substituted with hydrogen, hydrocarbyl, substituted hydrocarbyl, heteroatom-containing hydrocarbyl, or substituted heteroatom-containing hydrocarbyl; V is a negatively charged counterion; and n is zero or 1,
wherein any two or more of $X^1$, $X^2$, $L^1$, $L^2$, $L^3$, $R^1$, and $R^2$ can be taken together to form one or more cyclic groups, and further wherein any one or more of $X^1$, $X^2$, $L^1$, $L^2$, $L^3$, $R^1$, and $R^2$ may be attached to a support.

17. The article of manufacture of claim 14, wherein the at least one compound containing at least two isocyanate groups is a compound selected from hydrocarbyl, substituted hydrocarbyl, heteroatom-containing hydrocarbyl, substituted heteroatom-containing hydrocarbyl, functionalized hydrocarbyl compounds, or mixtures thereof.

18. The article of manufacture of claim 14, wherein the at least one compound containing at least two isocyanate groups is selected from at least one diisocyanate, triisocyanate, polyisocyanate compound, or mixtures thereof.

19. The article of manufacture of claim 14, wherein the at least one compound containing at least two isocyanate groups is a diisocyanate compound or mixtures thereof.

* * * * *